(12) United States Patent
Callcott et al.

(10) Patent No.: US 11,813,168 B2
(45) Date of Patent: Nov. 14, 2023

(54) ARTIFICIAL MENISCUS INCLUDING CIRCUMFERENTIAL AND NON-CIRCUMFERENTIAL FIBER BUNDLES

(71) Applicant: GEORGIA TECH RESEARCH CORPORATION, Atlanta, GA (US)

(72) Inventors: Trent Gardner Callcott, Atlanta, GA (US); Jonathan William Schwartz, Atlanta, GA (US); David Nelson Ku, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 362 days.

(21) Appl. No.: 17/045,886

(22) PCT Filed: Apr. 12, 2019

(86) PCT No.: PCT/US2019/027184
§ 371 (c)(1),
(2) Date: Oct. 7, 2020

(87) PCT Pub. No.: WO2019/200235
PCT Pub. Date: Oct. 17, 2019

(65) Prior Publication Data
US 2021/0137691 A1    May 13, 2021

Related U.S. Application Data

(60) Provisional application No. 62/656,564, filed on Apr. 12, 2018.

(51) Int. Cl.
*A61F 2/38* (2006.01)
*A61F 2/30* (2006.01)

(52) U.S. Cl.
CPC ........ *A61F 2/3872* (2013.01); *A61F 2/30942* (2013.01); *A61F 2002/30009* (2013.01); *A61F 2002/30957* (2013.01)

(58) Field of Classification Search
CPC .......... A61F 2/3872; A61F 2002/30754; A61F 2002/30766; A61F 2/30965;
(Continued)

(56) References Cited

U.S. PATENT DOCUMENTS 6,629,997 B2   10/2003  Mansmann
8,778,024 B2    7/2014  Shterling et al.
(Continued)

OTHER PUBLICATIONS

T. Kusayama, C. D. Harner, G. J. Carlin, J. W. Xerogeanes, and B. A. Smith, "Anatomical and biomechanical characteristics of human meniscofemoral ligaments.," *Knee Surg. Sports Traumatol. Arthrosc.*, vol. 2, No. 4, pp. 234-237, 1994.
(Continued)

*Primary Examiner* — Javier G Blanco
(74) *Attorney, Agent, or Firm* — Meunier Carlin & Curfman LLC

(57) ABSTRACT

Embodiments of an artificial meniscus are disclosed herein. An artificial meniscus includes at least one circumferential fiber bundle and the at least one non-circumferential fiber bundle embedded in a polymer material. The non-circumferential fiber bundles are fully encapsulated within the polymer material, and the circumferential fiber bundles extend out of anterior and posterior horns of the artificial meniscus to terminate in ends that are configured for fixation to bone. Methods of making and implanting artificial menisci are also disclosed herein. The methods of making include, but are not limited to, stepwise molding, layering, and curing of polymer material around the circumferential and non-circumferential fiber bundles. The methods of implanting include threading ends of the circumferential fiber bundles through first and second bone tunnels, then immobilizing the ends of the circumferential fiber bundles with respect to the bone of the subject.

15 Claims, 31 Drawing Sheets

(58) Field of Classification Search
CPC .... A61F 2002/5055; A61F 2002/30009; A61F 2002/30751; A61B 17/562; A61L 27/3654
See application file for complete search history.

(56) References Cited

U.S. PATENT DOCUMENTS

| | | | |
|---|---|---|---|
| 9,078,756 | B2 | 7/2015 | Gatt et al. |
| 9,320,606 | B2 | 4/2016 | Fox |
| 2011/0288199 | A1 | 11/2011 | Lowman et al. |
| 2012/0004725 | A1 | 1/2012 | Shterling et al. |
| 2014/0031933 | A1 | 1/2014 | Gatt et al. |
| 2016/0166389 | A1* | 6/2016 | Amis .................. A61F 2/3872 623/14.12 |

OTHER PUBLICATIONS

K. R. Stone, A. Freyer, T. Turek, A. W. Walgenbach, S. Wadhwa, and J. Crues, "Meniscal Sizing Based on Gender, Height, and Weight," *Arthrosc.—J. Arthrosc. Relat. Surg.*, vol. 23, No. 5, pp. 503-508, 2007.
C. R. Clark and J. A. Ogden, "Development of the menisci of the human knee joint. Morphological changes and their potential role in childhood meniscal injury.," *J. Bone Joint Surg. Am.*, vol. 65, No. 4, pp. 538-547, Apr. 1983.
S. P. Arnoczky and R. F. Warren, "Microvasculature of the human meniscus," *Am. J. Sports Med.*, vol. 10, No. 2, pp. 90-95, Mar. 1982.
C. S. Proctor, M. B. Schmidt, R. R. Whipple, M. A. Kelly, and V. C. Mow, "Material properties of the normal medial bovine meniscus," *J. Orthop. Res.*, vol. 7, No. 6, pp. 771-782, 1989.
J. Herwig, E. Egner, and E. Buddecke, "Chemical changes of human knee joint menisci in various stages of degeneration.," *Ann. Rheum. Dis.*, vol. 43, No. 4, pp. 635-640, Aug. 1984.
A. A. Amis, A. M. J. Bull, and I. D. McDermott, "Caracteristiques biomecaniques des ligaments et des menisques du genou [Biomechanical function of knee ligaments and menisci]," in *Pathologie ligamentaire du genou*, No. 2, Springer Verlag, 2004, pp. 45-60.
A. B. Nielsen and J. Yde, "Epidemiology of acute knee injuries: a prospective hospital investigation.," *J. Trauma*, vol. 31, No. 12, pp. 1644-1648, Dec. 1991.
A. Beaupré, R. Choukroun, R. Guidouin, R. Garneau, H. Gérardin, and A. Cardou, "Knee menisci. Correlation between microstructure and biomechanics.," *Clin. Orthop. Relat. Res.*, No. 208, pp. 72-75, Jul. 1986.
A. Bedi et al., "Dynamic Contact Mechanics of the Medial Meniscus as a Function of Radial Tear, Repair, and Partial Meniscectomy," *J. Bone Jt. Surgery—American vol.*, vol. 92, No. 6, pp. 1398-1408, Jun. 2010.
A. Bedi et al., "Dynamic contact mechanics of the medial meniscus as a function of radial tear, repair, and partial meniscectomy," *J. Bone Jt. Surg.—Ser. A*, vol. 92, No. 6, pp. 1398-1408, 2010.
A. C. T. Vrancken et al., "Short term evaluation of an anatomically shaped polycarbonate urethane total meniscus replacement in a goat model." *PloS one* 10.7 (2015): e0133138.
A. C. T. Vrancken et al., "3D geometry analysis of the medial meniscus—a statistical shape modeling approach.," *J. Anat.*, vol. 225, No. 4, pp. 395-402, Oct. 2014.
A. C. T. Vrancken, p. Buma, and T. G. Van Tienen, "Synthetic meniscus replacement: A review," *Int. Orthop.*, vol. 37, No. 2, pp. 291-299, 2013.
A. Ginés, P. Hinarejos, M. Tey, and J. C. Monllau, "Collagen Meniscus Implant. Outcomes After 4 to 7 Years," *Orthop. Proc.*, vol. 88-B, No. SUPP_II, p. 329, May 2006.
A. Hede, D. B. Jensen, P. Blyme, and S. Sonne-Holm, "Epidemiology of meniscal lesions in the knee. 1,215 open operations in Copenhagen 1982-84.," *Acta Orthop. Scand.*, vol. 61, No. 5, pp. 435-437, Oct. 1990.
A. Hede, E. Larsen, and H. Sandberg, "The long term outcome of open total and partial meniscectomy related to the quantity and site of the meniscus removed.," *Int. Orthop.*, vol. 16, No. 2, pp. 122-125, 1992.

A. J. S. Fox, A. Bedi, and S. A. Rodeo, "The Basic Science of Human Knee Menisci," *Sport. Heal. A Multidiscip. Approach*, vol. 4, No. 4, pp. 340-351, 2012.
A. Joshi et al., "Functional compressive mechanics of a PVA/PVP nucleus pulposus replacement," *Biomaterials*, vol. 27, No. 2, pp. 176-184, Jan. 2006.
A. M. Ahmed and D. L. Burke, "In-vitro measurement of static pressure distribution in synovial joints—Part I: Tibial surface of the knee," *J. Biomech. Eng.*, vol. 105, No. 3, pp. 216-225, 1983.
A. M. Lowman and N. A. Peppas, "Hydrogels," *Encycl. Control. drug Deliv.*, vol. 1, pp. 397-418, 1999.
A. S. Voloshin and J. Wosk, "Shock absorption of meniscectomized and painful knees: a comparative in vivo study.," *J. Biomed. Eng.*, vol. 5, No. 2, pp. 157-161, Apr. 1983.
A. Seitz, R. Kasisari, L. Claes, A. Ignatius, and L. Dürselen, "Forces acting on the anterior meniscotibial ligaments," *Knee Surgery, Sport. Traumatol. Arthrosc.*, vol. 20, No. 8, pp. 1488-1495, 2012.
B. B. Seedhom, D. Dowson, and V. Wright, "Proceedings: Functions of the menisci. A preliminary study.," *Ann. Rheum. Dis.*, vol. 33, No. 1, pp. 111-111, 1974.
B. E. Baker, A. C. Peckham, F. Pupparo, and J. C. Sanborn, "Review of meniscal injury and associated sports," *Am. J. Sports Med.*, vol. 13, No. 1, pp. 1-4, Jan. 1985.
B. T. Kelly et al., "Hydrogel meniscal replacement in the sheep knee: Preliminary evaluation of chondroprotective effects," *Am. J. Sports Med.*, vol. 35, No. 1, pp. 43-52, 2007.
B.-S. Lee, J.-W. Chung, J.-M. Kim, W.-J. Cho, K.-A. Kim, and S.-I. Bin, "Morphologic Changes in Fresh-Frozen Meniscus Allografts Over 1 Year," *Am. J. Sports Med.*, vol. 40, No. 6, pp. 1384-1391, Jun. 2012.
C. Chiari et al., "A tissue engineering approach to meniscus regeneration in a sheep model," *Osteoarthr. Cartil.*, vol. 14, No. 10, pp. 1056-1065, Oct. 2006.
C. M. Hassan and N. A. Peppas, "Structure and Applications of Poly(vinyl alcohol) Hydrogels Produced by Conventional Crosslinking or by Freezing/Thawing Methods," in *Biopolymers • PVA Hydrogels, Anionic Polymerisation Nanocomposites*, Berlin, Heidelberg: Springer Berlin Heidelberg, 2000, pp. 37-65.
C. M. Hassan and N. A. Peppas, "Structure and Morphology of Freeze/Thawed PVA Hydrogels," *Macromolecules*, vol. 33, No. 7, pp. 2472-2479, Apr. 2000.
C. Tudor-Locke et al., "How many steps/day are enough? For adults.," *Int. J. Behav. Nutr. Phys. Act.*, vol. 8, p. 79, Jul. 2011.
C. Van Der Straeten, B. Doyen, C. Dutordoir, W. Goedertier, S. Pirard, and J. Victor, "Short- and Medium-Term Results of Artificial Meniscal Implants," *Orthop. Proc.*, vol. 98-B, No. SUPP_4, p. 91, Jan. 2016.
Cole, Brian J., et al. "Fixation of soft tissue to bone: techniques and fundamentals." *JAAOS—Journal of the American Academy of Orthopaedic Surgeons* 24.2 (2016): 83-95.
D. Bruni, F. Iacono, I. Akkawi, M. Gagliardi, S. Zaffagnini, and M. Marcacci, "Unicompartmental knee replacement: A historical overview," *Joints*, vol. 1, No. 2, pp. 45-47, 2013.
D. C. Fithian, M. A. Kelly, and V. C. Mow, "Material properties and structure-function relationships in the menisci.," *Clin. Orthop. Relat. Res.*, No. 252, pp. 19-31, Mar. 1990.
D. Kumar, K. T. Manal, and K. S. Rudolph, "Knee joint loading during gait in healthy controls and individuals with knee osteoarthritis," *Osteoarthr. Cartil.*, vol. 21, No. 2, pp. 298-305, 2013.
D. L. Skaggs, W. H. Warden, and V. C. Mow, "Radial tie fibers influence the tensile properties of the bovine medial meniscus," *J. Orthop. Res.*, vol. 12, No. 2, pp. 176-185, Mar. 1994.
E. A. Makris, P. Hadidi, and K. A. Athanasiou, "The knee meniscus: Structure-function, pathophysiology, current repair techniques, and prospects for regeneration," *Biomaterials*, vol. 32, No. 30, pp. 7411-7431, 2011.
E. Genovese et al., "Follow-up of collagen meniscus implants by MRI," *Radiol. Med.*, vol. 112, No. 7, pp. 1036-1048, Oct. 2007.
E. Kon et al., "Tissue engineering for total meniscal substitution: animal study in sheep model," *Tissue Eng. Part A*, 2008.
E. Salernitano and C. Migliaresi, "Composite Materials for Biomedical Applications: A Review:," https://doi.org/10.1177/228080000300100102, Jan. 2018.

(56) References Cited

OTHER PUBLICATIONS

F. A. Barber and J. E. McGarry, "Meniscal Repair Techniques," *Sports Med. Arthrosc.*, vol. 15, No. 4, pp. 199-207, Dec. 2007.
F. Franceschini and M. Galetto, "A new approach for evaluation of risk priorities of failure modes in FMEA," *Int. J. Prod. Res.*, vol. 39, No. 13, pp. 2991-3002, Jan. 2001.
G. Zur et al., "Chondroprotective effects of a polycarbonate-urethane meniscal implant: Histopathological results in a sheep model," *Knee Surgery, Sport. Traumatol. Arthrosc.*, vol. 19, No. 2, pp. 255-263, 2011.
H. Kurosawa, T. Fukubayashi, and H. Nakajima, "Load-bearing mode of the knee joint: physical behavior of the knee joint with or without menisci.," *Clin. Orthop. Relat. Res.*, No. 149, pp. 283-290, Jun. 1980.
H. Luks, "Recovery After Meniscal Tear Surgery," *Orthopedic Surgery and Sports Medicine*, 2018. [Online]. Available: https://www.howardluksmd.com/meniscal-tear-recovery-surgery/. [Accessed: Apr. 8, 2018].
H. N. Chia and M. L. Hull, "Compressive moduli of the human medial meniscus in the axial and radial directions at equilibrium and at a physiological strain rate," *J. Orthop. Res.*, vol. 26, No. 7, pp. 951-956, 2008.
H. Roos, M. Lauren, T. Adalberth, E. M. Roos, K. Jonsson, and L. S. Lohmander, "Knee osteoarthritis after meniscectomy: Prevalence of radiographic changes after twenty-one years, compared with matched controls," *Arthritis Rheum.*, vol. 41, No. 4, pp. 687-693, Apr. 1998.
I. D. McDermott and A. A. Amis, "The consequences of meniscectomy," *J. Bone Jt. Surg.—Br. vol.*, vol. 88-B, No. 12, pp. 1549-1556, 2006.
I. D. McDermott, S. D. Masouros, and A. A. Amis, "Biomechanics of the menisci of the knee," *Curr. Orthop.*, vol. 22, No. 3, pp. 193-201, 2008.
I. Kutzner et al., "Loading of the knee joint during activities of daily living measured in vivo in five subjects," *J. Biomech.*, vol. 43, No. 11, pp. 2164-2173, 2010.
I. M. Levy, P. A. Torzilli, and R. F. Warren, "The effect of medial meniscectomy on anterior-posterior motion of the knee.," *J. Bone Joint Surg. Am.*, vol. 64, No. 6, pp. 883-888, Jul. 1982.
I. P. Terzidis, A. Christodoulou, A. Ploumis, P. Givissis, K. Natsis, and M. Koimtzis, "Meniscal Tear Characteristics in Young Athletes with a Stable Knee," *Am. J. Sports Med.*, vol. 34, No. 7, pp. 1170-1175, Jul. 2006.
J. Babu, R. M. Shalvoy, and S. B. Behrens, "Diagnosis and Management of Meniscal Injury.," *R. I. Med. J. (2013)*, vol. 99, No. 10, pp. 27-30, Oct. 2016.
J. C. Jones, R. Burks, B. D. Owens, R. X. Sturdivant, S. J. Svoboda, and K. L. Cameron, "Incidence and risk factors associated with meniscal injuries among active-duty US military service members.," *J. Athl. Train.*, vol. 47, No. 1, pp. 67-73. 2012.
J. C. Monllau et al., "Outcome After Partial Medial Meniscus Substitution With the Collagen Meniscal Implant at a Minimum of 10 Years' Follow-up," *Arthrosc. J. Arthrosc. Relat. Surg.*, vol. 27, No. 7, pp. 933-943, Jul. 2011.
J. C. Monllau, X. Pelfort, and M. Tey, "Collagen Meniscus Implant: Technique and Results," in *The Meniscus*, Berlin, Heidelberg: Springer Berlin Heidelberg, 2010, pp. 373-382.
J. D. Henderson, R. H. Mullarky, and D. E. Ryan, "Tissue biocompatibility of kevlar aramid fibers and polymethylmethacrylate, composites in rabbits," *J. Biomed. Mater. Res.*, vol. 21, No. 1, pp. 59-64, Jan. 1987.
J. J. Elsner, S. Portnoy, G. Zur, F. Guilak, A. Shterling, and E. Linder-Ganz, "Design of a Free-Floating Polycarbonate-Urethane Meniscal Implant Using Finite Element Modeling and Experimental Validation," *J. Biomech. Eng.*, vol. 132, No. 9, p. 95001, 2010.
J. L. Cook, "The current status of treatment for large meniscal defects.," *Clin. Orthop. Relat. Res.*, No. 435, pp. 88-95, Jun. 2005.
J. L. Holloway, "Development and Characterization of UHMWPE Fiber-Reinforced Hydrogels for Meniscal Replacement," Drexel University, 2012.
J. L. Holloway, A. M. Lowman, and G. R. Palmese, "Mechanical evaluation of poly(vinyl alcohol)-based fibrous composites as biomaterials for meniscal tissue replacement," *Acta Biomater.*, vol. 6, No. 12, pp. 4716-4724, 2010.
J. L. Holloway, A. M. Lowman, M. R. Vanlandingham, and G. R. Palmese, "Interfacial optimization of fiber-reinforced hydrogel composites for soft fibrous tissue applications," *Acta Biomater.*, vol. 10, No. 8, pp. 3581-3589, 2014.
J.-M. Fayard, H. Pereira, E. Servien, S. Lustig, and P. Neyret, "Meniscectomy: Global Results—Complications," in *The Meniscus*, Berlin, Heidelberg: Springer Berlin Heidelberg, 2010, pp. 177-190.
K. A. Athanasiou and J. Sanchez-Adams, *Engineering the Knee Meniscus*. Morgan & Claypool, 2009.
K. Bloecker et al., "Revision 1 Size and position of the healthy meniscus, and its Correlation with sex, height, weight, and bone area—a cross-sectional study," *BMC Musculoskelet. Disord.*, vol. 12, pp. 1-9, 2011.
K. L. Markolf, S. R. Jackson, and D. R. McAllister, "Force measurements in the medial meniscus posterior horn attachment: Effects of anterior cruciate ligament removal," *Am. J. Sports Med.*, vol. 40, No. 2, pp. 332-338, 2012.
K. L. Spiller, S. J. Laurencin, D. Charlton, S. A. Maher, and A. M. Lowman, "Superporous hydrogels for cartilage repair: Evaluation of the morphological and mechanical properties," *Acta Biomater.*, vol. 4, No. 1, pp. 17-25, Jan. 2008.
K. Messner and J. Gao, "The menisci of the knee joint. Anatomical and functional characteristics, and a rationale for clinical treatment.," *J. Anat.*, vol. 193 ( Pt 2), pp. 161-178, Aug. 1998.
K. Messner and J. Gillquist, "Prosthetic replacement of the rabbit medial meniscus," *J. Biomed. Mater. Res.*, vol. 27, No. 9, pp. 1165-1173, Sep. 1993.
K. Messner, "Meniscal substitution with a Teflon-periosteal composite graft: a rabbit experiment," *Biomaterials*, vol. 15, No. 3, pp. 223-230, Feb. 1994.
K. R. Stone, W. G. Rodkey, R. Webber, L. McKinney, and J. R. Steadman, "Meniscal regeneration with copolymeric collagen scaffolds," *Am. J. Sports Med.*, vol. 20, No. 2, pp. 104-111, Mar. 1992.
K. Sommerlath, M. Gallino, and J. Gillquist, "Biomechanical characteristics of different artificial substitutes for rabbit medial meniscus and effect of prosthesis size on knee cartilage," *Clin. Biomech.*, vol. 7, No. 2, pp. 97-103, May 1992.
L. McCann, E. Ingham, Z. Jin, and J. Fisher, "Influence of the meniscus on friction and degradation of cartilage in the natural knee joint," *Osteoarthr. Cartil.*, vol. 17, No. 8, pp. 995-1000, Aug. 2009.
L. S. Lohmander, P. M. Englund, L. L. Dahl, and E. M. Roos, "The Long-term Consequence of Anterior Cruciate Ligament and Meniscus Injuries," *Am. J. Sports Med.*, vol. 35, No. 10, pp. 1756-1769, Oct. 2007.
M. A. Sweigart et al., "Intraspecies and interspecies comparison of the compressive properties of the medial meniscus," *Ann. Biomed. Eng.*, vol. 32, No. 11, pp. 1569-1579, 2004.
M. D. Joshi, J.-K Suh, T. Marui, and S. L.-. Woo, "Interspecies variation of compressive biomechanical properties of the meniscus," *J. Biomed. Mater. Res.*, vol. 29, No. 7, pp. 823-828, 1995.
M. Drakos and A. Allen, "Meniscal Structure, Function, Repair, and Replacement," *Oncology and Basic Science*, 2016. [Online]. Available: https://oncohemakey.com/meniscal-structure-function-repair-and-replacement/. [Accessed: Apr. 8, 2018].
M. E. Baratz, F. H. Fu, and R. Mengato, "Meniscal tears: The effect of meniscectomy and of repair on intraarticular contact areas and stress in the human knee," *Am. J. Sports Med.*, vol. 14, No. 4, pp. 270-275, Jul. 1986.
M. ElAttar, A. Dhollander, R. Verdonk, K. F. Almqvist, and P. Verdonk, "Twenty-six years of meniscal allograft transplantation: Is it still experimental? A meta-analysis of 44 trials," *Knee Surgery, Sport. Traumatol. Arthrosc.*, vol. 19, No. 2, pp. 147-157, 2011.
M. Englund and L. S. Lohmander, "Risk factors for symptomatic knee osteoarthritis fifteen to twenty-two years after meniscectomy," *Arthritis Rheum.*, vol. 50, No. 9, pp. 2811-2819, Sep. 2004.
M. Freutel et al., "Medial meniscal displacement and strain in three dimensions under compressive loads: MR assessment," *J. Magn. Reson. Imaging*, vol. 40, No. 5, pp. 1181-1188, 2014.

(56) References Cited

OTHER PUBLICATIONS

M. I. Baker, S. P. Walsh, Z. Schwartz, and B. D. Boyan, "A review of polyvinyl alcohol and its uses in cartilage and orthopedic applications," *J. Biomed. Mater. Res.—Part B Appl. Biomater.*, vol. 100 B, No. 5, pp. 1451-1457, 2012.
M. Jassal and S. Ghosh, *Aramid fibres—An overview*, vol. 27. 190-306, 2002.
M. Kobayashi, J. Toguchida, and M. Oka, "Development of an artificial meniscus using polyvinyl alcohol-hydrogel for early return to, and continuance of, athletic life in sportspersons with severe meniscus injury. I: Mechanical evaluation," *Knee*, vol. 10, No. 1, pp. 47-51, 2003.
M. Kobayashi, Y. S. Chang, and M. Oka, "A two year in vivo study of polyvinyl alcohol-hydrogel (PVA-H) artificial meniscus," *Biomaterials*, vol. 26, No. 16, pp. 3243-3248, 2005.
M. Majewski, H. Susanne, and S. Klaus, "Epidemiology of athletic knee injuries: A 10-year study," *Knee*, vol. 13, No. 3, pp. 184-188, Jun. 2006.
M. McDowell, C. Fryar, C. Ogden, and K. Flegal, "Anthropometric reference data for children and adults: United States, 2003-2006," *Natl. Health Stat. Report.*, No. 10, pp. 2003-2006, 2008.
M. Shemesh, R. Asher, E. Zylberberg, F. Guilak, E. Linder-Ganz, and J. J. Elsner, "Viscoelastic properties of a synthetic meniscus implant," *J. Mech. Behav. Biomed. Mater.*, vol. 29, pp. 42-55, 2014.
M. T. Hirschmann and N. F. Friederich, "Classification: Discoid Meniscus, Traumatic Lesions," in *The Meniscus*, Berlin, Heidelberg: Springer Berlin Heidelberg, 2010, pp. 241-246.
M. Tissakht and A. M. Ahmed, "Tensile stress-strain characteristics of the human meniscal material," *J. Biomech.*, vol. 28, No. 4, pp. 411-422, 1995.
N. A. Peppas, "Turbidimetric studies of aqueous poly(vinyl alcohol) solutions," *Die Makromol. Chemie*, vol. 176, No. 11, pp. 3433-3440, Nov. 1975.
N. Maffulli, U. G. Longo, S. Campi, and V. Denaro, "Meniscal tears.," *Open access J. Sport. Med.*, vol. 1, pp. 45-54, Apr. 2010.
P. Beaufils and N. Pujol, "Meniscal repair: Technique," *Orthop. Traumatol. Surg. Res.*, vol. 104, No. 1, pp. S137-S145, Feb. 2018.
P. Buma, N. N. Ramrattan, T. G. van Tienen, and R. P. H. Veth, "Tissue engineering of the meniscus.," *Biomaterials*, vol. 25, No. 9, pp. 1523-1532, Apr. 2004.
P. Cignoni et al., "MeshLab: an Open-Source Mesh Processing Tool," *Sixth Eurographics Ital. Chapter Conf.*, pp. 129-136, 2008.
P. E. Greis, D. D. Bardana, M. C. Holmstrom, and R. T. Burks, "Meniscal injury: I. Basic science and evaluation.," *J. Am. Acad. Orthop. Surg.*, vol. 10, No. 3, pp. 168-176.
P. G. Bullough, L. Munuera, J. Murphy, and A. M. Weinstein, "The strength of the menisci of the knee as it relates to their fine structure.," *J. Bone Joint Surg. Br.*, vol. 52, No. 3, pp. 564-567, Aug. 1970.
P. Verdonk and P. Vererfve, "Traumatic Lesions: Stable Knee, ACL Knee," in *The Meniscus*, Berlin, Heidelberg: Springer Berlin Heidelberg, 2010, pp. 45-49.
P. Verdonk et al., "Successful Treatment of Painful Irreparable Partial Meniscal Defects With a Polyurethane Scaffold," *Am. J. Sports Med.*, vol. 40, No. 4, pp. 844-853, Apr. 2012.
R. H. Brophy, J. Cottrell, S. A. Rodeo, T. M. Wright, R. F. Warren, and S. A. Maher, "Implantation of a synthetic meniscal scaffold improves joint contact mechanics in a partial meniscectomy cadaver model," *J. Biomed. Mater. Res. Part A*, vol. 9999A, No. 3, p. NA-NA, Mar. 2009.
R. Pöllänen, A.-M. Tikkanen, M. J. Lammi, and R. Lappalainen, "The effect of loading and material on the biomechanical properties and vitality of bovine cartilage in vitro.," *J. Appl. Biomater. Biomech.*, vol. 9, No. 1, pp. 47-53, 2011.
R. Ricciardi, F. Auriemma, C. Gaillet, C. De Rosa, and F. Lauprêtre, "Investigation of the Crystallinity of Freeze/Thaw Poly(vinyl alcohol) Hydrogels by Different Techniques," *Macromolecules*, vol. 37, No. 25, pp. 9510-9516, Dec. 2004.
R. S. Jones et al., "Direct measurement of hoop strains in the intact and torn human medial meniscus.," *Clin. Biomech. (Bristol, Avon)*, vol. 11, No. 5, pp. 295-300, Jul. 1996.
R. Seil and D. Pape, "Meniscal Repair: Biomechanics," in *The Meniscus*, Berlin, Heidelberg: Springer Berlin Heidelberg, 2010, pp. 107-117.
R. T. C. Welsing et al., "Effect on Tissue Differentiation and Articular Cartilage Degradation of a Polymer Meniscus Implant," *Am. J. Sports Med.*, vol. 36, No. 10, pp. 1978-1989, Oct. 2008.
S. A. Maher et al., "Evaluation of a Porous Polyurethane Scaffold in a Partial Meniscal Defect Ovine Model," *Arthrosc. J. Arthrosc. Relat. Surg.*, vol. 26, No. 11, pp. 1510-1519, Nov. 2010.
S. A. Maher, S. A. Rodeo, H. G. Potter, L. J. Bonassar, T. M. Wright, and R. F. Warren, "A Pre-Clinical Test Platform for the Functional Evaluation of Scaffolds for Musculoskeletal Defects: The Meniscus," *HSS J.*, vol. 7, No. 2, pp. 157-163, 2011.
S. C. Mordecai, N. Al-Hadithy, H. E. Ware, and C. M. Gupte, "Treatment of meniscal tears: An evidence based approach.," *World J. Orthop.*, vol. 5, No. 3, pp. 233-241, Jul. 2014.
S. J. Spencer, A. Saithna, M. R. Carmont, M. S. Dhillon, P. Thompson, and T. Spalding, "Meniscal scaffolds: Early experience and review of the literature," *Knee*, vol. 19, No. 6, pp. 760-765, Dec. 2012.
S. R. Stauffer and N. A. Peppast, "Poly(vinyl alcohol) hydrogels prepared by freezing-thawing cyclic processing," *Polymer (Guildf).*, vol. 33, No. 18, pp. 3932-3936, Sep. 1992.
S.-W. Kang et al., "Regeneration of whole meniscus using meniscal cells and polymer scaffolds in a rabbit total meniscectomy model," *J. Biomed. Mater. Res. Part A*, vol. 78A, No. 3, pp. 638-651, Sep. 2006.
T. D. Lauder, S. P. Baker, G. S. Smith, and A. E. Lincoln, "Sports and physical training injury hospitalizations in the army.," *Am. J. Prev. Med.*, vol. 18, No. 3 Suppl, pp. 118-128, Apr. 2000.
T. Fukubayashi and H. Kurosawa, "The contact area and pressure distribution pattern of the knee: A study of normal and osteoarthrotic knee joints," *Acta Orthop.*, vol. 51, No. 1-6, pp. 871-879, 1980.
T. G. Tienen et al., "Replacement of the Knee Meniscus by a Porous Polymer Implant," *Am. J. Sports Med.*, vol. 34, No. 1, pp. 64-71, Jan. 2006.
T. G. van Tienen, G. Hannink, and P. Buma, "Meniscus Replacement Using Synthetic Materials," *Clin. Sports Med.*, vol. 28, No. 1, pp. 143-156, Jan. 2009. Abstract.
T. Hatakeyema, J. Uno, C. Yamada, A. Kishi, and H. Hatakeyama, "Gel-sol transition of poly(vinyl alcohol) hydrogels formed by freezing and thawing," *Thermochim. Acta*, vol. 431, No. 1-2, pp. 144-148, Jun. 2005.
T. J. Fairbank, "Knee joint changes after meniscectomy.," *J. Bone Joint Surg. Br.*, vol. 30B, No. 4, pp. 664-670, Nov. 1948.
V. I. Lozinsky, L. G. Damshkaln, I. N. Kurochkin, and I. I. Kurochkin, "Study of cryostructuring of polymer systems: 28. Physicochemical properties and morphology of poly(vinyl alcohol) cryogels formed by multiple freezing-thawing," *Colloid J.*, vol. 70, No. 2, pp. 189-198, Apr. 2008.
W. E. GarrettJr et al., "American Board of Orthopaedic Surgery Practice of the Orthopaedic Surgeon: Part-II, Certification Examination Case Mix," *J. Bone Jt. Surg.*, vol. 88, No. 3, p. 660, Mar. 2006.
W. G. Rodkey et al., "Comparison of the Collagen Meniscus Implant with Partial Meniscectomy," *J. Bone Jt. Surgery—American vol.*, vol. 90, No. 7, pp. 1413-1426, Jul. 2008.
W. R. Krause, M. H. Pope, R. J. Johnson, and D. G. Wilder, "Mechanical changes in the knee after meniscectomy.," *J. Bone Joint Surg. Am.*, vol. 58, No. 5, pp. 599-604, Jul. 1976.
Y. Wada, M. Amiel, F. Harwood, H. Moriya, and D. Amiel, "Architectural remodeling in deep frozen meniscal allografts after total meniscectomy.," *Arthroscopy*, vol. 14, No. 3, pp. 250-257, Apr. 1998.
Y.-S. Chang, H.-O. Gu, M. Kobayashi, and M. Oka, "Comparison of the bony ingrowth into an osteochondral defect and an artificial osteochondral composite device in load-bearing joints," *Knee*, vol. 5, No. 3, pp. 205-213, Jun. 1998.
International Preliminary Report on Patentability issued for Application No. PCT/US2019/027184, dated Oct. 22, 2020.

(56) References Cited

OTHER PUBLICATIONS

International Search Report and Written Opinion dated Jun. 14, 2019, from International Application No. PCT/US2019/027184, 10 pages.

* cited by examiner

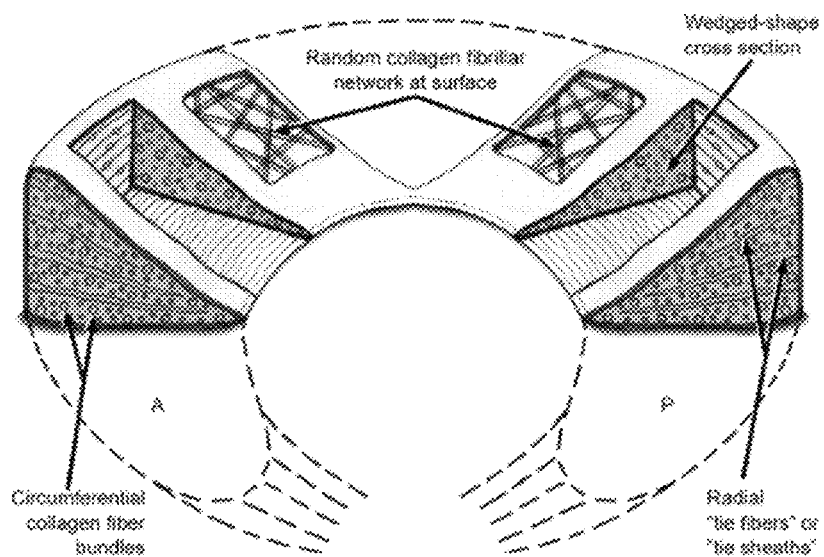
FIG. 3
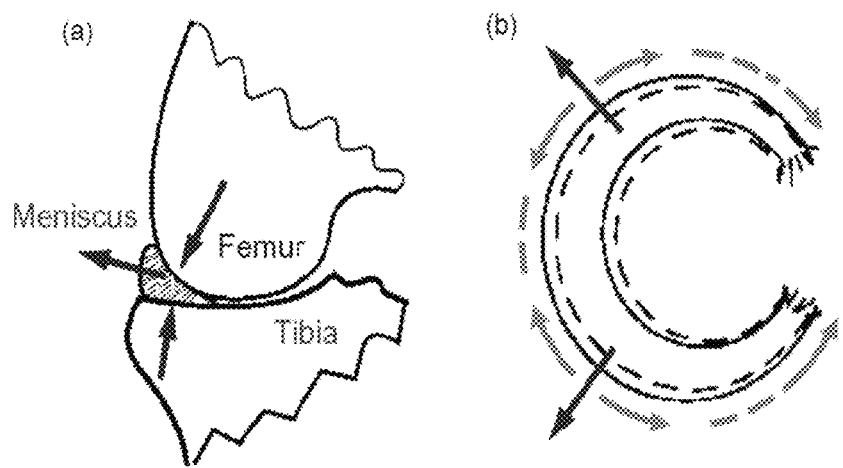
FIG. 4A  FIG. 4B

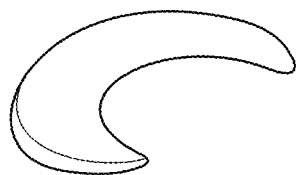
*FIG. 5A*
  
*FIG. 5B*  *FIG. 5C*  *FIG. 5D*
  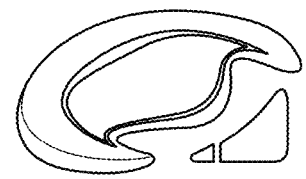
*FIG. 5E*  *FIG. 5F*  *FIG. 5G*
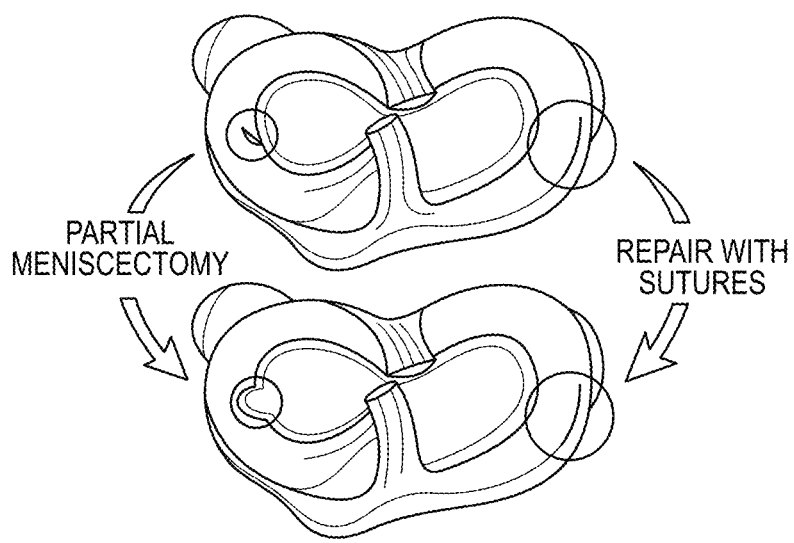
*FIG. 6*

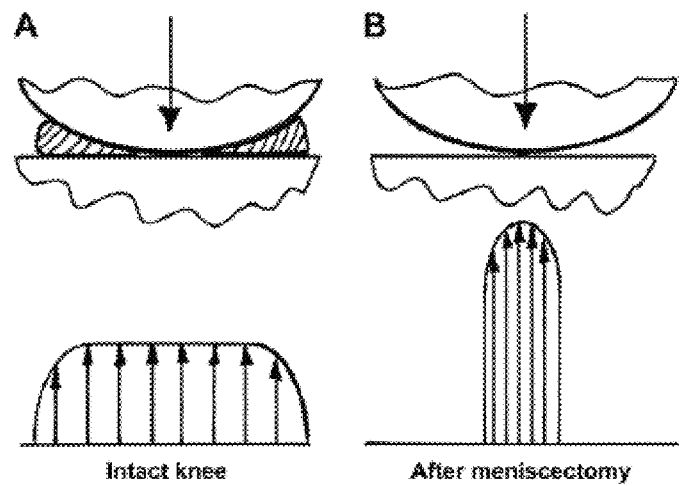
FIG. 7A  FIG. 7B
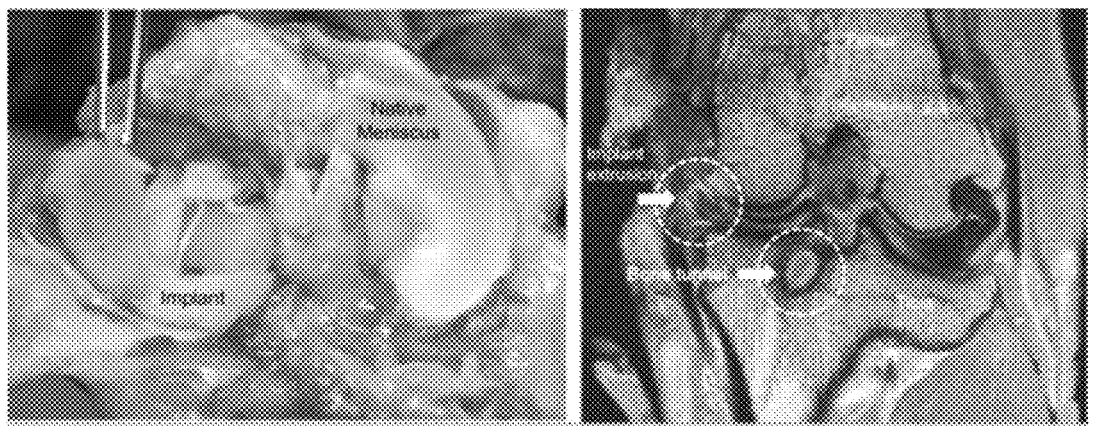
FIG. 8

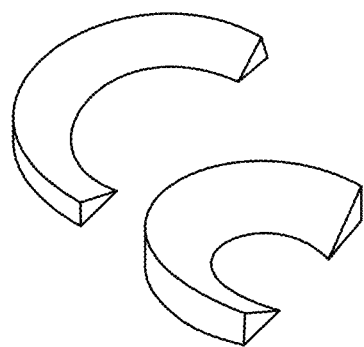
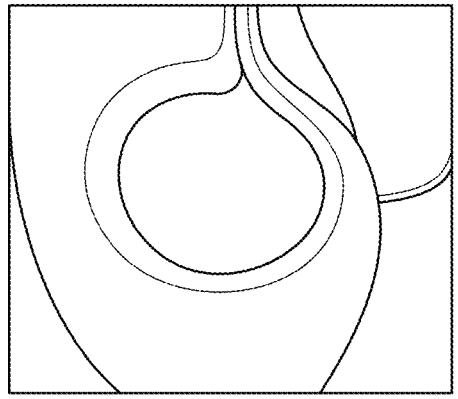
*FIG. 9A*  *FIG. 9B*
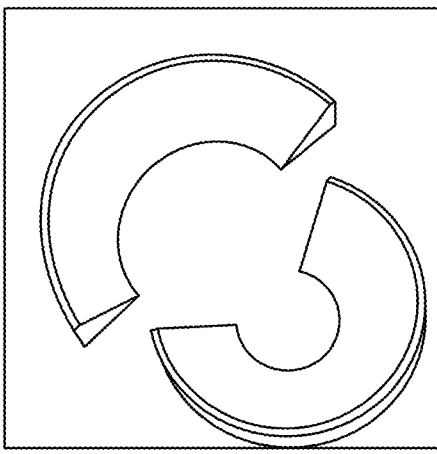
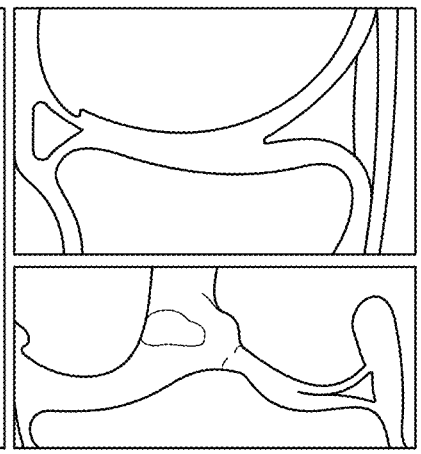
*FIG. 10A*  *FIG. 10B*
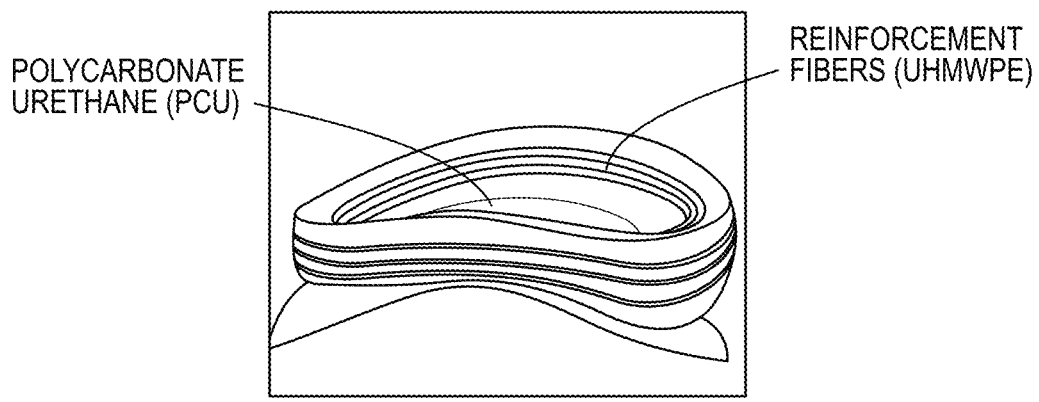
*FIG. 11*

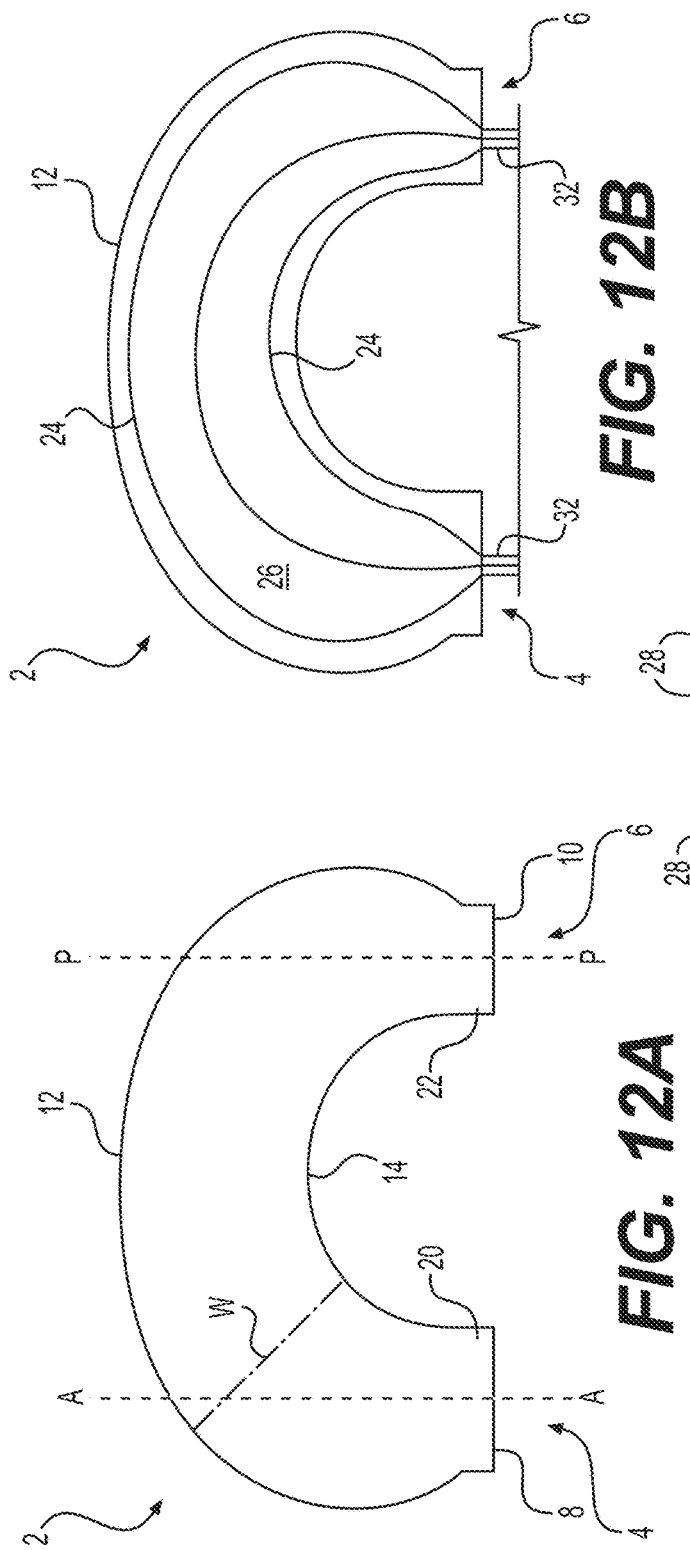

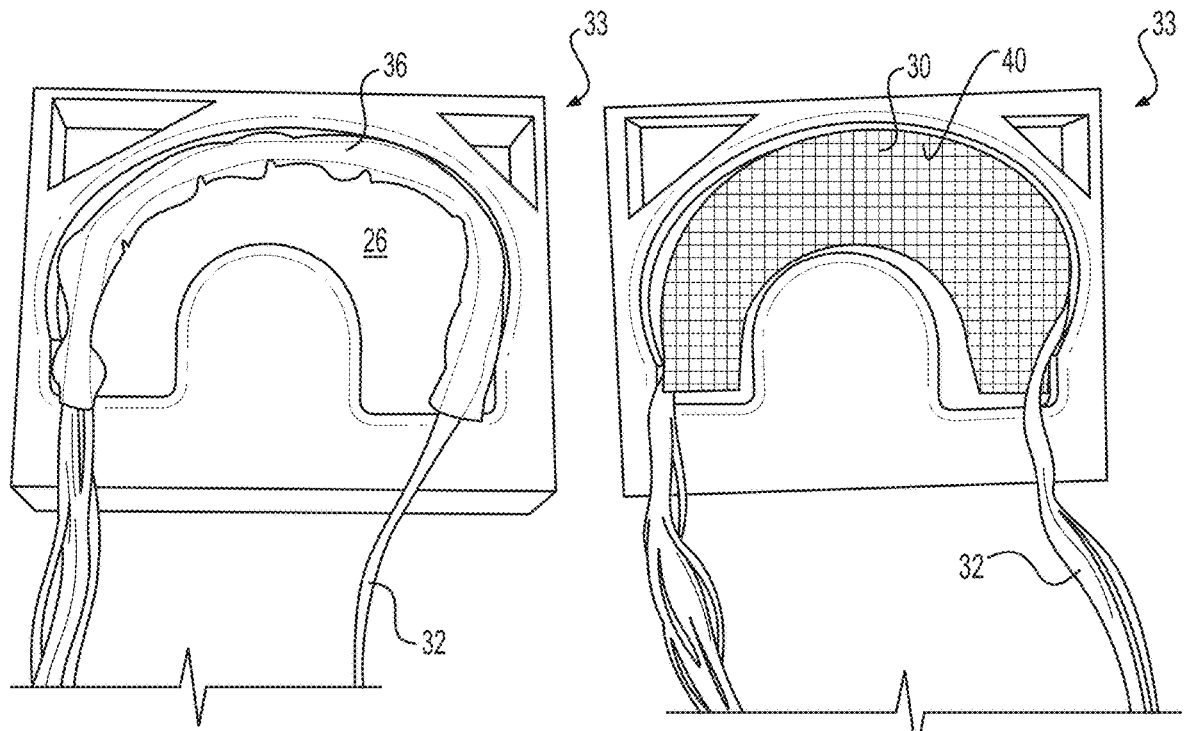
FIG. 17D
FIG. 17E
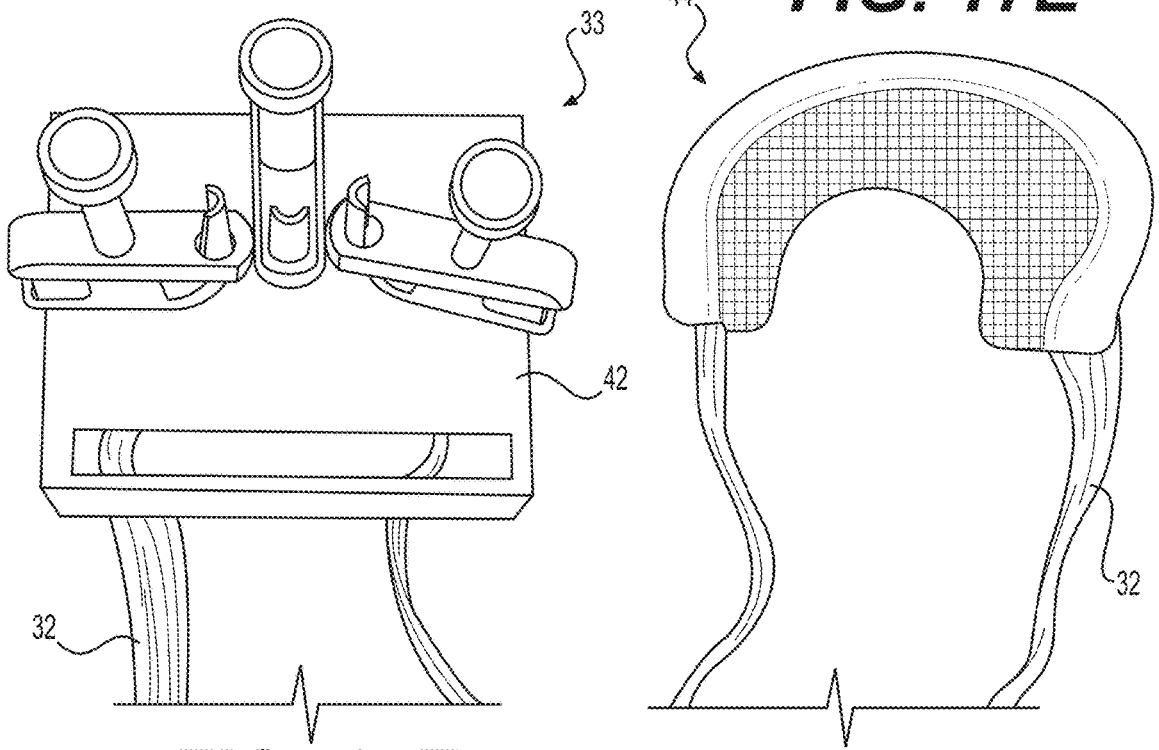
FIG. 17F
FIG. 17G

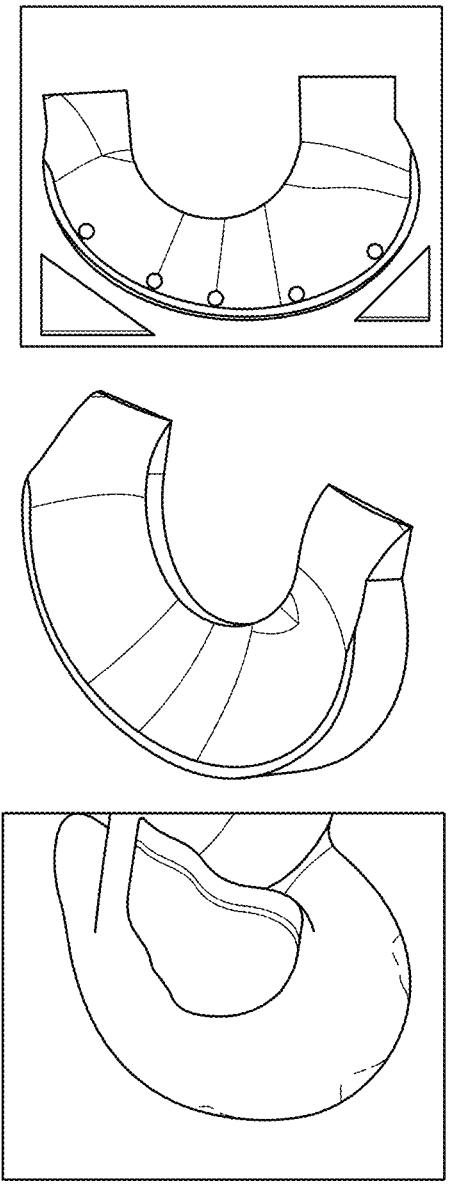
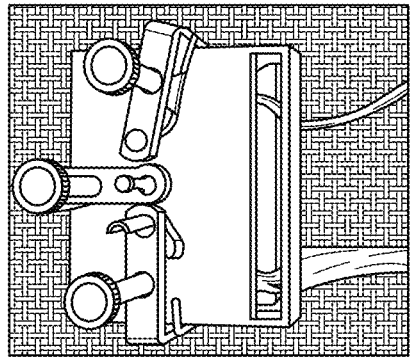
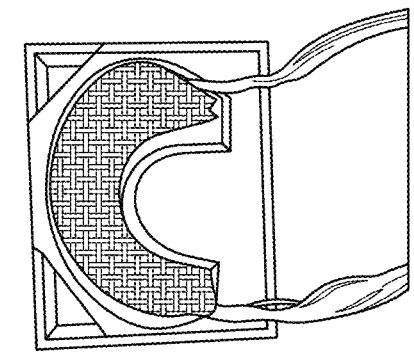
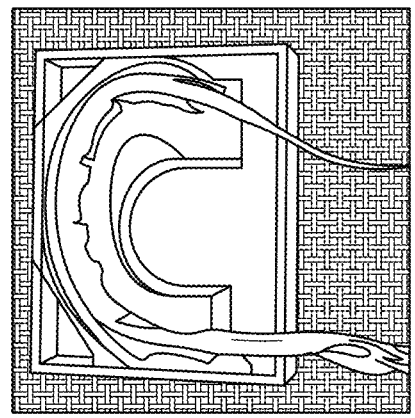
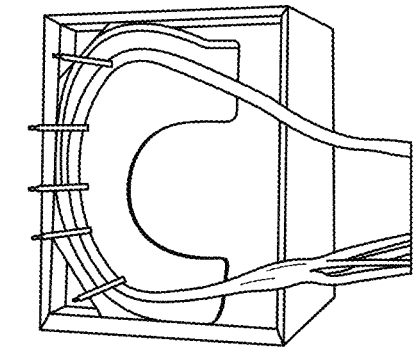
FIG. 22A  FIG. 22B  FIG. 22C  FIG. 22D  FIG. 22E  FIG. 22F  FIG. 22G

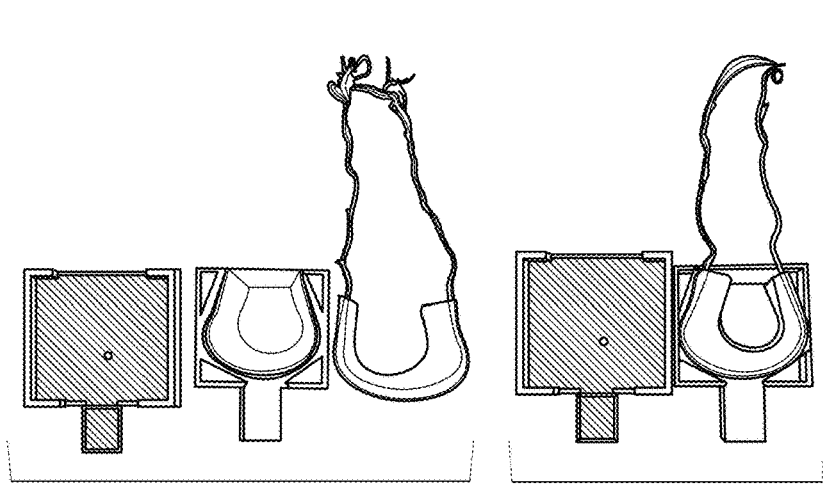
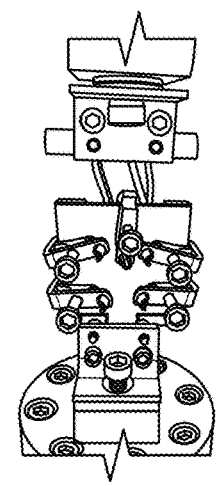
FIG. 28A          FIG. 28B          FIG. 28C
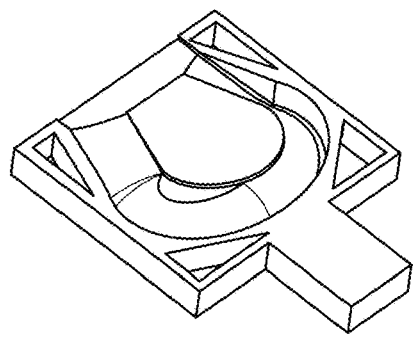
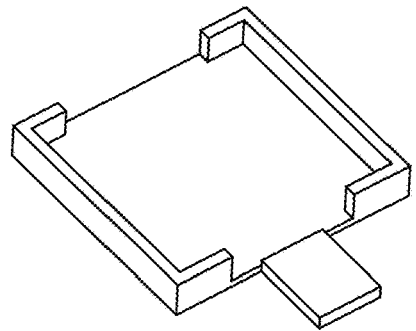
FIG. 29A          FIG. 29B
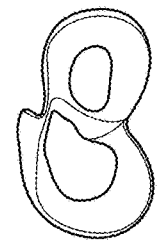
FIG. 30A          FIG. 30B          FIG. 30C
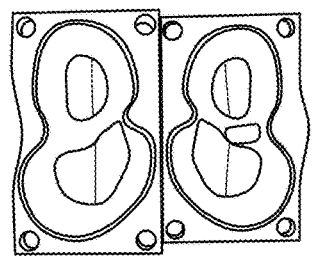
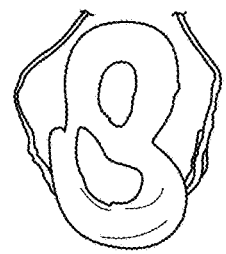
FIG. 30D          FIG. 30E

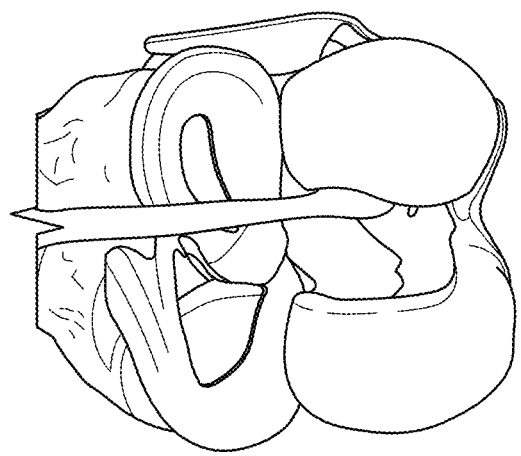
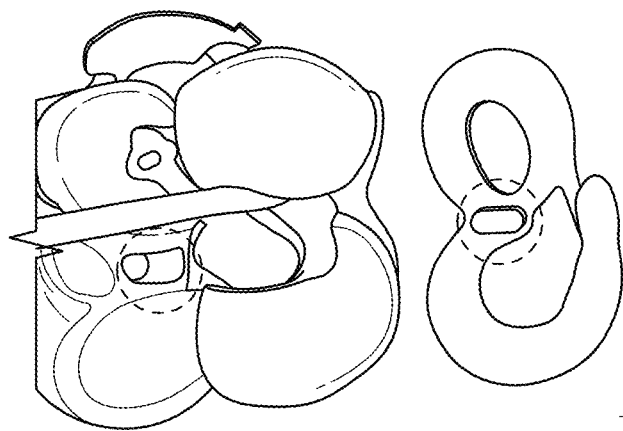
FIG. 32
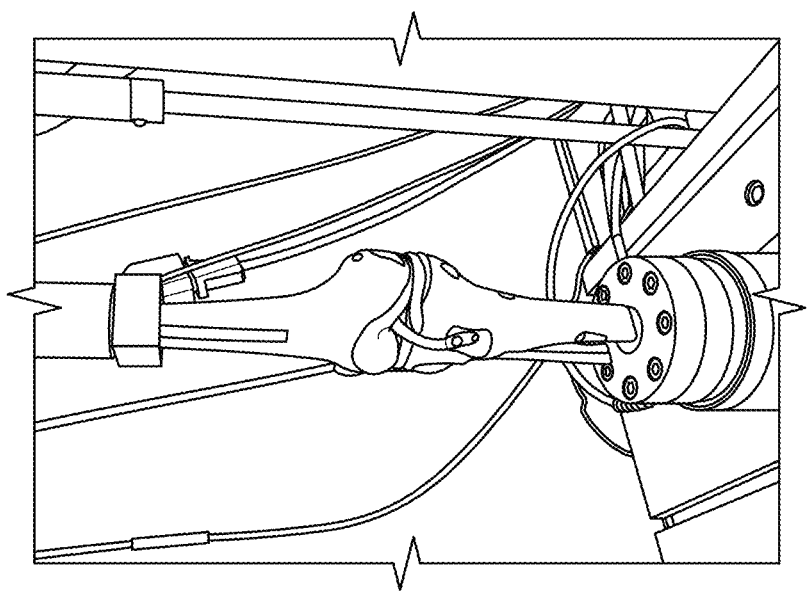
FIG. 31

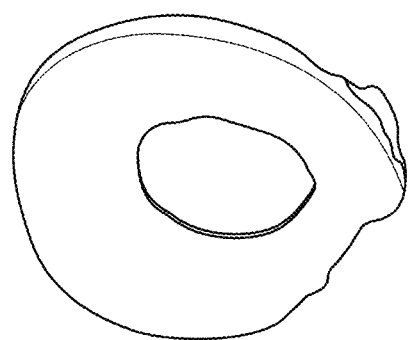
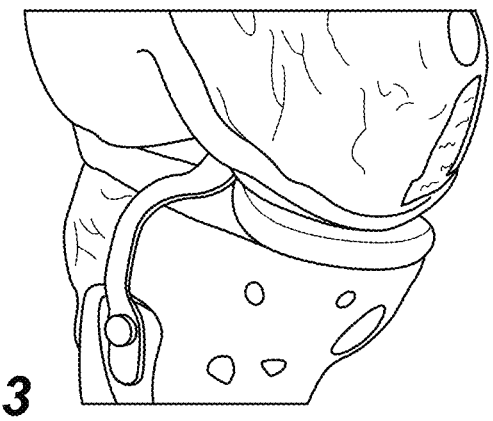
FIG. 33
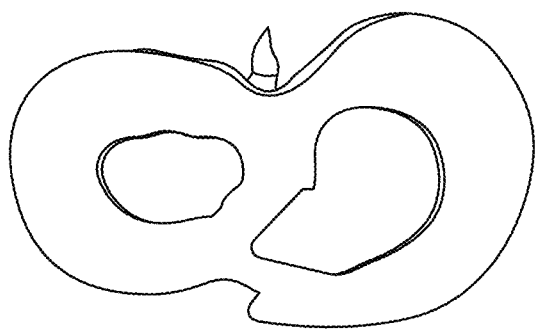
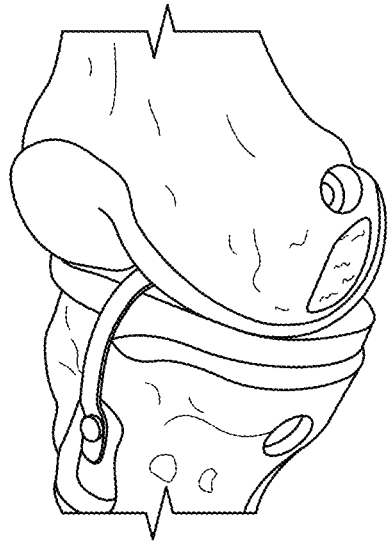
FIG. 34
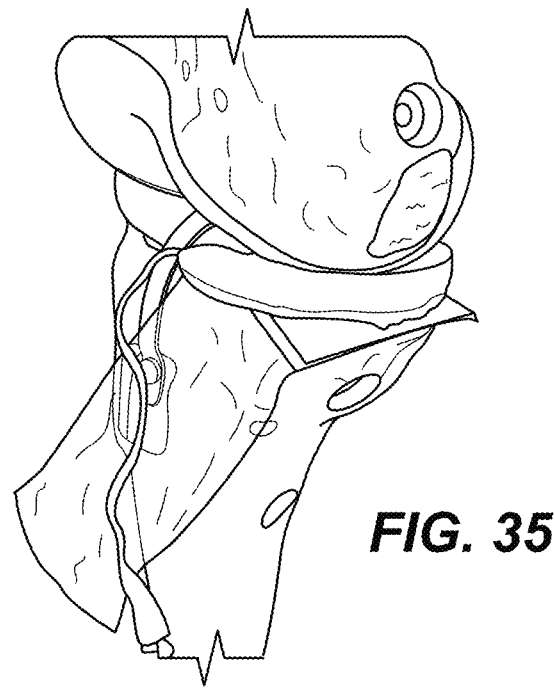
FIG. 35

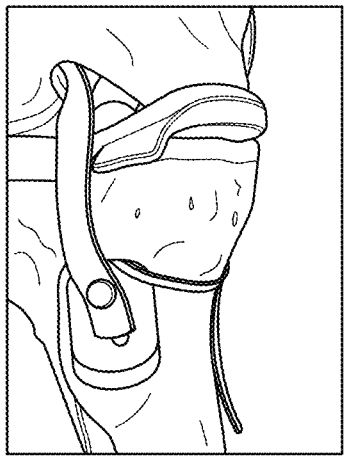
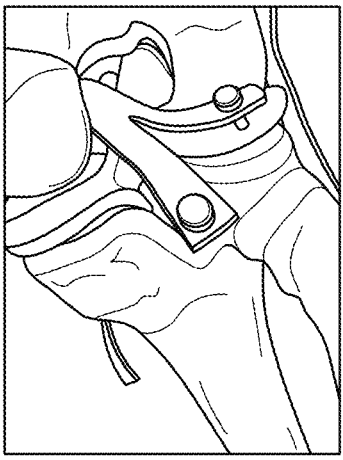
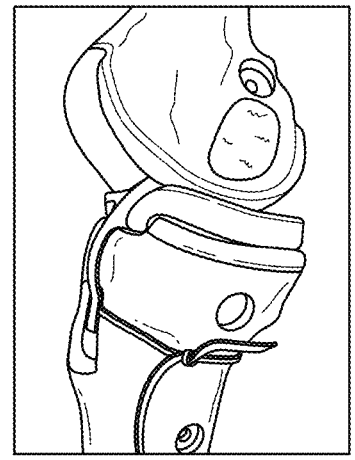
*FIG. 36A*    *FIG. 36B*    *FIG. 36C*
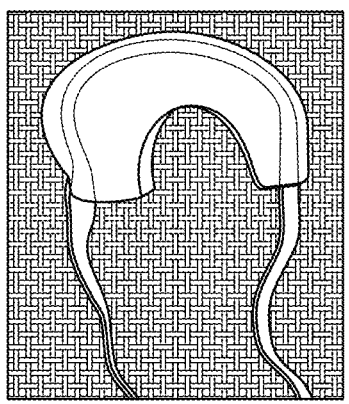
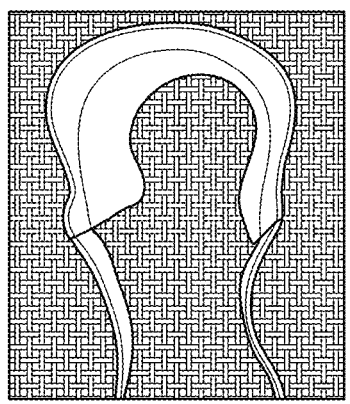
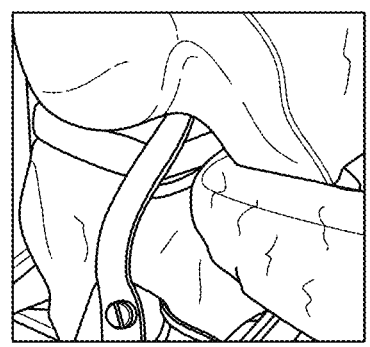
*FIG. 37A*    *FIG. 37B*    *FIG. 37C*

ARTIFICIAL MENISCUS INCLUDING CIRCUMFERENTIAL AND NON-CIRCUMFERENTIAL FIBER BUNDLES

RELATED APPLICATIONS

This application claims priority to U.S. Provisional Application No. 62/656,564, filed Apr. 12, 2018, which is hereby incorporated by reference in its entirety.

STATEMENT REGARDING FEDERALLY SPONSORED RESEARCH OR DEVELOPMENT

This invention was made with Government Support under Grant No. P50 FD004193 awarded by the Food and Drug Administration. The Government has certain rights in the invention.

FIELD

This invention relates to orthopedic implants, and more specifically, to meniscal implants.

BACKGROUND

The lateral and medial menisci are two semilunar wedges of dense fibrocartilage in the knee joint between the tibia and femur. The shape of the menisci allow conformity between the femoral condyles and the tibial plateaus. They are attached to the tibia and femur through various ligaments, with the main attachment points being to the tibia at the posterior and anterior horns (see FIG. 1), but have mobility within the knee [1]. The lateral and medial menisci have different dimensions within the joint, with the lateral meniscus being approximately 34.8-37.0 mm long and 28.4-29.8 mm wide and the medial meniscus being 43.8-45.1 mm long and 29.5-32.2 mm wide [2]. In addition to having a wider variety of shape, size, and thickness, the lateral meniscus also occupies a larger portion of the tibial plateau area at 75-93% when compared to the medial meniscus at 51-74% [3].

The adult menisci are separated into distinct regions when it comes to vascularization, as shown in FIG. 2. The peripheral "red zone" contains a blood supply and nerves while the central "white zone" is avascular and aneural, which negatively affects the healing capacity within this central region of the menisci. The two regions are separated by a transitional "red-white zone" that has limited healing ability [4]. Water makes up most of the meniscal tissue, accounting for about 72% of its weight. It is also composed of fibrochondrocyte cells and an extracellular matrix consisting mainly of a collagen fiber network (75% dry weight) along with proteoglycans, glycoproteins, and elastin [5], [6].

The collagen fibers within the menisci have a specific arrangement that contribute directly to the tensile properties of the meniscus tissue (see FIG. 3). A random woven mesh of fibers is present at the surface for low friction articulation with surrounding articular cartilage [7]-[9]. There is also a superficial network of radial fibers further from the center layer than the random woven mesh. Circumferentially oriented fibers in the deep layers of the meniscus follow the peripheral border and extend beyond the meniscal horns to form the ligamentous attachments to the tibia [10], [11]. These circumferential fibers allow the meniscus to withstand tensile hoop stresses that develop in the tissue under compressive loading. There are also radially oriented "tie" fibers interspersed between circumferential fibers that provide the meniscal tissue with structural integrity and prevent splitting of circumferential fibers [12].

The menisci withstand tensile, compressive, and shear forces and have various roles within the knee joint such as joint stability, shock absorption, joint lubrication, load bearing, and chondroprotection by distributing loads over a broad area of articular cartilage [7], [13]-[16]. The primary function of the menisci is to redistribute the axial compressive load from the femur across the tibial plateau. Due to the wedge shape of the meniscus, it extrudes radially under compressive force. This extrusion is prevented by the circumferential fibers and their ligamentous attachments at the horns, which develop tensile hoop stresses to resist the radial displacement, as shown in FIG. 4-[19].

There are two types of meniscal lesions: acute/traumatic tears from forced movement of the knee joint and chronic/degenerative tears from deterioration of tissue due to aging. Traumatic tears occur from sharp movements and actions of great force, and usually occur in younger people [23]. The symptoms associated with meniscal injury include pain, mechanical impairment, tenderness, and swelling in the knee joint area [24]. In addition to the symptoms associated with the initial injury, osteoarthritis can develop due to meniscal pathology or after a meniscectomy, which is the surgical removal of all or part of the meniscus [25], [26]. Once the meniscus is torn or damaged, its chondroprotective function is compromised, which leads to the progression of osteoarthritis [27]. There are many different types of meniscal tears and they can be classified by location, thickness, depth, and pattern [28]. Some common tear patterns include longitudinal/bucket handle, oblique, radial/transverse, horizontal, and complex (see FIG. 5) [29]. The location of the tear is important for their ability to heal, since only tears in vascularized regions have healing capabilities [30].

Meniscal lesions or tears are one of the most common injuries of the knee, with 15% of all knee injuries involving one or both menisci and around 850,000 meniscal injury related surgeries occurring in the USA annually [31]-[33]. Due to western culture's growing desire to stay active even at a high age, the number of meniscus related injuries continues to grow. The rates of hospital admission after meniscal injury is 0.35-0.7 per 1000 person-years, and this incidence is even higher for active US military service men at 8.27 per 1000 person-years [34]-[36].

Surgical repair on the meniscus following a tear can be achieved arthroscopically using sutures, staples, anchors, or similar methods, as shown in FIG. 6, [38]. There are many factors that come into play when assessing whether a meniscus tear can heal via repair or not including the type of tear, its location, the age of the patient, and various other factors. [39]. The criteria for meniscal tear repair are limited due to the nature of meniscus tissue, since only 10% to 30% of the tissue is vascularized and can heal [40]. For this reason, only 3-5% of tears are currently considered for repair [41].

A meniscal tear can be treated by partial removal of the portion of the meniscus containing the tear (see FIG. 6) or total removal of the meniscus, both of which are referred to as a meniscectomy. With an annual incidence of meniscal legions in the USA being 66 per 100,000 inhabitants, 61 of them result in meniscectomy [42], [43]. It is the most common treatment for meniscus injuries since menisci can only be repaired if the injury is in the peripheral vascularized region. Although they are a common treatment due to the disappearance of pain and impairment, meniscectomies can cause joint space narrowing, femoral condyle flattening, and ridge formation due to an increase in the contact stresses from the femur onto the tibial plateau [44]. These contact stresses increase proportionally with the amount of meniscus tissue removed and can increase by up to 235% due to the approximately 75% reduction in contact area on the tibial plateau following a meniscectomy (see FIG. 7) [45]-[47]. The changes in contact stress distribution has also been suggested to lead to the progression of osteoarthritis in the joint and a direct relation between resection of the meniscus and the risk to develop radiographic osteoarthritis has been established [48]-[51]. Studies have shown that over 20% of patients that have undergone meniscectomy procedure show radiological articular cartilage degeneration within 5 years, and that number gets even greater with time [7], [52].

Patients that undergo multiple partial resections or have very severe tears may require a (sub)total meniscectomy or a complete removal of the damaged meniscus. To relieve pain and prevent advanced osteoarthritis in these patients, meniscal allografts can be implanted to replace the removed meniscus. Although a meniscal allograft is currently the best available treatment for patients with symptomatic meniscectomies, problems associated with this treatment still exist. A meta-analysis of 44 trials representing 1136 grafts was analyzed by ElAttar et al and demonstrated a short to medium term complication rate of 21.3% in a mean follow-up of 4.6 years, the most common complication being a secondary tear [54]. Allografts are known to shrink and undergo collagen remodeling after transplantation, which can compromise their mechanical strength. In addition, problems related to allograft availability, size matching, high cost, and disease transmission prevent this treatment method from being practiced more frequently [33], [55], [56].

SUMMARY

Disclosed herein are embodiments of an artificial meniscus that address the shortcomings of conventional devices and surgical techniques. Methods of making and implanting the artificial menisci are also disclosed herein. An artificial meniscus includes a peripheral edge, an interior edge, anterior and posterior horns, an inferior surface, and a superior surface. The artificial menisci further include a polymer material, at least one circumferential fiber bundle, and at least one non-circumferential fiber bundle. The at least one circumferential fiber bundle and the at least one non-circumferential fiber bundle are each embedded in the polymer material. The non-circumferential fiber bundle is fully encapsulated within the polymer material, and the circumferential fiber bundle extends out of anterior and posterior horns of the artificial meniscus, terminating in ends that are configured for fixation to bone.

Some embodiments of an artificial meniscus include multiple circumferential fiber bundles spaced from each other in the Z-direction. The multiple circumferential fiber bundles spaced from each other in the Z-direction can be positioned adjacent to the peripheral edge of the artificial meniscus. Furthermore, some embodiments can include multiple circumferential fiber bundles spaced between the peripheral and interior edges of the artificial meniscus. The multiple circumferential fiber bundles can converge as they approach the anterior and posterior horns. In some embodiments, the combined ultimate tensile strength of the at least one circumferential fiber bundle is at least 12 MPa.

In some embodiments, the at least one non-circumferential fiber bundle extends in a radial direction. The radially extending, non-circumferential fiber bundles can be spaced across the artificial meniscus between the anterior horn and the posterior horn. In some embodiments, the at least one radially extending, non-circumferential fiber bundle extends back and forth in an at least partially curved line from positions near the peripheral surface of the artificial meniscus to positions near the interior surface of the artificial meniscus. The curving non-circumferential fiber bundle can curve continuously between a first end and a second end, or the curving non-circumferential fiber bundle can alternate between curved segments near the peripheral and interior surfaces of the artificial meniscus and straight segments between the peripheral and interior surfaces of the artificial meniscus.

In some embodiments, the non-circumferential fiber bundles of the artificial meniscus are spaced from each other in the Z-direction. In some embodiments, the at least one non-circumferential fiber bundle is positioned adjacent a superior surface or an inferior surface of the artificial meniscus, and the non-circumferential fiber bundle follows the curvature of the adjacent superior or inferior surface. In some embodiments, the at least one non-circumferential fiber bundle is part of woven sheet of fiber bundles. In some embodiments, the combined ultimate tensile strength of the at least one non-circumferential fiber is at least 1 MPa.

In some embodiments, the artificial meniscus can sustain at least 100N of tensile load for 1000 cycles under cyclic tension testing without altering the ultimate tensile strength or tensile modulus. The artificial meniscus can have a compressive modulus of less than 100 MPa, and a shear strength of at least 0.75 MPa. In some embodiments, the artificial meniscus has a fiber tear out strength of at least 140 Newtons.

In some embodiments, the polymer material is a uniform, continuous structure surrounding the at least one circumferential fiber bundle and the at least one non-circumferential fiber bundle, both of which can be made of a synthetic material. The polymer material can penetrate individual fibers of the circumferential and non-circumferential fiber bundles. The polymer material can be a hydrogel. In some embodiments, the polymer material can be a hydrogel that is at least 20% water by weight.

Methods of implanting artificial menisci are also disclosed herein. The methods include threading a first end of the circumferential fiber bundle extending from the anterior horn through a first bone tunnel, threading a second end of the circumferential fiber bundle extending from the posterior horn through a second bone tunnel, and immobilizing the first and second ends of the circumferential fiber bundles with respect to an adjacent bone Immobilizing the first and second ends of the circumferential fiber bundle can be performed by tying the first and second ends to each other, affixing each of the first and second ends to a button-like structure, or affixing each of the first and second ends to an interference screw, for example.

Methods of making a meniscus-shaped article are also disclosed herein. The methods can include: partially encapsulating at least one circumferential fiber bundle in a first bulk polymer precursor while allowing ends of the at least one circumferential fiber bundle to exit the first bulk polymer precursor; setting the first bulk polymer precursor, thereby forming a first intermediate component of the meniscus-shaped article; fully encapsulating at least one non-circumferential bundle into a second bulk polymer precursor such that all ends of the non-circumferential fiber bundle are covered by the second bulk polymer precursor; setting the second bulk polymer precursor, thereby forming a second intermediate component of the meniscus-shaped article; arranging the first and second intermediate components within a meniscus-shaped mold; surrounding the first and second intermediate components with a third bulk polymer precursor within the meniscus-shaped mold; and setting the third bulk polymer precursor, thereby forming the meniscus-shaped article.

In some embodiments, setting the first bulk polymer precursor further includes forming the first intermediate component in a curved shape prior to arranging the first intermediate component within the meniscus-shaped mold. In some embodiments, setting the second bulk polymer precursor further comprises forming the second intermediate component in the shape of a sheet prior to arranging the second intermediate component within the meniscus-shaped mold.

In some embodiments, the material of the first bulk polymer precursor, the second bulk polymer precursor, and the third bulk polymer precursor can be the same. Setting of the first bulk polymer precursor, the second bulk polymer precursor, and the third bulk polymer can be accomplished by freeze-thaw cycling.

Some embodiments of the method of making a meniscus shaped article can include layering a bottom layer of bulk polymer precursor into the meniscus-shaped mold prior to arranging the first and/or second intermediate components. The bottom layer of bulk polymer precursor can be set prior to arranging the first and/or second intermediate components. The bottom layer of bulk polymer precursor can be the same material as the first bulk polymer precursor, the second bulk polymer precursor, and the third bulk polymer precursor, in some embodiments.

Some embodiments of the method of making a meniscus shaped article can include layering a top layer of bulk polymer precursor into the meniscus-shaped mold after arranging the first and/or second intermediate components. The top layer of bulk polymer precursor can be, in some embodiments, the third bulk polymer precursor. Alternatively, the top layer of bulk polymer precursor can be separate from the third bulk polymer precursor, and the method further comprises setting the top layer of bulk polymer precursor. In some embodiments, the top layer of bulk polymer precursor is the same material as the first bulk polymer precursor, the second bulk polymer precursor, and the third bulk polymer precursor.

DESCRIPTION OF DRAWINGS

The device is explained in even greater detail in the following drawings. The drawings are merely exemplary to illustrate the structure of garments and certain features that may be used singularly or in combination with other features. The drawings are not necessarily drawn to scale.

FIG. 3 shows the collagen fiber structure of the meniscus. A random network is at the surface while circumferential and radial fibers are in the deeper tissue layers. [21]

FIGS. 4A-B shows the loading of the meniscus from the side (a) and from above showing hoop stress development in orange and radial displacement in purple (b). [22]

FIGS. 5A-G show meniscal tear patterns. The healthy meniscus (a) can experience complex/degenerative (b), oblique (c), radial (d), horizontal (e), and longitudinal (f) tears. A longitudinal tear passing through the entire thickness results in a bucket-handle tear (g). [20]

FIG. 6 shows treatment options for meniscal tears. Part of the meniscus is removed (meniscectomy) when the tear is in the white zone (left). Tears in the red zone can usually be repaired and heal (right). [53]

FIGS. 7A-B shows the contact stress on the tibial plateau for an intact knee (A) is concentrated over a smaller area and increases in magnitude following a meniscectomy (B). [7]

FIG. 8 shows a conventional polyethylene-reinforced PVA hydrogel implant after implantation into a sheep knee [68]. Delamination of the composite (left) and implant extrusion with bone tunnel widening (right) occurred during the study.

FIGS. 9A-B shows a CMI® implant (A) for medial and lateral menisci and MR image of the implant (B) showing shrinkage after implantation (white arrow). [33]

FIGS. 10A-B show the medial and lateral Actifit® Implants (A) and an MRI image after implantation (B) showing an oedema-like signal (black arrow) compared to the natural meniscus (white arrow). [33]

FIG. 11 shows the NUsurface® meniscus implant [33].

FIG. 12A shows a top down view of an embodiment of an artificial meniscus.

FIG. 12B shows a top down, cross sectional view of an embodiment of an artificial meniscus, showing the circumferential fiber bundles.

FIG. 12C shows a top down, cross sectional view of an embodiment of an artificial meniscus, showing the non-circumferential fiber bundles.

FIGS. 17A-17G show steps of a processing method for the fabrication of a meniscus-shaped article.

FIGS. 22A-22G shows an example of a prototype molding process. Meniscus model (A) used to dimension CAD model (B) and make mold with holes in the base (C). Fiber bundles were aligned on nails, covered with hydrogel (D), and then freeze/thaw cycled and trimmed (E). Mold was filled with hydrogel, composite fiber mat was pressed on top (F), then mold was covered and clamped (G).

FIGS. 28A-28C shows a fiber tear out test setup with two-piece testing apparatus and prototype test sample before (A) and after (B) sample is inserted. The apparatus is assembled and clamped before mounting in testing machine (C).

FIGS. 29A-29B show a CAD model of fiber tear out apparatus. The mold section (A) has curvature to simulate the femur and the cover section (B) is flat to simulate the tibia. The areas where fibers exit are cleared of interfering walls, outline in red.

FIGS. 30A-30E show a process of making a PVA model-shaped prototype. The model meniscus (A) is scanned to get 3D mesh (B), which is converted to solid CAD model (C) to create a mold to 3D print (D). The PVA prototype (E) is then created.

FIG. 31 shows a knee model with original model meniscus (#1 from Table 6) mounted in the mechanical testing machine for compression. Most of the ligaments on the model were removed.

FIG. 32 shows a model meniscus (#1 from Table 6) before (left) and after (right) insertion into the knee model. The protrusion and slot used for insertion are emphasized with red circles.

FIG. 33 shows the lateral side of the model meniscus after removal of the medial portion (left) that was used for the medial meniscectomy (#2 from Table 6) test condition (right).

FIG. 34 shows the unreinforced, model-shaped PVA meniscus (#3 from Table 6) before (left) and after (right) insertion into the knee model.

FIG. 35 shows an unattached composite model-shaped meniscus (#4 from Table 6) after insertion into the knee model and pressure indicating film placement.

FIGS. 36A-36C show the attachment of the composite model-shaped meniscus (#5 from Table 6). The extending fibers are threaded through bone tunnels in the anterior (A) and posterior areas of the knee model's tibia and tied tightly together on the side (C).

FIGS. 37A-37C are the matched shape, #6 from Table 6 (A), and generic shape, #7 from Table 6 (B), prototypes designed in CAD software, and their attachment in the knee model with the use of the model's lateral meniscus (C).

DETAILED DESCRIPTION

Figure 1:
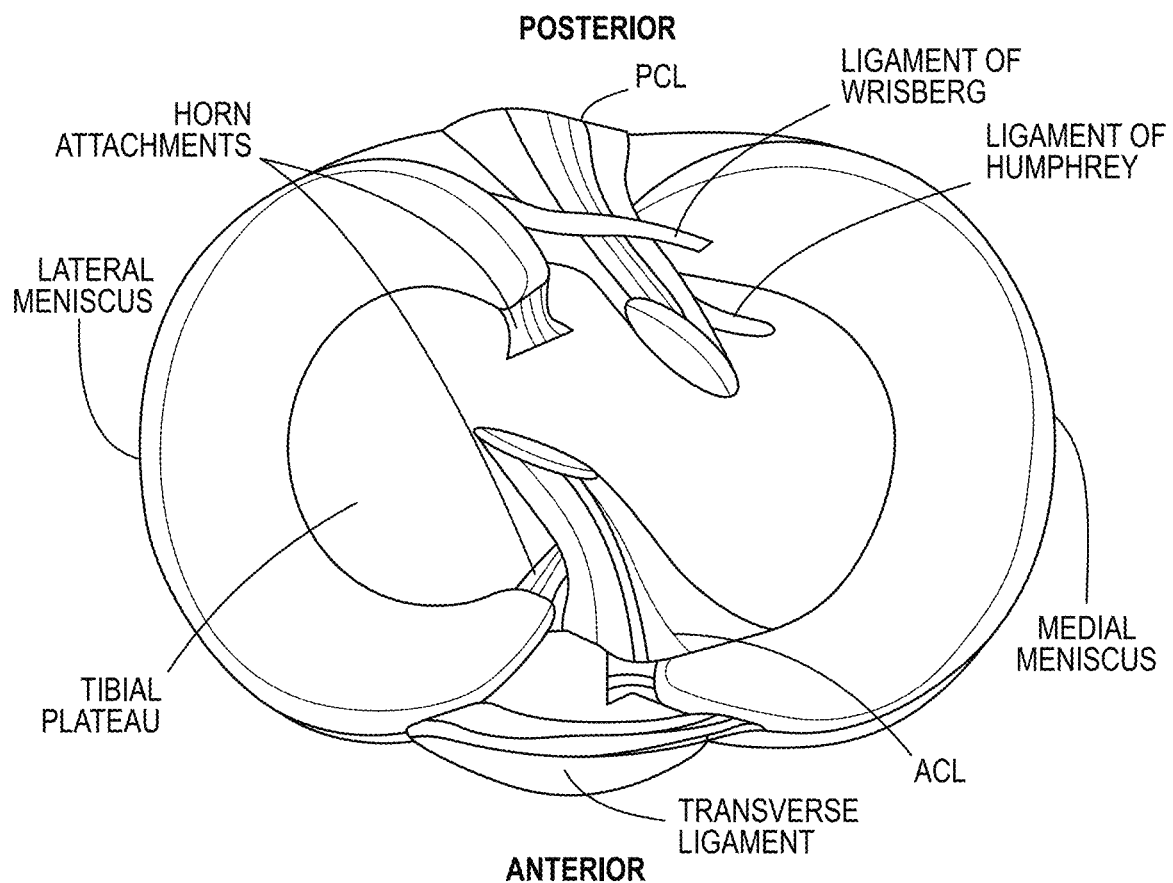
FIG. 1 shows the menisci and their anterior and posterior horn attachments. Also shown are associated ligaments within the knee joint. [20]
Figure 2:
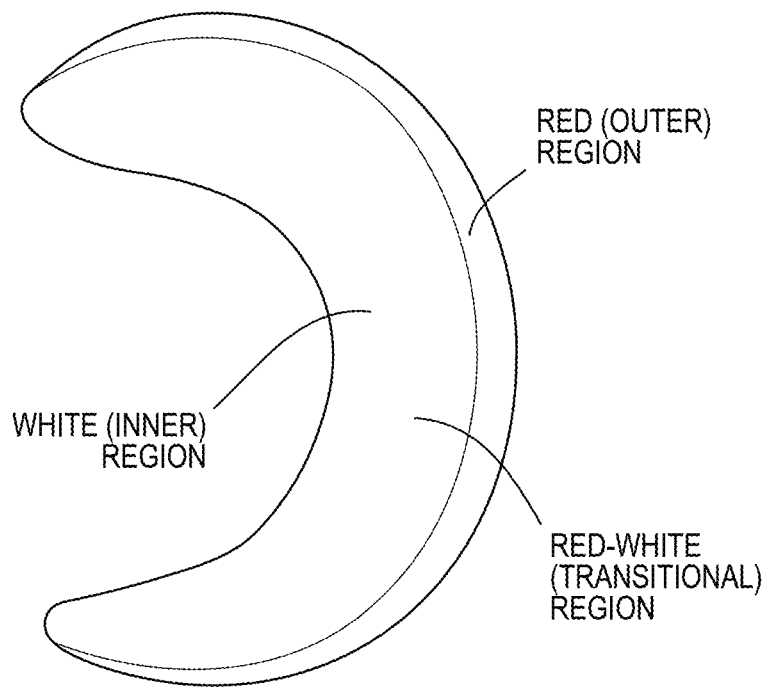
FIG. 2 shows the vascularization of the meniscus. The peripheral red region has vasculature and nerves and the central white region does not. [20]

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The term "subject" is defined herein to include animals such as mammals, including, but not limited to, primates (e.g., humans), cows, sheep, goats, horses, dogs, cats, rabbits, rats, mice and the like. In some embodiments, the subject is a human A potential solution to the problems with current treatment would be an implantable meniscal substitute. No such treatment is presently available to patients or FDA approved. Various types of substitutes have been used in experimental and clinical studies including biodegradable scaffolds, permanent synthetic scaffolds, collagen, and completely artificial implants. Current research seems to mainly focus on tissue engineering approaches, but with limited success [33], [57].

Some of the earliest attempts of producing a meniscus substitute utilized Teflon and Dacron biomaterials as permanent meniscus replacement materials. However, the material properties of these materials were not suitable for this high-load application and resulted in deformation of the implant and wear particle deposition after testing in a rabbit model [27], [58], [59].

Another substitute that has been researched involves a polyglycolic acid fiber scaffold that is reinforced with poly (lactic-co-glycolic acid) and seeded with allogenic meniscus cells. The scaffold regenerated meniscus-like tissue after implantation into rabbits for 10 weeks, but further analysis of the tissue revealed a significantly decreased modulus value compared to natural tissue [60].

A porous scaffold with a hyaluronic acid and polycaprolactone matrix reinforced with circumferential ploy-lactic acid fibers has also been investigated. These implants allowed fibrocartilage tissue ingrowth like the make-up of natural meniscus tissue, and showed little to no signs of cartilage damage in a one-year sheep study. However, implant extrusion out of the joint space was an issue in most cases, and a more rigid fixation to prevent this extrusion lead to dislocation and implant failure [61], [62].

Polyvinyl alcohol (PVA) hydrogel was one of the first non-scaffold, permanent implants to have been studied for use as a meniscus replacement, and multiple groups have investigated this approach. Early studies by Kobayashi et al. demonstrated the usefulness of the material by showing that its compressive properties and viscoelastic behaviour were very similar to that of the natural meniscus, with no implant fracture or degradation of properties observed after implantation into a rabbit knee for 2 years [63], [64]. Although the non-reinforced implant had sufficient strength for a rabbit meniscal replacement, it failed from radial tears and caused cartilage damage when exposed to the higher force environment of a sheep knee. These failures would likely translate to a human knee since the joint forces are also large.

Another group evaluated the PVA hydrogel implant in a sheep model. Complete radial tears were observed in the posterior horns of all implants and the implants caused severe damage to the articular cartilage after one year. The authors speculated that size mismatch, inadequate fixation, or structural composition of the implant body could have caused these failures [65].

More recently, polyethylene fiber-reinforced PVA hydrogel implants have been investigated. Holloway et al. showed that incorporation of fibers into the hydrogel matrix can allow tuning of the compressive and tensile moduli to resemble that of the natural meniscus [66]. This group focused on mechanical properties such as the tensile and compressive elastic moduli, the interfacial strength of the composite, and the pressure distribution when loaded in a knee joint. They did not assess the overall strength of the composite material. Since delamination of the hydrophobic fibers from the hydrogel matrix was an initial concern, they also showed that surface modification of the fibers increased the interfacial strength of the composite [67]. A 4-month sheep study was conducted on implants with polyethylene fiber mats used as the reinforcement, but delamination of the implant still occurred along with implant extrusion and bone tunnel widening (see FIG. 8) [68]. The bone tunnel widening may be attributed to the attachment method used, and the attachment method could have also caused some of the extrusion. The delamination issue, and potentially some of the extrusion, can be attributed to several other factors.

The polyethylene fibers Holloway et al. used as reinforcements were hydrophobic and required surface modification to provide good adhesion to the hydrogel matrix. As evidenced by the sheep study, this interfacial adhesion improvement was still insufficient and delamination occurred. The artificial meniscus disclosed herein can utilize hydrophilic fibers (for example, aramid fibers) to absorb water and adhere to a hydrogel matrix without the need for modification. The tensile, compression, and fiber tear out tests performed on the composite material, described in the Examples, shows that the interface can withstand the high stresses and loads that a meniscus implant would experience in the knee joint after meniscus replacement. Therefore, the risk for delamination after implantation is reduced compared to the polyethylene reinforced implant.

In addition to the differences in fiber interaction with water, the fiber and reinforcement layout used in the artificial meniscus disclosed herein is different from the reinforcement layout used in the implant developed by Holloway et al. The polyethylene reinforced implant used fiber mats, with no specific orientation, to reinforce the hydrogel matrix. While some embodiments of the artificial meniscus disclosed herein also use a fiber weave as a base reinforcement, the weave is fully encased in hydrogel which reduces the risk for delamination. The implant also has specifically oriented fiber bundles around its periphery that help convert compressive load to tensile hoop stress and limit radial deformation and subsequent extrusion. This specific fiber orientation and overall reinforcement layout gives the implant strength in all directions and gives the implant enhanced strength in the crucial area around the periphery to prevent extrusion. The fibers being fully encased in hydrogel around the outer periphery also reduces the risk of fiber delamination, especially since the fibers would be pulled toward the bulk of the hydrogel instead of toward the surface during normal loading and use. The fibers also have more surface area in direct contact with the hydrogel than a weave would, which improves interfacial adhesion between the hydrogel and reinforcements.

There are currently two partial and one total meniscal substitute clinically available. The two partial substitutes are both porous, resorbable implants that stimulate tissue generation and require an intact peripheral meniscal rim, one being made from collagen (CMI®) and the other made from polyurethane (Actifit®). These partial substitutes are not fixed to the bone. The total substitute is a permanent implant with no bioactivity and is made from polyethylene reinforced polycarbonate urethane (NUsurface®). The NUsurface implant is not fixed to bone. Each of these implants have shown promise, but also have their own sets of problems [33].

The collagen meniscus implant (CMI®, FIG. 9) is made up of bovine type I collagen fibers with glycosaminoglycans and requires the meniscal rim to be intact due to poor mechanical properties and fixation of the scaffold alone [69], [70]. Initially, animal studies demonstrated its safety and ability to regenerate tissue that resembled the meniscus [71]. A clinical study of over 300 patients confirmed the implant's ability to regenerate tissue that resembled the meniscus, but there were no significant improvements in clinical scores compared to the meniscectomy group and the tissue was not pure fibrocartilage but instead a hybrid-type tissue [69]. Another study reported improved clinical scores in the implant group, but again the regenerated tissue was unlike the native meniscus and the mechanisms behind the regeneration process is unclear. In addition, shrinkage and extrusion of the implant was observed during follow-up and persistent pain was noted in 12% of patients [72]-[76].

The porous polyurethane scaffold that makes up the Actifit® implant (FIG. 10) was initially studied for use as a total meniscus replacement. It was intended to promote tissue infiltration and differentiation into fibrocartilage, like the tissue that makes up the natural meniscus. A two-year study of the total replacement in dogs showed evidence of tissue ingrowth and produced a structure with similar compressive properties to the natural meniscus, but the collagen orientation was different from the meniscus and the construct was unable to resist the shear forces in the knee joint. These issues could have been the reason the implant was unable to prevent cartilage damage to the joint. Fragmentation in almost all the implants was also reported after 24 months [77], [78]. Based on these results, the implant was considered best suited as a partial replacement.

A partial replacement of the scaffold was implanted into a bovine meniscal defect and promoted fibrous tissue growth without damaging the surrounding cartilage. In addition, the Actifit® implant helped improve the contact mechanics on the tibia when compared to the defect condition [79], [80]. The implant was also used in human partial meniscectomy knees with a follow up of 24 months. Pain reduction and improved functionality was observed after 6 months due to regeneration of tissue, and 90% of patients demonstrated improved cartilage condition and joint stabilization up to 24 months, but it is important to note that this study did not include a meniscectomy control group for comparison [81]. Another study evaluated patients at a mean of 19 months and showed no progression of osteoarthritis and good structural integrity of the implant, but the tissue gave an oedema-like signal when assessed using MRI as opposed to fibrocartilage tissue [75]. A more recent human study evaluated 67 implanted scaffolds, with 25% needing removal at a mean of 22 months due to implant extrusion or persisting pain. The total survivorship was only 63.6% at 6 years follow up [82].

Unlike most of the other meniscal replacements in development, NUSurface® from Active Implants (FIG. 11) is a non-degradable polycarbonate urethane total replacement reinforced with polyethylene fibers that was evaluated initially for biomechanical performance as opposed to biological response. During its development, the free-floating implant was computationally optimized by changing its shape and arrangement of reinforcing fibers to assess pressure distribution and contact area during simulated loading on the tibial plateau, and then the design was validated using cadaver knees [83]. The tests showed comparable contact areas to the native meniscus, but noticeably different distributions. The implant has also been evaluated for viscoelastic properties and the effects of loading the implant on cartilage vitality in vitro [84], [85]. A sheep study revealed no signs of wear or changes in structural properties of the implant, but slight cartilage damage was observed after 6 months, along with various minor complications [86]. Clinical data is scarce for the implant since it only recently entered clinical trials. One update reports that 19 of 41 implants (46%) had to be removed 2 to 26 months after operation due to either radial tears, dislocation, persistent pain, improper sizing, or synovitis/wear particles. In all, the previous issues or other minor complications occurred in 32 of the implants [82].

The artificial meniscus of the present disclosure will now be described. All directional and orientation terminology refer to a patient in a standing position. Orientation with respect to the artificial meniscus embodiments disclosed herein will include such terms as peripheral, interior, anterior, posterior, inferior, and superior. The anatomical term "anterior" means the feature in question is designed to be positioned adjacent to the front side of the subject's body. Reference is made to the artificial meniscus 2 of FIG. 12A to demonstrate the positioning of the various anatomical terminology. For example, the anterior horn 4 will be positioned such that it is adjacent to the patella on the front side of the subject's knee. Conversely, the anatomical term "posterior" means the feature in question is designed to be positioned adjacent to the rear side of the subject's body. For example, the posterior horn 6 will be positioned such that it is farther from the patella than the anterior horn. A vertical axis (also referred to herein as the Z-axis) can be visualized extending superiorly from the inferior surface 16. For reference, anterior and posterior horn axes, A-A and P-P can be visualized extending perpendicularly to the Z-axis, through the center of (and at a normal to) the respective anterior horn surface 8 and posterior horn surface 10, as shown in FIG. 12A.

The peripheral edge, or peripheral surface 12 of an artificial meniscus 2 refers to the side that, when viewing the relatively C-shaped structure from a top-down perspective, extends along the outside of the C-shape, between the anterior horn axis A-A and the posterior horn axis P-P. Conversely, the interior edge, or interior surface 14 of an artificial meniscus 2 indicates the side that, when viewing the relatively C-shaped structure from a top-down perspective, extends along the inside of the C-shape, between the anterior horn axis A-A and the posterior horn axis P-P. References to the width, w, of the artificial meniscus indicate a horizontal measurement between the peripheral surface 12 and the interior surface 14 (extending from a point on the interior surface 14 across the shortest distance possible to an oppositely positioned point on the peripheral surface 12, that is, extending along a normal line to the curve of the interior surface 14 across to an oppositely positioned point on the peripheral surface 12). The width of the artificial meniscus can vary depending upon the anterior to posterior positioning of the point of measurement, as well as the inferior to superior positioning of the point of measurement. The "radial" direction indicates a direction extending away from the center of convergence of all widths that extend between the peripheral surface 12 and the interior surface 14. For example, the non-circumferential fibers 28 shown in FIG. 12C extend in radial directions.

Figure 13A:
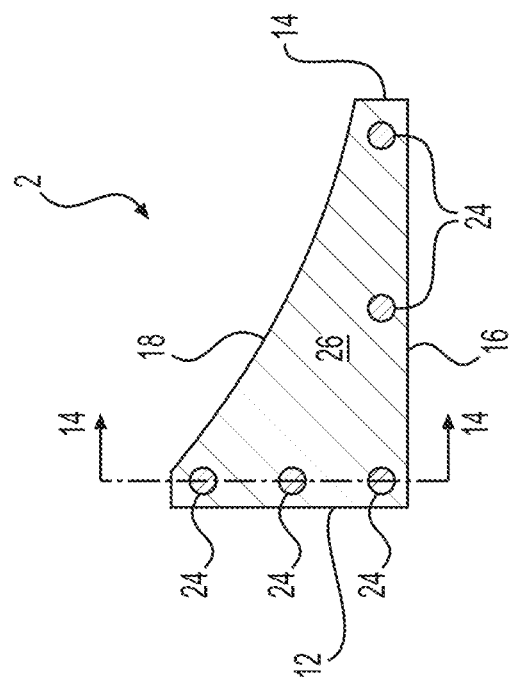
FIG. 13A shows a side cross sectional view across a width of an embodiment of an artificial meniscus.

Reference is now made to FIG. 13A to describe additional anatomical terminology used herein to describe embodiments of artificial meniscus 2. The terms "inferior" and "superior" indicate orientations in the vertical direction. An inferior side, inferior edge, or inferior surface 16 of artificial meniscus 2 is lower than the superior side, superior edge, or superior surface 18 of artificial meniscus 2, for example. References to the height, h, of the artificial meniscus indicate a vertical measurement between the inferior and superior surfaces. The height of the artificial meniscus may vary depending upon the peripheral to interior positioning of the point of measurement, as well as the anterior to posterior positioning of the point of measurement. Again, all directional and orientation terminology refer to a patient in a standing position.

The artificial meniscus embodiments disclosed herein are generally C-shaped or semi-circular when viewed from a top-down perspective. However, this is not meant to imply any particular degree of symmetry. In fact, the artificial meniscus embodiments disclosed herein can be slightly asymmetrical (in that the width near one horn can be different than the width near the other horn). In some embodiments, the curve of the peripheral and interior surfaces 12, 14 may extend all the way to tips of anterior and posterior horns 4, 6, such that the entire exterior surface of the artificial meniscus 2 is curved. In other embodiments, the horns 4, 6, may be defined by a somewhat rectangular anterior and posterior horn extensions 20 and 22, as shown in FIG. 12A. The superior surface 18 of the artificial meniscus 2 is generally concave, whereas the inferior surface 16 is relatively flat, as shown in FIG. 13A, or at least less curved than the superior surface 18. Some curvature of the inferior surface 16 may exist on a large or small scale depending upon the particular needs of the implant or subject. The height of meniscus 2 is larger at the peripheral surface 12 than the interior surface 14.

The artificial meniscus embodiments disclosed herein are reinforced by fiber bundles 24, 28 that extend within the polymer material 26 of the meniscus 2. Some of the fiber bundles are oriented and aligned so that they can convert the compressive forces into tensile hoop stresses to dissipate the load. To accomplish this, one or more fiber bundles are circumferentially aligned with the peripheral surface 12 or the interior surface 14 of the meniscus 2, as shown in FIG. 12B, to mimic the circumferential collagen fibers in the natural menisci. Advantageously, the ends 32 of the circumferential fiber bundles 24 that are embedded in polymer material 26 extend out of the meniscus 2 at the anterior and posterior horns 4, 6 to provide attachment points for affixing to the bone. Affixing the ends 32 of the circumferential fiber bundles 24 to the bone helps to prevent dislocation from the joint space under load like the ligaments of the native meniscus.

Since the natural meniscus also has interwoven radial fibers to provide structural integrity, the polymer material 26 of the artificial meniscus 2 is provided with one or more non-circumferential fiber bundles 28, as shown in FIG. 12C, to give the implant radial strength. In some embodiments, the non-circumferential fiber bundles 28 are oriented radially, between the peripheral and interior surfaces 12, 14. The non-circumferential fiber bundles could come in the form of a woven sheet 30, as shown in FIG. 17F, that spans across the cross-sectional area of the meniscus 2. This woven sheet 30 would provide strength in all directions and limit implant deformation, as well as provide structural integrity and hold the entire construct together to better avoid tears, ruptures, and any further propagations. Unlike circumferential fiber bundles 24, which extend out of anterior and posterior horns 4, 6, the non-circumferential fiber bundles are fully encapsulated within polymer material 26. Fully encapsulating fiber bundles within the polymer material helps to prevent peeling away of the fibers from the implant.

As shown in FIG. 12B, multiple circumferential fiber bundles 24 can be spaced between the peripheral and interior edges 12, 14 of the artificial meniscus 2. The number of circumferential fiber bundles 24 spaced between the peripheral and interior edges 12, 14, of the artificial meniscus 2 can vary widely, and is not meant to limit the scope of the disclosure. The circumferential fiber bundles 24 can be evenly spaced from one another, or unevenly spaced from one another. In some embodiments, the density of the circumferential fiber bundles 24 in the peripheral to interior direction may increase moving toward or away either the peripheral or interior surfaces 12, 14 of the artificial meniscus. The degree of spacing of the circumferential fiber bundles as they exit the anterior and posterior horns may vary.

The circumferential fiber bundles 24 exit the artificial meniscus 2 at locations adjacent to the anterior and posterior horns. In some embodiments, the multiple circumferential fiber bundles can converge as they approach the anterior and posterior horns 4, 6, of the artificial meniscus, as shown in 12B (that is, the peripheral to interior spacing of the circumferential fiber bundles 24 decreases as the fiber bundles approach the horns). The degree of convergence can vary by embodiment, and in some, the circumferential fiber bundles 24 may maintain a constant degree of spacing as they extend through the meniscus 2 from the anterior horn 4 to the posterior horn 6. Advantageously, at the edges of the meniscus 2, each exiting circumferential fiber is individually encapsulated in polymer material 26 in order to reduce the chance of delamination and fiber pull out. The circumferential fiber bundles 24 are affixed to nearby bone structures or surgical implants. For example, the ends 32 of the circumferential fiber bundle, shown in FIGS. 12B and 17G, may be pulled through a surgically formed bone tunnel, and affixed at the opposite end of the bone tunnel by tying it to a button-like structure, the button-like structure being wider than the bone tunnel and including a loop for stringing the fiber bundle therethrough. Alternatively, or in addition, the circumferential fiber bundles can be affixed to the adjacent bones using interference screws, such as those used in allograft fixation surgeries. In some embodiments, the circumferential fiber bundles may be pulled through separate bone tunnels and knotted directly to each other. FIGS. 19A-19C show ends 32 of the circumferential fiber bundles 24 being tied together around a bone model.

Figure 13B:
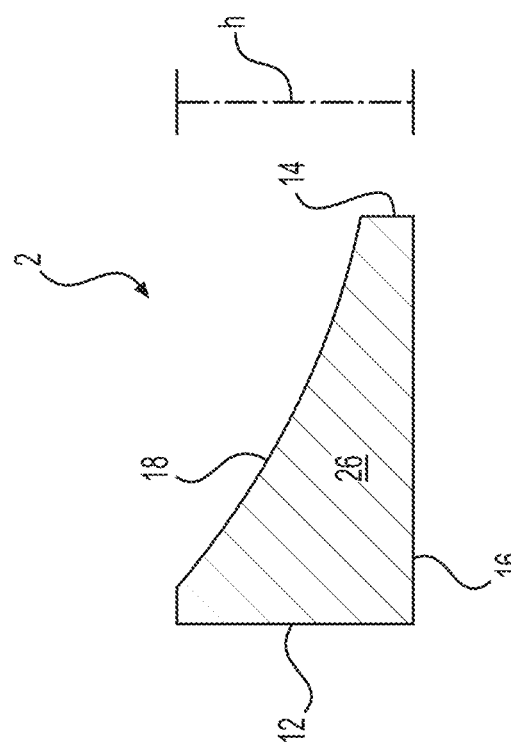
FIG. 13B shows a side cross sectional view across a width of an embodiment of an artificial meniscus, showing the circumferential fiber bundles.
Figure 14:
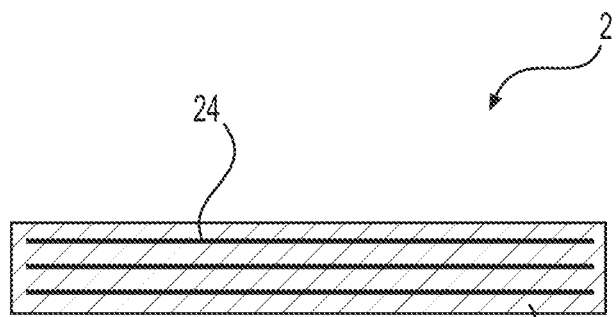
FIG. 14 shows a peripheral side cross sectional view of an embodiment of an artificial meniscus, showing the circumferential fiber bundles.

In addition to spacing multiple circumferential fibers 24 in the peripheral to interior direction, multiple circumferential fiber bundles 24 can be spaced from each other in the Z-direction. This may be especially advantageous near the peripheral surface 12, as shown in FIG. 13B, to provide additional reinforcements for converting compressive forces into tensile hoop stresses to dissipate the load and reduce radial extrusion across the height of the implant. The number of circumferential fiber bundles spaced between the inferior and superior surfaces of the artificial meniscus can vary widely, and is not meant to limit the scope of the disclosure. The circumferential fiber bundles 24 can be evenly spaced from one another in the Z-direction, or unevenly spaced from one another. In some embodiments, the density of the circumferential fiber bundles 24 in the Z-direction may increase moving toward or away either the inferior surface 16 or superior surface 18 of the artificial meniscus 2. In some embodiments, the outermost (most peripherally positioned) circumferential fiber bundle or bundles 24 are on, adjacent to, or immediately interior to the peripheral surface 12 (positioned just far enough into the artificial meniscus 2 to allow the fibers to be penetrated by the polymer material 26). As such, the polymer filled fibers are palpable and visible from the peripheral surface 12 of the artificial meniscus, as shown in FIG. 14. This positioning of the circumferential fiber bundle or bundles facilitates distribution of hoop stress throughout the implant and reduces radial extrusion across the height of the implant.

In some embodiments, the combined ultimate tensile strength of the at least one circumferential fiber bundle 24 is at least 12 MPa. Although the ultimate tensile strength of natural, anisotropic meniscal tissue varies by region, the mean maximum stress within the meniscus has been found to be 18.8 MPa for lateral and 17.6 MPa for medial menisci circumferentially. Therefore, in some embodiments, the artificial meniscus 2 will have an ultimate circumferential tensile strength of at least 12 MPa so that it is able to withstand the same maximum stresses as a natural meniscus, which is a parameter almost all previous developers of artificial meniscus implants have failed to address. The circumferential tensile stress value should be taken from a sample that would be circumferentially oriented around the periphery of the implant, since that is where the tensile hoop stresses develop during loading to resist radial deformation. The ultimate circumferential tensile strength is additive in that each circumferential fiber bundle contributes a fraction of the combined measurement. For example, ten evenly sized circumferential fiber bundles (of equivalent materials and densities) might give an ultimate circumferential tensile strength of 20 MPa. In that scenario, each bundle might contribute to 2 MPa of the ultimate circumferential tensile strength. Of course, the individual contributions to the ultimate stress measurement may vary if the sizes, materials, or other properties vary between fiber bundles.

The tensile modulus of the natural meniscus can vary on location between about 50 MPa to 300 MPa circumferentially. Therefore, in some embodiments, the artificial meniscus 2 has a tensile modulus is at least 50 MPa in the circumferential direction to limit deformation and extrusion.

The artificial meniscus embodiments also include one or more non-circumferential fiber bundles 28 extending in non-circumferential directions. In some embodiments, such as the one shown in FIG. 12C, multiple non-circumferential fiber bundles 28 extend in a radial direction, from a position adjacent the interior surface 14 to a position adjacent the peripheral surface 12. The radially extending, non-circumferential fiber bundles 28 can be spaced across the artificial meniscus 2 between the anterior horn 4 and the posterior horn 6. The number of radially extending non-circumferential fiber bundles 28 spaced from each other between the anterior horn 4 and the posterior horn 6 can vary widely, and is not meant to limit the scope of the disclosure. The radially extending non-circumferential fiber bundles 28 can be evenly spaced from one another, or unevenly spaced from one another. In some embodiments, the density of the circumferential fibers may vary. For example, the density of radially extending non-circumferential fiber bundles may be higher (i.e., the measured distance between fibers may be lower) at a position adjacent to the posterior horn 6 than the anterior horn 4. Increased density of radially extending non-circumferential fiber bundles 28 near the posterior horn 6 advantageously mimics the distribution of strengths of the intact meniscus. Furthermore, increased density of radially extending non-circumferential fiber bundles 28 near the posterior horn 6 may also be used to further reinforce and strengthen the posterior region of the implant corresponding to the region the intact meniscus experiences the most tears.

Figure 15:
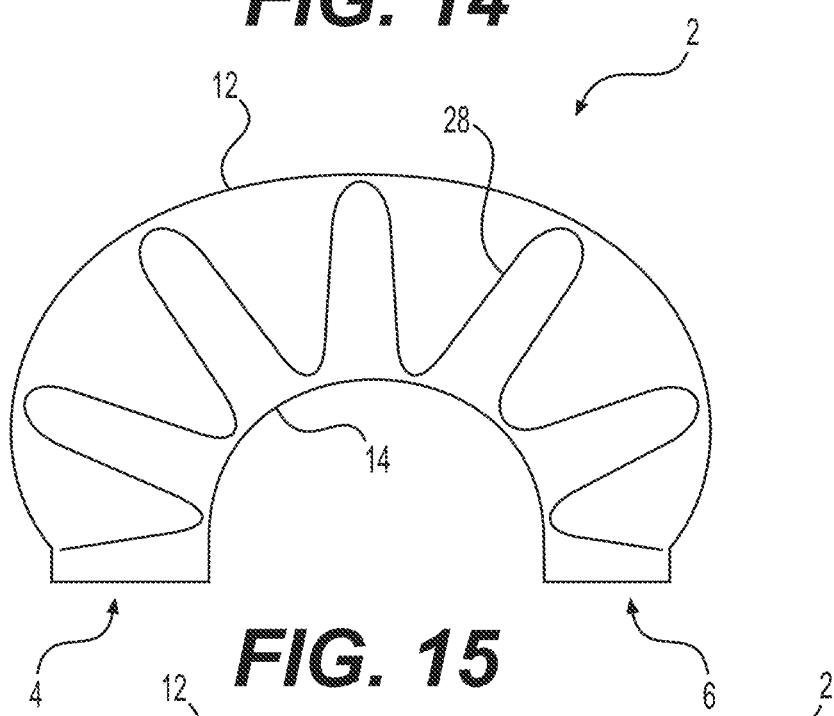
FIG. 15 shows a top down, cross sectional view of an embodiment of an artificial meniscus, showing a non-circumferential fiber bundle.
Figure 16:
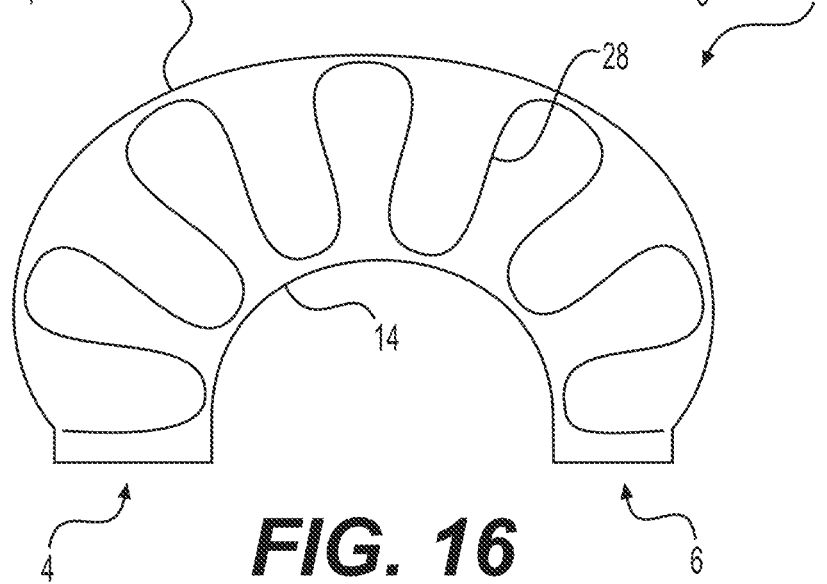
FIG. 16 shows a top down, cross sectional view of an embodiment of an artificial meniscus, showing a non-circumferential fiber bundle.

Some embodiments, such as those shown in FIG. 15 and FIG. 16, may include a single non-circumferential fiber bundle 28 that extends back and forth in an at least partially curved line. The non-circumferential bundle 28 extends from positions near the peripheral edge 12 of the artificial meniscus 2 across the width of the artificial meniscus 2 to positions near the interior edge 14 of the artificial meniscus 2, then back again. The embodiment of FIG. 15 shows a non-circumferential fiber bundle 28 that includes relatively long straight segments extending directly across the width of meniscus 2, curving relatively sharply at positions adjacent to the peripheral edge 12 and the interior edge 14. The embodiment of FIG. 16, by contrast, shows a non-circumferential fiber bundle 28 that spans a longer distance near the peripheral and interior edges 12, 14, curving relatively gently then backtracking over shorter straight segments as it crosses the width of the meniscus 2. In some embodiments, a non-circumferential fiber bundle 28 can curve continuously as it moves back and forth between the peripheral and interior edges 12, 14. Varying patterns of curvature of the non-circumferential fiber bundle 28 are considered to be within the scope of the disclosure, and may have different advantages depending upon the footprint and magnitude of the load they are intended to support.

Figure 13C:
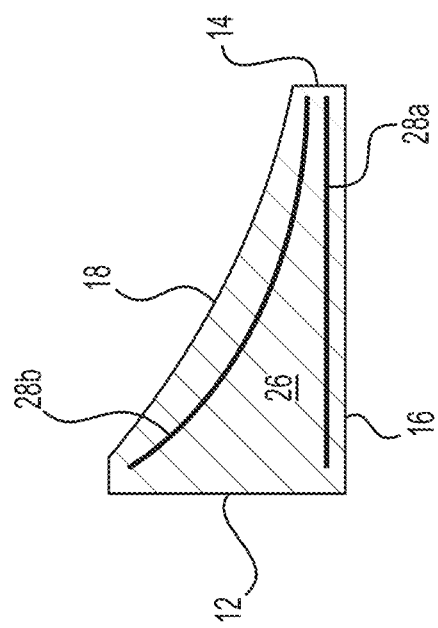
FIG. 13C shows a side cross sectional view across a width of an embodiment of an artificial meniscus, showing the non-circumferential fiber bundles.

Some embodiments of artificial meniscus 2 can include multiple non-circumferential fiber bundles 28 spaced from each other in the Z-direction, as shown in FIG. 13C. The non-circumferential fiber bundles may be oriented horizontally (that is, perpendicularly to the Z-axis), such as the lowermost non-circumferential fiber bundle 28a adjacent inferior surface 16. Alternatively, or in addition, the non-circumferential fibers may be oriented at one or more angles to the inferior surface 16, traveling superiorly as they extend from the interior to the periphery of the artificial meniscus 2. For example, as shown in FIG. 13C, the uppermost non-circumferential fiber bundle 28b, which is positioned adjacent the superior surface 18, extends away from interior surface 14 at an angle, and remains adjacent the superior surface 18 as it curves upward to terminate at a point adjacent both the superior surface 18 and the peripheral surface 12. The number of non-circumferential fiber bundles 28 spaced from each other in the Z-direction (between the inferior and superior surfaces of the artificial meniscus) can vary widely, and is not meant to limit the scope of the disclosure. The non-circumferential fiber bundles can be evenly spaced from one another in the Z-direction, or unevenly spaced from one another. In some embodiments, the density of the circumferential fibers in the Z-direction may increase moving toward or away from either the inferior or superior surfaces 16, 18 of the artificial meniscus 2.

In some embodiments, the non-circumferential fiber bundles 28 are embedded in polymer material 26 as close to the superior surface 18 as possible without substantially increasing friction between the superior surface 18 and the adjacent bone of the subject. The non-circumferential fiber bundle or bundles 28 can follow the curvature of the superior surface. Likewise, inferiorly positioned non-circumferential fiber bundles 28 can be positioned adjacent the inferior surface 16 of the artificial meniscus yet still embedded in the polymer material. The non-circumferential fiber bundles 28 can be embedded within the polymer material 26 as close as possible to the inferior surface 16 without causing an unfavorable amount of friction between the inferior surface and the adjacent bone of the patient, and can follow any curvature of the inferior surface 16, should it exist.

In an alternative embodiment, such as the one shown in FIG. 17F, the non-circumferential fiber bundles can be woven together as part of a larger reinforcement sheet 30. FIG. 17F depicts an intermediate processing step, and will be described in greater detail below. The woven sheet of fibers can be positioned perpendicularly to the Z-axis, or may tilt at an angle angle to the Z-axis. Regardless of the tilt, the reinforcement sheet 30 extends from a peripheral to interior direction across artificial meniscus 2, as well as from an anterior to posterior direction. The direction of the warp and weft of the reinforcement sheet 30 is not critical to the function of the device. In some embodiments, strips of the reinforcement sheet 30 could be cut and laid in a radially spaced arrangement across the width of the meniscus 2. Furthermore, the reinforcement sheet 30 that includes non-circumferential fiber bundles need not necessarily be woven, but could alternatively be a non-woven sheet, a knit sheet 30, or any other textile patterning without veering from the scope of this disclosure.

The combined ultimate tensile strength of the at least one non-circumferential fiber 28 is at least 1 MPa, and, in some embodiments, at least 4 MPa. Although the ultimate tensile strength of natural anisotropic meniscal tissue varies by region, the mean maximum strength of the meniscus has been found to be around 4 MPa radially. The ultimate tensile strength of the non-circumferential fibers 28 is additive in that each non-circumferential fiber bundle contributes a fraction of the combined measurement. For example, ten evenly sized non-circumferential fiber bundles (of equivalent materials and densities) might give an ultimate tensile strength of 6 MPa. In that scenario, each non-circumferential fiber bundle 28 might contribute to 0.6 MPa of the ultimate non-circumferential tensile stress. Of course, the individual contributions to the ultimate tensile strength measurement may vary if the sizes, materials, or other properties vary between fiber bundles.

Then natural tensile modulus in the radial direction can be about 20 to about 70 MPa. As such, the tensile modulus of the implant in the radial direction should be at least 20 MPa to limit deformation and extrusion.

Generally, the polymer material 26 is elastic and relatively soft. A wide range of compressive moduli have been reported for the natural menisci and their values are dependent on strain level, loading rate, and test type. Studies have reported values for the compressive modulus of the human meniscus to be from 0.10 to 0.22 MPa under confined compression while others report modulus values from 0.30 to 1.13 MPa under unconfined compression at a physiologic strain and strain rate [116]-[118]. This means that under an unconfined testing protocol, a meniscal implant material should have a modulus of at least 0.30 MPa in a physiologic strain range. Like the tensile modulus specification, the upper limit for the compressive modulus is not critical since metal materials have been used in spacer devices and have moduli much greater than 1.13 MPa. Therefore, the modulus for a flexible prosthetic meniscus should remain within an order of magnitude of the natural meniscus at less than or equal to 100 MPa.

Tensile loads develop consistently during gait with each step taken, and have been estimated to peak around 50N during simulated motion at the anteromedial meniscal insertion site and about 65N±25 under joint loading in the posterior horn attachment site [114], [115]. Since the meniscus would realistically experience only one of the attachment site maximums, these values indicate a tensile load of about 90N would be a worst-case value for most human individuals. Therefore, the artificial meniscus 2 can sustain at least 100 N of tensile load for 1000 cycles under cyclic tension testing. There should also be no significant changes in ultimate tensile strength or tensile modulus following these cycles.

Shear forces in the natural meniscus can peak at around 60% bodyweight in the posterior direction, especially for high flexion activities or stair climbing [88]. Using a $90^{th}$ percentile body weight of about 110 kg, the corresponding standing joint load of around 1000N puts the medial meniscus contact area at around 420 mm², which is 65% of the total compartment contact area of 640 mm² [88], [121], [122]. Using Equation 1 with the meniscus contact area and 60% body weight load, a high estimated shear stress on the natural meniscus can be calculated to be around 1.4 MPa. This is also an over-exaggeration of the shear force, since it assumes all shear force would be in the meniscus area, when it would realistically be exerted on the entire compartment area. Therefore, to withstand the shear forces experienced by the knee joint of most individuals, the artificial meniscus 2 can have a maximum shear stress of at least 1.4 MPa.

$$\tau_{max} = 0.6 \times \frac{1000 \text{ N Load}}{420 \text{ mm}^2 \text{ Area}} = 1.4 \; MPa \qquad [\text{Equation 1}]$$

The polymer material 26 can be any biocompatible polymer that meets the criteria outlined above. In some embodiments, the polymer material 26 is a hydrogel, such as polyvinylalcohol (PVA) or a PVA copolymer. In some embodiments, the polymer material can be of a single molecular weight of PVA, at a set concentration and number/duration of freeze-thaw cycles used in the setting/curing process. PVA hydrogel properties can vary significantly when these parameters are changed. The number of freeze-thaw cycles has been shown to have little effect on properties after five or six cycles (the number of cycles used in the Examples). The concentration of PVA (or the weight percentage in the initial solution) can impact properties to a greater degree when the hydrogels are subjected to five or more freeze-thaw cycles [66]. Certain embodiments of the polymer material of the artificial meniscus disclosed herein have a higher concentration of PVA than the previous PVA-hydrogel implants, which likely contributes to improved strength and limited deformation.

Alternatively, the polymer material 26 can be a polyurethane material or a polycarbonate material (including co-polymers of polyurethane or polycarbonate). In some embodiments, the polymer material can be a naturally occurring polymer. For example, the polymer material can be collagen, a collagen co-polymer, or a mixture of collagen and a synthetic polymer.

The mesh network of the polymer material 26 may include pores up to a size of 250 microns. In some embodiments, the pores are a product of freeze thaw cycling, and are not large enough to permit cell ingrowth. In other embodiments, larger pores are included to permit cell ingrowth.

Fiber bundles 24, 28 can be formed of a synthetic material. In some embodiments, the fiber bundles include an aramid material. In some embodiments, the fiber bundles include a poly-paraphenylene terephthalaramide material, such as Kevlar® or Twaron® (of any grade). Some embodiments utilize synthetic materials for the fiber bundles, such as aramid fiber bundles, PVA fiber bundles, polyurethane fiber bundles, and/or polyethylene terephthalate fiber bundles. Some embodiments utilize naturally occurring materials for fiber bundles, such as, for example, silk fiber bundles, and/or collagen fiber bundles. In some embodiments, different materials can be used for different fiber bundles. In other embodiments, all fiber bundles are formed of the same material.

Advantageously, the polymer material 26 penetrates individual fibers of the circumferential and non-circumferential fiber bundles 24, 28. That is to say, the polymer material 26 infiltrates the fiber network and crosslinks within the fibers of the fiber bundles, thereby guarding against delamination of the fibers and slippage or tear out of the fibers after implantation. In some embodiments, the fiber material is hydrophilic, or at least somewhat conducive to absorbing water. The hydrophilic properties of the fibers facilitate infiltration of the polymer material 26 into the fiber networks and help to prevent fiber tear out. That being said, an important failure mode to consider and design for is the fiber bundles tearing out of the bulk polymer material during functional loading. Since the combined estimated peak force in the attachments of a native meniscus is around 140N as previously described, the artificial meniscus 2 can be designed to withstand this force without failure of the fiber-polymer interface when under physiologic-like loading [114], [115]. As such, the artificial meniscus 2 should have a fiber tear out strength of at least 140 N. Testing this type of loading would include applying tension to exterior ends 32 of the circumferential fibers 26 while the artificial meniscus is held stationary.

Figure 17A:
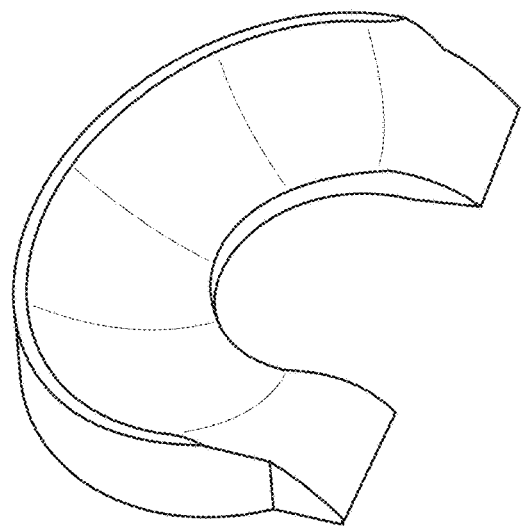
Figure 17B:
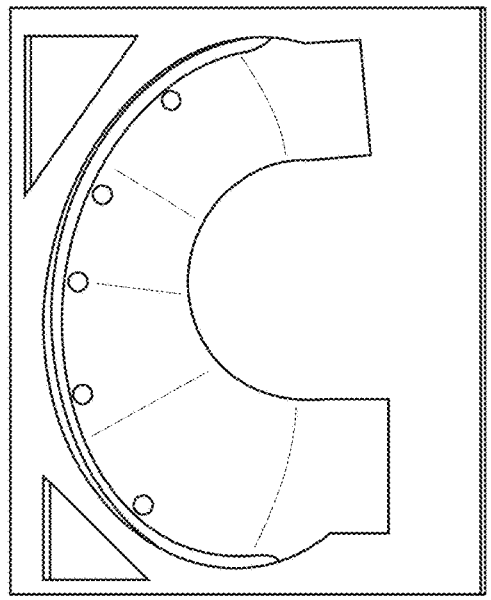

Modular processing techniques may be undertaken to form different parts or layers of a meniscus-shaped article 44 prior to any final processing steps that yield the implantation-ready artificial meniscus. FIGS. 17A-17G show different phases of an example process of fabricating the artificial meniscus 2. FIG. 17A shows a CAD model of the artificial meniscus 2. FIG. 17B shows a mold 33 for the artificial meniscus, the mold including holes 34 in the base. Different sets of fibers can be individually coated/penetrated by the bulk polymer precursor material to form intermediate components that are then set and can be arranged and molded together in the meniscus-shaped mold 33. Bulk polymer can be poured around the intermediate components once they are arranged in the mold, in multiple layering and setting steps if needed to accomplish the desired Z-direction layering. In this way, in the completed meniscus-shaped article 44, the bulk polymer material 26 surrounds the circumferential and non-circumferential fibers 24, 28 is a continuous, unitary structure.

In some embodiments, multiple layering and molding/setting steps may be performed to accomplish the layering of fiber bundles and various regions of the meniscus-shaped article. For example, a first, bottom layer of bulk polymer precursor material may be poured first and set into a bottom layer of polymer material 26. Or, alternatively, the mold can be inverted and a top layer of bulk polymer precursor material can be poured first and set.

Figure 17C:
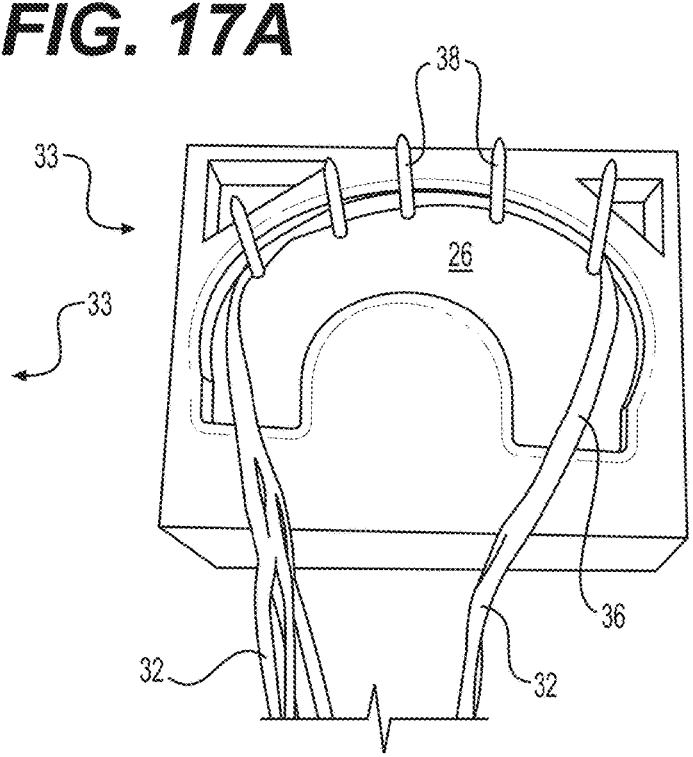

Separately, fiber bundles are coated/penetrated with the polymer material 26 and allowed to set. Separately coating the fiber bundles helps to keep the fiber bundles in their intended position during the later molding and layering steps that take place within the mold 33. The fiber bundles, now encapsulated within intermediate components, are arranged on the bottom or top layer of bulk polymer material. The intermediate component 36 that includes the circumferential fiber bundles can be set in a curved formation. FIG. 17C demonstrates an intermediate component 36 (including circumferential fiber bundles encapsulated within polymer material) being positioned around rods 38 that are placed within holes 34 around the periphery of mold 33. Alternatively, fiber bundles can be positioned around the rods 38, and then coated in precursor material while positioned between the rods 38 and the peripheral wall of mold 33, so as to form intermediate component 36 in a curved formation within the mold 33 itself. The rods 38 are removed before any further addition of polymer material to the mold to prevent any holes in the final meniscus-shaped article. As shown in FIG. 17D, a second layer of bulk polymer precursor material can be poured over the first intermediate component 36. The second layer of precursor can be set into a second layer of polymer material 26.

Figure 18:
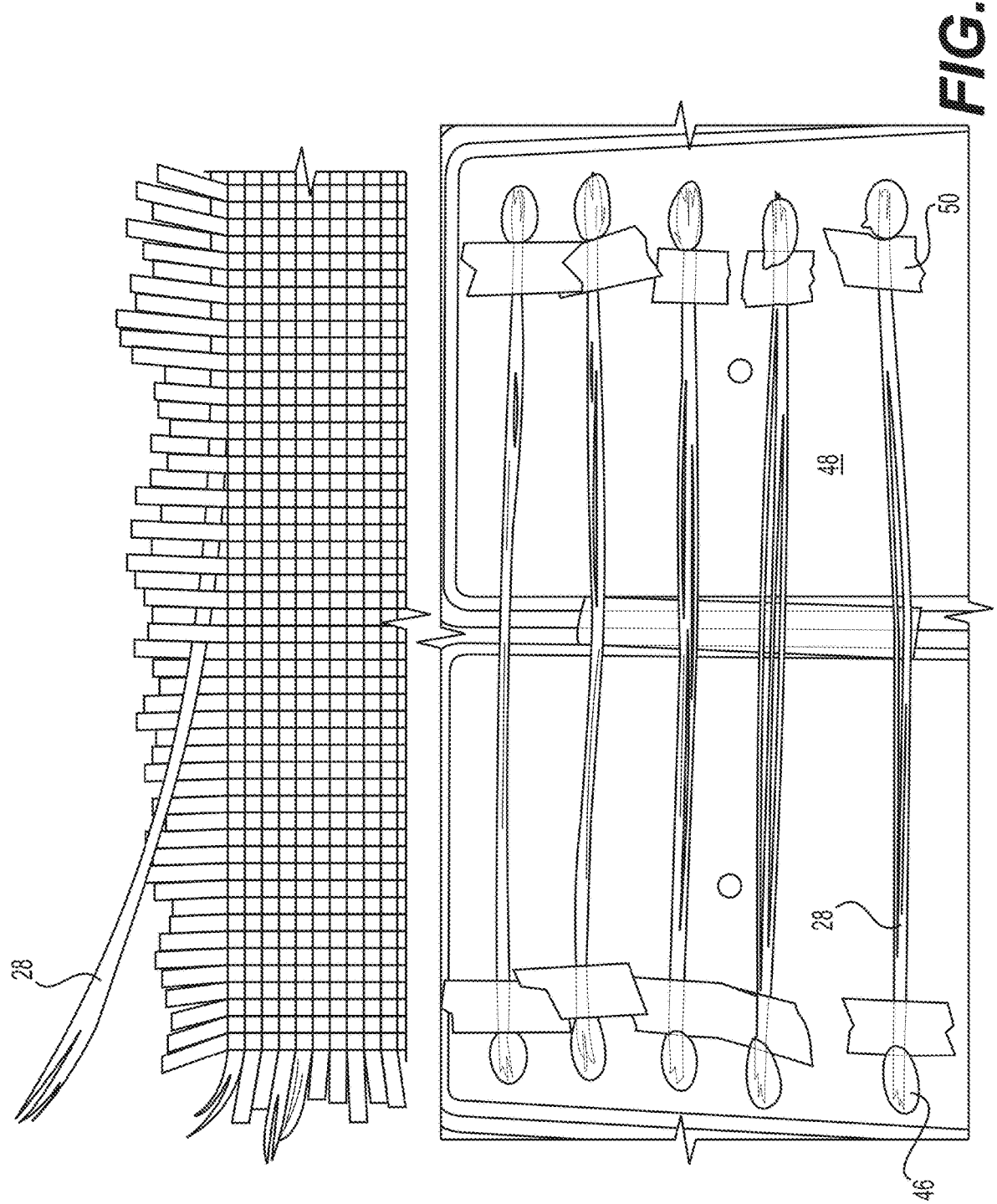
FIG. 18 shows steps of a processing method for the fabrication of a meniscus-shaped article. In some embodiments, non-circumferential fiber bundles are removed from a woven mat (top), dipped in polymer material at the ends, and affixed to a surface for setting and curing (bottom) before placement within the meniscus-shaped mold shown in FIGS. 17A-17G.

Second intermediate components including the non-circumferential fiber bundles can be separately embedded in polymer material, or at least partially embedded in polymer material. FIG. 18 shows non-circumferential fiber bundles 28 intended for radial alignment as shown in FIG. 1C. The fiber bundles are removed from a woven mat and at least the ends are dipped in polymer precursor 46 (in other embodiments, the entire fiber bundle could be dipped in polymer material). The fiber bundles 28 are then affixed to a surface 48 via tape 50 or some other affixation means, and the polymer precursor is allowed or induced to set/cure. These non-circumferential fiber bundles 28 can then be positioned on the polymer material 26 within mold 33 shown in FIG. 17D, to, for example, form the radially extending non-circumferential fibers of FIG. 12C. In some embodiments, the second intermediate component is set into a sheet-like shape prior to placing it into mold 33.

Returning to the processing step shown in FIG. 17E, a second intermediate component 40 encapsulating the non-circumferential fiber bundles of reinforcement sheet 30 in bulk polymer material can be set into contact with the second layer of polymer material 26 and the first intermediate component 36. Alternatively, the non-circumferential fibers 28 can be laid directly onto the second layer of polymer material 26 and polymer precursor poured over the non-circumferential fibers 28. Note that the intermediate molding and setting processing steps can be repeated as many times as necessary to achieve the desired layout, meniscal shape, and layering of fiber bundles. A final, top layer of polymer precursor can be poured over the second intermediate component 40 and the top 42 of the mold 33 clamped onto the mold 33 for the final setting step shown in FIG. 17F. The meniscus shaped article 44 is then removed from the mold and subjected to any final processing techniques, as shown in FIG. 17G. Final processing steps may be undertaken to convert the meniscus-shaped article 44 into an artificial meniscus 2 ready for implantation. These final processing steps can include smoothing of surfaces, incorporation of biocompatibility coatings, capturing the fiber ends 32 into a sheath, sterilization, and packaging the device into a double barrier pouch.

In some embodiments, a single polymer precursor material is used to set the intermediate components and form the layers of polymer material. The process of setting the polymer precursor includes freeze and thaw cycling.

Figure 19:
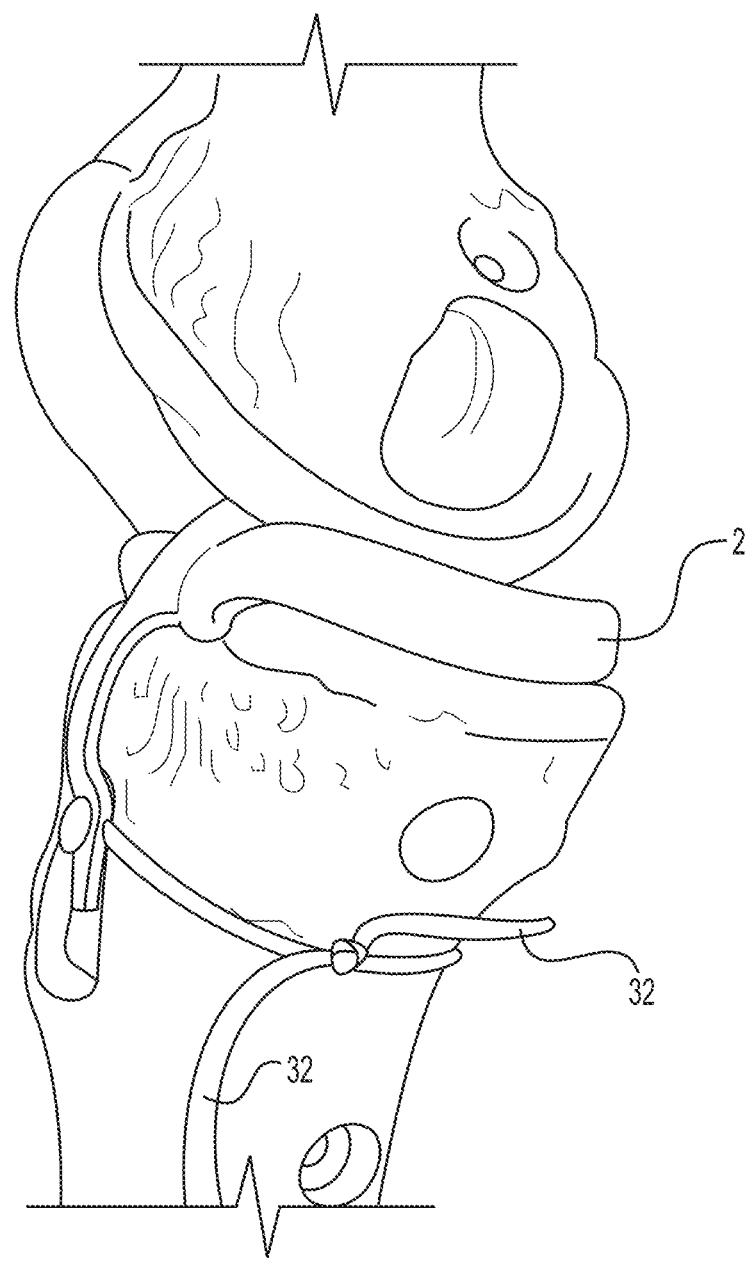
FIG. 19 shows ends of circumferential fiber bundles tied to each other on the outside of the bone.

Methods of implanting the artificial meniscus 2 are also disclosed herein. The methods of implanting can include threading a first end 32 of a circumferential fiber bundle 24 extending from the anterior horn 4 through a first bone tunnel, threading a second end 32 of the circumferential fiber bundle 24 extending from the posterior horn 6 through a second bone tunnel, and immobilizing the first and second ends of the circumferential fiber bundles 28. Immobilizing the first and second ends of the circumferential fiber bundle further comprises tying the first and second ends to each other, as shown in FIG. 19. In some embodiments, immobilizing the first and second ends of the circumferential fiber bundle further comprises affixing each of the first and second ends to a button-like structure. In some embodiments, immobilizing the first and second ends of the circumferential fiber bundle further comprises affixing each of the first and second ends to an interference screw.

Example 1: Design of an Artificial Meniscus

A synthetic meniscal substitute should be biocompatible and have mechanical requirements like a native meniscus such as compressive properties, flexibility, strength, and wear resistance. Optimally, it should be able to convert compressive loads into tensile hoop stresses, have proper pressure distribution, and decrease contact pressure on the tibia by increasing contact area. The fixation, surface characteristics, and geometry are also important factors to consider in development [33].

Shape: The shape of a meniscus implant is important for proper function. The shape will affect the contact area in the joint and therefore the contact mechanics. A high contact area and low contact pressure will help to distribute the force within the knee joint, one of the main functions of the menisci. As such, a meniscus implant should mimic the shape of a natural meniscus, with a concave upper surface for the femoral condyle and a relatively flat bottom surface for the tibial plateau. The size and shape of the implant disclosed herein was based on measured values of human menisci obtained from the literature or a representative anatomic meniscus model.

Since the medial meniscus is injured 2 to 4 times more often as the lateral meniscus [36], these examples pertain to the design of a medial meniscus. Like that of the natural medial meniscus, the medial meniscal implant will have an almost semi-circular shape, with an increasing width from anterior to posterior horn, and wedge cross section [90], [91]. The concepts and ideas disclosed herein can be translated to the design of a lateral meniscus without deviating from the scope of the disclosure.

Composite structure: The body of the implant can be a relatively flexible, biocompatible material that can conform to the joint space with compressive properties like the natural meniscus so that it has good force dissipation. It can also be smooth and wear resistant so no problems arise due to articulation with the femoral condyle. Another factor to consider for manufacturing is the material's ability to be moulded into a meniscus shape. One issue with a flexible, singular bodied implant is that it may deform under load and extrude out of the joint space since there will be no tensile hoop stresses around the periphery to limit the radial displacement under compressive load. For this reason, a composite implant with reinforcements can facilitate conversion of the compressive load to hoop stresses, as well as provide a means for attaching the implant within the joint to limit excessive movement.

The reinforcements of the implant can be oriented and aligned so that they can convert the compressive forces into tensile stresses to dissipate the load. To accomplish this, reinforcements can be circumferentially aligned with the periphery of the implant to mimic the circumferential collagen fibers in the natural menisci. The circumferential reinforcements can also extend out of the implant at the horns to the attachment points to prevent dislocation from the joint space under load like the native meniscus. Since the natural meniscus also has interwoven radial fibers to provide structural integrity, an implant can have reinforcements that give the implant radial strength. The radial reinforcements could come in the form of a base layer or weave-like reinforcement that spans across the cross-sectional area of the implant. This base layer would provide strength in all directions and limit implant deformation, as well as provide structural integrity and hold the entire construct together to better avoid tears, ruptures, and any further propagations.

Material Selection: With natural meniscus tissue being composed of mostly water, a material with that same characteristic would make a suitable replacement implant [5], [6]. Hydrogels are hydrophilic polymer networks that swell and trap high amounts of water, allowing them to mimic human tissue more closely than any other synthetic biomaterial [92]. One type of hydrogel that could be used for a meniscus implant is polyvinyl alcohol (PVA) hydrogel. It can be synthesized from a dissolved or molten PVA/water solution using a freeze-thaw cycling method, which physically crosslinks the PVA chains to form crystallites and a non-degradable hydrogel network [93]-[96]. They are also very biocompatible if synthesized using this method, partly because the crosslinks are formed without the use of chemical agents [97]. Due to PVA hydrogel's simple synthesis method, these hydrogels can also be molded into complex shapes prior to freeze-thaw cycling to produce their final shape and form.

In addition to having wear resistance even after millions of cycles [98], PVA hydrogel's mechanical properties can be tuned by changing initial PVA molecular weight, PVA concentration in solution, and the number of freeze-thaw cycles, along with numerous other parameters [68], [94], [95], [99], [100]. PVA hydrogels have been shown to possess similar compressive and viscoelastic properties to that of articular cartilage and meniscus tissue, and have already been used in the development of meniscal implants as mentioned formerly [64], [66], [101]-[103]. Although these previously described PVA-hydrogel meniscus implants had issues associated with them (radial tears, cartilage damage, delamination, extrusion), they show promise as meniscus replacement materials. Tailoring them to the application with a high polymer concentration and sufficient reinforcement can help a PVA-hydrogel meniscal implant to be strong enough to overcome previous failures and serve as a suitable meniscal substitute.

Reinforcements along the entire circumference of a meniscal implant would help to convert the compressive loads on the implant to tensile hoop stresses, like the circumferential fibers of a natural meniscus do within the knee joint. This can be best accomplished by using strong, stiff fiber bundles that are oriented along the circumferential outer periphery and extend from the implant horns for firm attachment within the joint. In addition to the peripheral fibers, a fiber weave, or deliberately patterned and placed non-circumferential fiber bundles, could be used as a base reinforcement for strength in all directions and protection from propagating tears and deformation.

Fibers with high strength and stiffness can be used as meniscal implant reinforcements. Optimally, the fiber material selected should integrate well into the PVA-hydrogel matrix to prevent delamination when exposed to loading conditions. High strength aramid fibers, such as Kevlar®, have been previously used in biomedical applications [104], [105]. They have high damage and fatigue resistance, and they can absorb water (unlike hydrophobic polyethylene fibers that have been previously used as PVA-hydrogel meniscus reinforcements [66], [106]). This water absorption could allow for penetration of the initial PVA/water solution into fiber bundles or weaves prior to freeze-thaw cycling to produce a sturdy composite with good interfacial adhesion and integration of fibers within the hydrogel matrix.

Risk analysis methods: Failure modes and effects analysis (FMEA) is a type of risk analysis performed on a design to identify potential hazards or failure modes, their effects of safety or performance, and possible solutions. Criticality analysis is an extension of FMEA that rates the severity of consequences, probability of occurrence, and probability it will escape detection [107]. In this analysis, 1 is the most desirable score in terms of minimizing risk, and 5 is the least desirable. The meanings of these ratings are shown in Table 1 to Table 3. The meanings for probability ratings were determined using average failure rates for allografts (about 20%) as the "moderate failures" cutoff, which is the only current approved treatment for meniscus replacement [54]. The three ratings are multiplied to provide a risk priority number (RPN) and a RPN threshold determines which risks are most critical and NEED to be addressed first [107]. An RPN of 20 will be the threshold value used here.

TABLE 1

Severity (S) ratings for risk analysis.

| Rating | Meaning |
| --- | --- |
| 1 | No Effect - No Danger or reduced performance |
| 2 | Minor Effect - May be noticed but function unaffected |
| 3 | Moderate Effect - Function affected: User may be inconvenienced or annoyed |
| 4 | High - Loss of Function; May cause injury or NEED for re-op and user is dissatisfied |
| 5 | Very High - Hazardous; Can cause permanent injury, complications, or death |

TABLE 2

Probability (P) ratings for risk analysis.

| Rating | Meaning |
| --- | --- |
| 1 | No failures |
| 2 | Low failures - a <5% incidence |
| 3 | Moderate failures - a 5% to 20% incidence |
| 4 | High Failures - a 20% to 50% incidence |
| 5 | Very High Failures - a >50% incidence |

TABLE 3

Detection (D) ratings for failure analysis.

| Rating | Meaning |
| --- | --- |
| 1 | Very High Detection - Patient is fully aware of malfunction or failure; Physician can easily detect issue; Defect is evident by visual examination prior to implantation |
| 2 | High Detection - Patient is suspicious of malfunction; Physician can detect through routine examination; Defect can be seen by light manipulation prior to implantation |

TABLE 3-continued

Detection (D) ratings for failure analysis.

| Rating | Meaning |
|---|---|
| 3 | Moderate Detection - Patient unlikely aware of malfunction; Clinician may require targeted investigation; Implant must be tested to find defect |
| 4 | Low Detection - Patient unaware of malfunction; Clinician may require non-invasive technique to detect; Implant requires stringent testing to find defect |
| 5 | Very Low Detection - Patient unaware of malfunction; Surgical intervention required to detect problem; Defect cannot be determined in preliminary testing |

Risk analysis results: An example of a preliminary failure analysis is shown in Table 4 for issues related to strength of the implant. This list would normally be expanded extensively during development and would include failures associated with other design functions such as attachment, implantation, and other categories. The listed potential failure modes, effects of the failure, and potential causes are mostly based on failures and effects seen in the natural meniscus [24], [108], [109]. Each potential cause of failure would normally be separated into its own row for each effect of failure and would have its own design control, but they are combined into one row after their initial introduction in this condensed version of a FMEA. The current design controls are verification tests that address the potential causes of failure and will be explained in subsequent chapters. The recommended actions are suggested future evaluations for failures modes that have risk priority numbers (RPN) over the threshold value of 20, and these future evaluations will be explained in a later section. The severity of the effects (S), the probability of the causes (P), and the ability to detect the failure mode (D) are listed to produce the RPN when multiplied.

TABLE 4

Results of implant design FMEA with severity (S), probability (P), and detection (D) ratings and resulting risk priority number (RPN). Recommended Actions for RPN of 20 or more are printed in bold

| Design Function | Potential Failure Mode | Potential Effect(s) of Failure | S | Potential causes of failure | P | Current Design Controls | D | RPN | Recommended actions |
|---|---|---|---|---|---|---|---|---|---|
| Strength | Partial Radial Hydrogel Tear - can be stable | Slight mechanical impairment (popping, catching) from unsmooth implant surface | 3 | Insufficient longevity of aydrogel | 2 | Cyclic testing - 1000 cycles of compression and tension load | 1 | 6 | None |
| | | | 3 | Insufficient hydrogel strength | 2 | Impact compression, tensile strength, and shear strength testing | 1 | 6 | None |
| | | Propagation risk to large size | 4 | Insufficient reinforcements throughout hydrogel | 2 | Implant design - base weave reinforcement | 3 | 24 | Optimize reinforcement layout; Composite tear testing |
| | Large Radial Tear (90% or more) | Accelerated cartilage degeneration from increased contact pressure | 4 | Insufficient longevity/ strength/ reinforcement | 2 | Cyclic and strength testing; implant design with reinforcement | 2 | 16 | None |
| | | Pain/ tenderness from increased contact pressure | 4 | Insufficient longevity/ strength/ reinforcement | 2 | Cyclic and strength testing; implant design with reinforcement | 1 | 8 | None |
| | | Mechanical impairment (locking, buckling) | 4 | Insufficient longevity/ strength/ reinforcement | 2 | Cyclic and strength testing; implant design with reinforcement | 1 | 8 | None |
| | Partial longitudinal tears - can be stable | Slight mechanical impairment (popping, catching) | 3 | Insufficient longevity/ strength | 2 | Cyclic and strength testing | 1 | 6 | None |
| | | Propagation risk to large size | 4 | Insufficient reinforcement | 2 | Implant design - base weave reinforcement | 3 | 24 | Optimize reinforcements; Tear testing |

TABLE 4-continued

Results of implant design FMEA with severity (S), probability (P), and detection (D) ratings and resulting risk priority number (RPN). Recommended Actions for RPN of 20 or more are printed in bold

| Design Function | Potential Failure Mode | Potential Effect(s) of Failure | S | Potential causes of failure | P | Current Design Controls | D | RPN | Recommended actions |
|---|---|---|---|---|---|---|---|---|---|
| | Complete longitudinal tear (bucket handle) | Accelerated cartilage degeneration from increased contact pressure | 4 | Insufficient longevity/ strength/ reinforcement | 2 | Cyclic and strength testing; implant design with reinforcement | 2 | 16 | None |
| | | Pain/ tenderness from increased contact pressure | 4 | Insufficient longevity/ strength/ reinforcement | 2 | Cyclic and strength testing; implant design with reinforcement | 1 | 8 | None |
| | | Mechanical impairment (locking, buckling) | 4 | Insufficient longevity/ strength/ reinforcement | 2 | Cyclic and strength testing; implant design with reinforcement | 1 | 8 | None |
| | Horizontal tears | Meniscal cysts and local swelling | 3 | Insufficient longevity/ strength | 2 | Cyclic and shear strength testing | 2 | 12 | None |
| | Oblique tears | Mechanical impairment (flap catching) | 4 | Insufficient longevity/ strength | 2 | Cyclic and strength testing | 1 | 8 | None |
| | | Propagation risk to complete longitudinal | 4 | Insufficient reinforcement | 2 | Implant design - base weave reinforcement | 3 | 24 | Optimize reinforcements; Tear testing |
| | Scuffing of Hydrogel on articulating surfaces | Incongruent fit - potential increase in contact stress and cartilage damage | 3 | Insufficient shear strength | 2 | Shear strength testing | 3 | 18 | None |
| | Hydrogel deformation | Extrusion/ Joint space narrowing - potential increase in contact stress and cartilage damage | 3 | Insufficient hydrogel longevity/ compressive strength and stiffness | 3 | Compressive and cyclic testing for deformation | 3 | 27 | Fatigue/Longer cyclic testing and deformation evaluation |
| | Reinforcement/ attachment fiber break or tear out (partial) | Slight mechanical impairment (popping, catching) from loose fibers | 3 | Insufficient strength or number of reinforcing fibers | 2 | Tensile strength testing of composites | 1 | 6 | None |
| | | | 4 | Improper layout of reinforcing fibers | 2 | Fiber tear out testing of implants | 1 | 8 | None |
| | | Reduced strength; risk of additional fibers breaking | 4 | Insufficient strength/ number/ improper layout of reinforcing fibers | 2 | Tensile strength and fiber tear out testing | 2 | 16 | None |
| | Reinforcement/ attachment fiber break or tear out (complete) | Mechanical impairment (locking, buckling) from implant dislocation | 4 | Insufficient strength or number of reinforcing fibers | 2 | Tensile strength testing of composites | 1 | 8 | None |

TABLE 4-continued

Results of implant design FMEA with severity (S), probability (P), and detection (D) ratings and resulting risk priority number (RPN). Recommended Actions for RPN of 20 or more are printed in bold

| Design Function | Potential Failure Mode | Potential Effect(s) of Failure | S | Potential causes of failure | P | Current Design Controls | D | RPN | Recommended actions |
|---|---|---|---|---|---|---|---|---|---|
| | Delamination of composite (base layer) | Mechanical impairment from loose weave component | 4 | Insufficient interfacial adhesion/ improper integration | 2 | Compression testing of composites | 1 | 8 | None |
| | | Reduced implant integrity - risk of hydrogel tear | 4 | Insufficient interfacial adhesion/ improper integration | 2 | Compression testing of composites | 3 | 24 | Optimize reinforcements; weave peel-off testing; tear testing |
| | Delamination of composite (fibers) | Reduced stress transfer - potential increase in contact stress and cartilage damage | 3 | Insufficient interfacial adhesion of reinforcing fibers and hydrogel | 2 | Fiber tear out testing of implants | 3 | 18 | None |
| | | | 3 | Improper integration of fibers into hydrogel matrix | 2 | Fiber tear out testing of implants | 3 | 18 | None |
| | | Mechanical impairment from dislocation of hydrogel component | 4 | Insufficient interfacial adhesion/ improper integration | 2 | Fiber tear out testing of implants | 1 | 8 | None |

Example 2: Functional Design Specifications

Most of the previous attempts at creating a synthetic meniscus replacement have focused on the biological aspects of the artificial mensicus, with many giving little attention to the implant's mechanical properties, especially related to the implant material's strength. One of the main reasons for failure of these implants is due to a lack of sufficient strength and longevity needed for the high-force environment seen in the knee joint. For this reason, a set of key functional mechanical requirements and design specifications were determined for the development of the artificial meniscus embodiments disclosed herein. The design and functional specifications described in this example are preferred but are not meant to limit the scope of the disclosure. An artificial meniscus not meeting these specifications may still fall within the scope of the disclosure.

Tensile Properties: Ultimate tensile strength: During axial compressive loading, the compressive force is distributed over the meniscus area and causes the meniscus to extrude radially due to its shape. This radial extrusion is resisted by the hoop stresses formed within the circumferential collagen fibers and insertional ligaments at the horns [7], [13]. These circumferential tensile stresses that develop in the menisci under load are believed to dominate their normal function and failure [11]. Although the ultimate tensile strength of anisotropic meniscal tissue varies by region, the mean maximum stress within the meniscus has been found to be 18.8 MPa for lateral and 17.6 MPa for medial menisci circumferentially, and around 4 MPa radially [110]. Therefore, an artificial meniscal implant will, in some embodiments, have an ultimate tensile strength of at least 12 MPa so that it is able to withstand the same maximum stresses as a natural meniscus, which is an important design specification that almost all previous developers of artificial meniscus implants have failed to address. This value can be taken from a sample that would be circumferentially oriented around the periphery of the implant, since that is where the tensile hoop stresses develop during loading to resist radial deformation [10], [17].

Tensile Properties: Tensile Modulus: The tensile modulus is dependent on region and direction within the menisci, so it can vary from about 50 MPa to 300 MPa and can be about 20 MPa to 70 MPa radially [11], [110]. This means an artificial meniscus implant will, in some embodiments, have a tensile modulus above 50 MPa in the circumferential direction and at least 20 MPa in the radial direction to limit deformation and extrusion. The upper limit for the modulus of an implant is not critical since metal is a common material used for spacer devices that have been used clinically and metal spacers would have a modulus much greater than 300 MPa [111]. However, to ensure the implant is as similar to the native meniscus as possible, the modulus will, in some embodiments, remain within an order of magnitude of the maximum reported value, or less than 1 GPa. These moduli can be taken in a hoop strain region experienced within the natural meniscus, which can be up to about 5% depending on region and flexion angle [112], [113].

Tensile Properties: Cyclic Tension: Tensile loads develop consistently during gait with each step taken, and have been estimated to peak around 50N during simulated motion at the anteromedial meniscal insertion site and about 65N±25 under joint loading in the posterior horn attachment site [114], [115]. Since the meniscus would realistically experience only one of the attachment site maximums, these values indicate a tensile load of about 90N would be a worst-case value for most individuals. To ensure the integrity of the implant is maintained, a safety factor of about 1.1 times can be added to the specification. This safety factor would make the specification correspond to the added load of both attachments (the 50N anterior load plus the 90N posterior load). Therefore, in some embodiments, the implant will sustain at least 100 N of tensile load for 1000 cycles is chosen. There should also be no significant changes in ultimate tensile strength or tensile modulus following these cycles.

Compressive properties: Compressive Modulus: A wide range of compressive moduli have been reported for the menisci and their values are dependent on strain level, loading rate, and test type. Studies have reported values for the compressive modulus of the human meniscus to be from 0.10 to 0.22 MPa under confined compression while others report modulus values from 0.30 to 1.13 MPa under unconfined compression at a physiologic strain and strain rate [116]-[118]. This means that under an unconfined testing protocol, a meniscal implant material should have a modulus of at least 0.30 MPa in a physiologic strain range. Like the tensile modulus specification, the upper limit for the compressive modulus is not critical since metal materials have been used in spacer devices and have moduli much greater than 1.13 MPa. Therefore, the modulus for a flexible prosthetic meniscus, will, in some embodiments, remain within an order of magnitude of the natural meniscus at less than 100 MPa.

Compressive properties: Impact Load Resistance: Different activities exert widely various levels of compressive force on the knee joint. The average peak loading on the knee joint during normal activities of daily life has been calculated to be up to 4.5 times body weight, with the medial compartment taking around 80% of the total load during its most heavily loaded times [88], [119]. The average peak forces on the tibia are among the highest in stair climbing, where the tibiofemoral force is sustained for about 0.2 seconds [88]. The menisci normally transmit between 50% to 70% of weight bearing load in the knee joint, but the medial meniscus can transmit up to 85% of the load in the medial compartment when the knee is at a high flexion angle [45], [120]. Assuming a $90^{th}$ percentile body mass of about 110 kg for men over 20 years old and a mean meniscal area of approximately 620 mm$^2$ across the tibial plateau, these values taken altogether implies that the medial meniscus must be able to withstand multiple rounds of 5.4 MPa compressive stress for 0.2 seconds without failure [91], [121]. Failure for this specification will be classified as a 5% or greater axial deformation and/or a modulus change that causes the implant material to fall out of its initial compressive modulus specification, which will be outlined in a later example. Therefore, in some embodiments, the artificial meniscus will have a 5.4 MPa "impact" stress value. This "impact" stress value would be a worst-case scenario and is based on Equation 2:

$$\frac{110 \text{ kg} \times 9.8 \frac{m}{s^2} \times 4.5 \ BW \times 0.8 \times 0.85}{620 \text{ mm}^2} = 5.4 \ MPa \quad [\text{Equation 2}]$$

Compressive properties: Cyclic Compression Resistance: An artificial meniscus implant must be able to withstand repeated compressive forces from activities, especially gait, without failure. This means it must maintain its functional size, stiffness, and strength after repeated loading. During gait, the knee joint is loaded to a maximum of about 2.5 times body weight during every step [88]. To ensure the implant can work in most patients after cyclic loading, a $90^{th}$ percentile body weight of 110 kg will be assessed [121]. During gait, the medial compartment of the knee accounts for about 80% of the total load and 60% of that proportional load falls on the medial meniscus [119], [120]. This means the meniscus must withstand approximately 1300 N of compressive force for every step taken. To improve long-term success of the meniscal implant, it will, in some embodiments, be able to withstand a compressive load of 1300 N for at least 1000 cycles. Using Equation 3, this corresponds to a compressive stress of about 2.0 MPa for an average meniscus area of 620 mm$^2$ [91]. Like the impact loads, failure for this specification will be defined as a 5% or greater change in height and a modulus change that puts it out of its specification range.

$$\frac{110 \text{ kg} \times 9.8 \frac{m}{s^2} \times 2.5 \ BW \times 0.8 \times 0.6}{620 \text{ mm}^2} = 2.0 \ MPa \quad [\text{Equation 3}]$$

Shear strength: Shear forces in the knee joint are much smaller, by about 10 to 20 times, than compressive forces during daily activities. Although most activities exert much less, these shear forces can peak at around 60% bodyweight in the posterior direction, especially for high flexion activities or stair climbing [88]. Using a $90^{th}$ percentile body weight of about 110 kg, the corresponding standing joint load of around 1000N puts the medial meniscus contact area at around 420 mm$^2$, which is 65% of the total compartment contact area of 640 mm$^2$ [88], [121], [122]. Using Equation 1 (mentioned first in the Detailed Description, above) with the meniscus contact area and 60% body weight load, a high estimated shear stress on the natural meniscus can be calculated to be around 1.4 MPa. Therefore, to withstand the shear forces experienced by the knee joint of most individuals, the material used for a meniscus implant will, in some embodiments, have a shear strength of at least 0.75 MPa.

$$\tau_{max} = 0.6 \times \frac{1000 \text{ N Load}}{420 \text{ mm}^2 \text{ Area}} = 1.4 \ MPa \quad [\text{Equation 1}]$$

Tear Out Strength: With a fiber reinforced composite serving as an implant, an important failure mode to consider would be the fibers tearing out of the bulk material during functional loading. Since the combined estimated peak force in the attachments of a native meniscus is around 140N as previously described, a meniscal implant will, in some embodiments, be able to withstand this force without failure of the fiber-hydrogel interface when under physiologic-like loading [114], [115]. This type of loading would have tension being applied to the attachment fibers that transition into the peripheral reinforcing fibers while the implant is being confined and held stationary in a joint-like space.

Pressure distribution in knee joint: A major problem with other treatment options, specifically a meniscectomy, include increased contact pressures on the tibial plateau, leading to cartilage degeneration. The peak contact pressure for the natural meniscus under static/standing loads from the literature is about 3 MPa when subjected to a 1000N joint load (1.16 times average BW) and 4 MPa with a 1500 N load (1.73 times average BW), and that pressure increases to over 6 MPa at 1000N joint load following a meniscectomy [121], [122]. The contact pressure on the tibial plateau is even greater during gait. The contact pressure under dynamic gait loading can reach 6.0 MPa and 7.4 MPa with an intact meniscus during the two peak loads of the gait cycle, and the contact pressure rises to almost 10 MPa after a meniscectomy [123]. The peak contact pressure under the same loading conditions for a meniscus implant can certainly remain below the alternative treatment (a meniscectomy) to prevent excessive cartilage damage. Preferably, in some embodiments, the implant would remain at the same level or below the peak pressure when the natural meniscus is intact, which would be 3 MPa for a 1000N load, 4 MPa for a 1500N load, and 7.4 MPa for gait loading. Therefore, there will be two specifications and acceptance criteria in relation to contact pressures: peak pressure will, in some embodiments, be no greater than 3 MPa at 1000N joint load and will, in some embodiments, be no greater than 7.4 MPa at a gait load of 2200N (2.5 times average BW) to match the natural condition [88], [121].

A summary of the preferred values for the design and functional specifications of the artificial meniscus implant can be found in Table 5.

TABLE 5

Preferred Values for Artificial Meniscus Implant Properties

| Design Specification | Acceptance Criteria | Reference(s) |
|---|---|---|
| Tensile Strength | >12 MPa | [110] |
| Tensile Modulus | 50 MPa to 1000 MPa | [11], [110], [112], [113] |
| Cyclic Tension Resistance | Tensile strength and modulus maintained after 1000 cycles to >100N | [114], [115] |
| Compressive Modulus | 0.30 MPa to 100 MPa | [116]-[118] |
| Impact Load Resistance | <5% change in height and compressive modulus maintained after impact loads to >5.4 MPa | [45], [88], [91], [119], [121] |
| Cyclic Compression Resistance | <5% change in height and modulus maintained after 1000 cycles to >2.0 MPa | [88], [91], [119]-[121] |
| Shear Strength | >0.75 MPa | [88], [121], [122] |
| Fiber Tear Out Strength | >140N | [113], [115] |
| Peak Contact Pressure at Static Load | <3 MPa at 1000N joint load | [122] |
| Peak Contact Pressure at Gait Load | <7.4 MPa at 2200N joint load | [123] |

Example 3: Methods

PVA Hydrogel Synthesis and Molding: Granular PVA (>99% hydrolyzed; molecular weight of 146,000-186,000 g/mol) was obtained from Sekisui (Dallas, Texas). PVA solutions were made according to weight percent (10, 25, or 40 wt %) by mixing with deionized (DI) water. For example, a 40 wt % solution is made by adding 33.33 g of granular PVA to a beaker, and then 50 g of DI water. The mixture was stirred, covered with aluminum foil, and allowed to sit for at least 4 hours. After allowing the granules to absorb some water, the mixture was stirred again and the wet PVA was compacted in the base of the beaker. The beaker was covered with foil, the foil was lightly perforated to allow air to escape, and the beaker was autoclaved at 248° F. for 25 min to completely dissolve the PVA granules. The molten PVA solution was removed from the autoclave after the cycle completed, the beakers were wrapped in foil to keep the solutions hot, and molding was performed immediately to prevent excessive viscosity rises from cooling. The 10 and 25 wt % solutions could be applied via injection through a syringe and could also be re-heated in a crockpot after the initial use, but 40 wt % solution quickly became very viscous, similar to a pliable solid and almost putty-like, and could not be injected or reused. Gloved fingers were wet with DI water to prevent sticking during hydrogel molding and the molten hydrogel solution was manually pushed into molds of the desired shape, such as prototypes or mechanical test samples, carefully to avoid creating air bubbles or voids. Once filled, the molds were covered and clamped tightly to compact the hydrogel into the proper shape and to push out any excess from the mold. All test samples and prototypes were subjected to 6 cycles of freezing at −20° C. for at least 1 hour and 5 cycles of thawing at 37° C. for about 45 minutes, or until complete phase change where the sample will turn from clear to white during freezing and back to translucent during thawing. After the last freeze cycle, the samples were subjected to a final $6^{th}$ thaw by submerging in DI water at 25° C. for about 1 hour before trimming any flash from molding. All samples and prototypes were stored in DI water at room temperature, for at least 24 hours, until immediately prior to use to prevent drying out.

Figure 20:
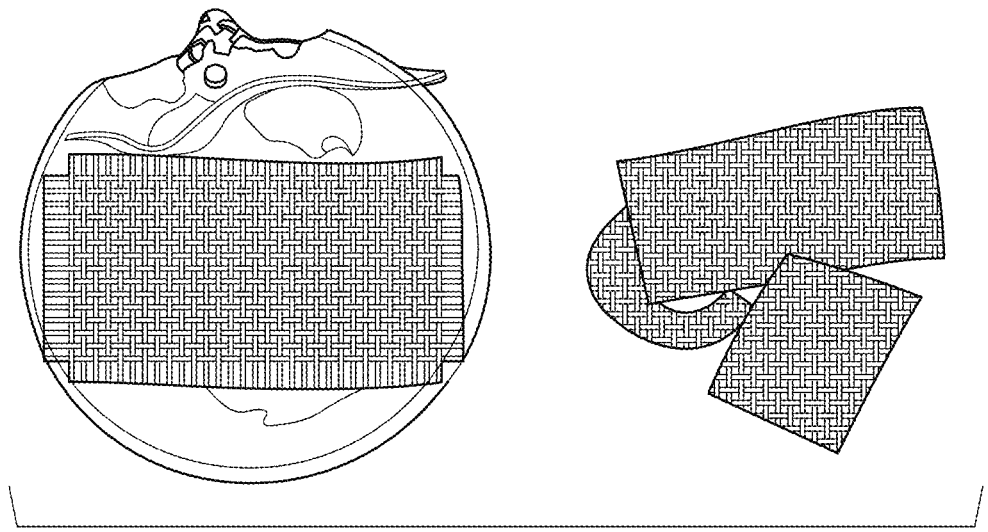
FIGS. 20A-20B show photographs of a composite mat fabrication process. Fiber weave mat is embedded in PVA-hydrogel (A) and then cut to size and stored in DI water (B).

Composite Mats: Para-aramid fibers, under the trade name Kevlar® 49, were obtained from Fibre Glast Developments (Brookeville, Ohio) in plain weave fabric mats with 17 picks per inch and a fiber denier of 1140. During initial prototype and test sample development, the warp and weft fiber bundles in these mats were prone to moving out of place and unweaving as composite samples were made, so to avoid this problem they were embedded in thin layers of PVA-hydrogel. The fiber mats were laid flat over a pool of molten 10 wt % PVA solution and pressed down to ensure full coverage of bottom surface. More molten PVA solution was poured on top of the fibers and spread evenly across weave. The weave and molten PVA solution were compressed between flat surfaces to ensure even coverage and placed through 2 to 3 freeze/thaw cycles. The hydrogel flash was removed and the composite mats were stored in DI water at room temperature after the $3^{rd}$ freeze and were cut to size depending on their use. An example of the process to make the composite mats is shown in FIGS. 20A-20B.

Figure 21:
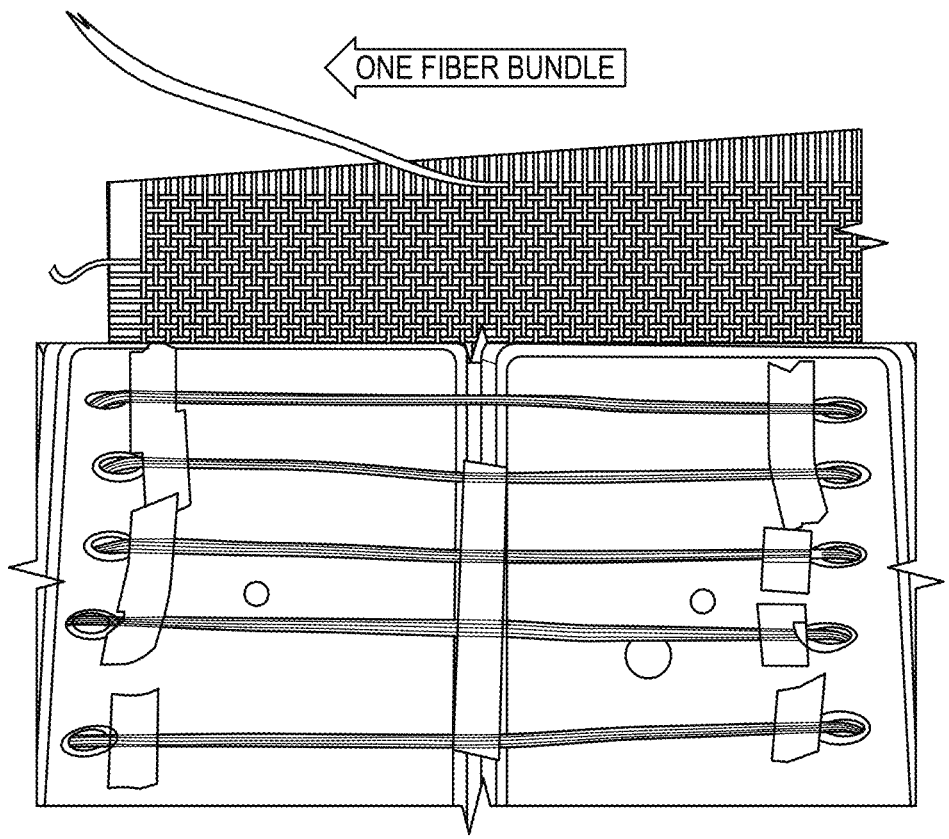
FIG. 21 shows a single fiber bundle from plain weave fabric (top) and the method used to align and connect the ends of five sets of multiple fiber bundles (bottom).

Multiple fiber bundles: The warp or weft fiber bundles, about 12 inches in length, were removed from the Kevlar® plain weave fabric as shown in FIG. 21. Multiple bundles were taped down together on a flat surface at one end, pulled tight ensuring side-by-side alignment, and the opposite ends were taped down together. Then molten 10 wt % PVA solution was applied to each end of the bundles to "glue" all fibers together at the ends (see FIG. 21). They were subjected to 2 to 3 freeze/thaw cycles, the excess PVA-hydrogel was trimmed from the ends, and the hydrogel ends were dried out overnight, leaving a group of fiber bundles bonded together at the ends with dry PVA. The fiber bundles were connected at the ends in this way to help prevent misalignment and to make creating samples and prototypes easier, since all fiber bundles could be pulled tight and tensioned together as one when connected.

General mold manufacturing: Two-part molds, consisting of a mold piece with the proper shape and a flat cover, were designed using Solidworks® V2016 CAD software (Dassault Systèmes Solidworks Corporation, Waltham, MA). The two parts of the mold were designed to be held together using small c-clamps. Since the shape and dimensions of the prototypes and test samples were changed regularly during development, the molds were created through additive manufacturing of PLA filament using a 3D printer (Fabricator FM1, Allentown, PA) due to the low cost and speed of this manufacturing process. The layering of filament during the printing process caused a slightly rough surface on the test samples and prototypes, but the properties tested here should not be affected by the surface of the samples and rely more on the bulk of the material.

Figure 23:
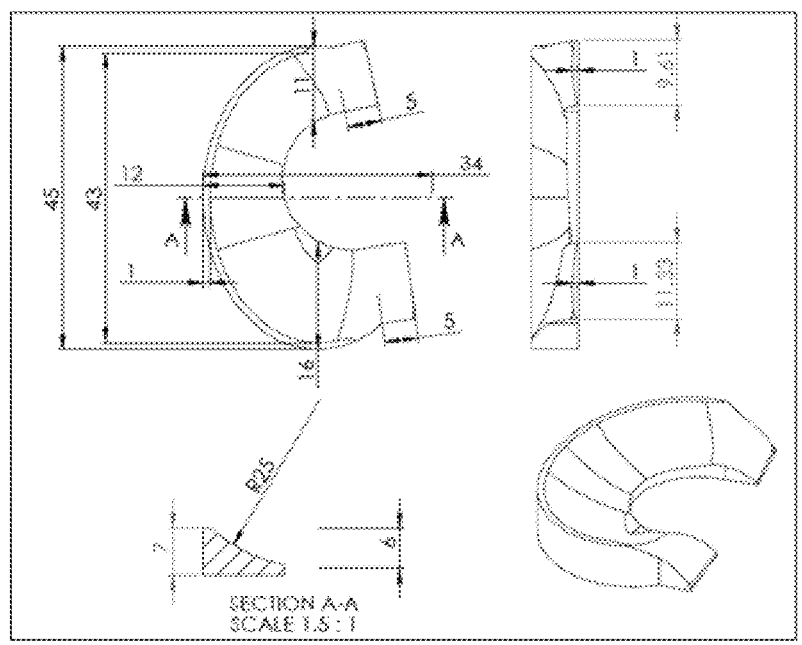
FIG. 23 is a drawing of the CAD-designed prototype that has a shape and size matched to a meniscus from a functional knee model. All dimensions are in millimeters.

Implant prototyping: An example of the entire step-by-step prototyping process is shown in FIG. 22. Prototype molds were designed in CAD software with their dimensions being determined using measurements made on the meniscus from a functional knee joint model (Somso NS 50, Coburg, Germany), as seen in FIG. 22A, or from values obtained in the literature [91]. An example of a CAD design used for the meniscus implant is shown in FIG. 22B and a drawing with its dimensions can be seen in FIG. 23. The first step in prototyping was 3D printing the molds with a series of holes in the base of them that followed the outer periphery of the meniscus, leaving about 1 mm of space to the outer wall (see FIG. 22C). Small nails were inserted into the holes from the bottom of the mold and taped down to prevent movement. A set of four connected fiber bundles were aligned along the nails in the area between the nails and the outer peripheral wall in the meniscus mold, and the fiber bundle ends exited the mold at the horn area. Then both ends of the fibers were pulled tight against the nails. Four bundles were used because that was the amount needed to provide an acceptable tensile strength in preliminary fiber testing. A molten 25 wt % PVA-hydrogel was applied through a 10-mL syringe around the mold periphery and the fibers were pushed into the PVA-hydrogel using forceps and splayed across the entire height of the mold. The PVA-hydrogel was compacted into all corners of mold periphery to ensure fibers were fully embedded with no air bubbles or voids, as shown in FIG. 22D. This initial fiber-hydrogel construct was subjected to one freeze cycle and removed to thaw during the next steps. The nails were removed from the mold and the initial composite construct was removed, trimmed of excess hydrogel to leave only a 1 to 2 mm layer around the fibers, and stored in water until the next step. The initial construct was put into a meniscus mold of the same shape, but without peripheral holes, in a similar configuration around the periphery as the first mold (FIG. 22E). Freshly molten 40 wt % PVA-hydrogel from the autoclave was pressed into the mold to fill it around the initial construct while removing any overflowing PVA as it was compacted. A pre-cut composite weave was pressed on top of the molten PVA-hydrogel (FIG. 22F), ensuring flatness and full encasing (no part of the weave extending beyond the edge of the meniscus area in the mold). Another thin layer of molten 40 wt % PVA-hydrogel was applied over the weave and meniscus area, and the mold was covered and clamped tight (FIG. 22G) before being subjected to 6 freeze thaw cycles.

Figure 24:
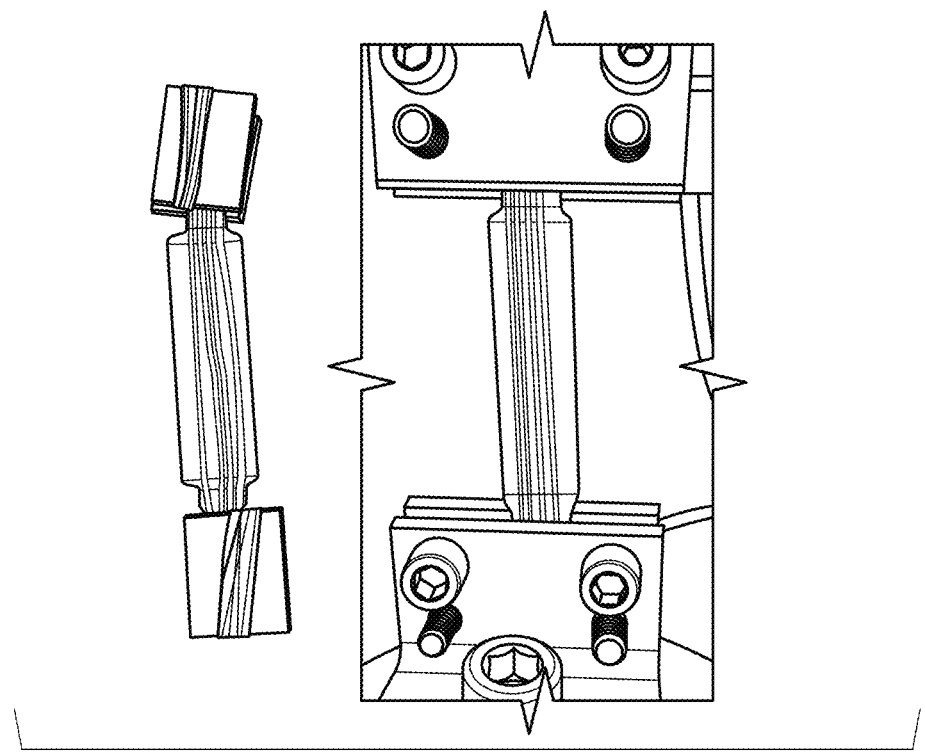
FIG. 24 shows tensile strength samples before (left) and after (right) loading into tensile grips.

Sample preparation for ultimate tensile strength testing: Samples were made in a similar way to the method previously described. Rectangular 3D printed molds (8 mm wide×2.2 mm thick×30 mm long) were used to create the samples. Molten 40 wt % PVA was pushed into the bottom of the mold, then 4 connected fiber bundles (determined to be a sufficient number in preliminary testing) were applied side-by-side to the PVA base layer so that all fiber bundles were straight and aligned in the mold. More molten PVA was added on top of the fibers and the molds were covered and clamped. The opposite ends of the fiber bundles were pulled tight to ensure no slack would be present in the tensile samples and the samples were freeze/thaw cycled. The composite samples consisted of a rectangular PVA portion with 4 embedded fiber bundles that extended about 5 inches from each end axially. To prepare the samples for gripping during the tensile tests, the fiber bundle extensions were wrapped around and glued between two small pieces of wood using cyanoacrylate adhesive, as shown in FIG. 24. Samples were made in this way to simulate the periphery of the meniscus implant with the extending fibers being used for attachment.

Ultimate tensile strength testing: For all tensile tests, composite samples were pulled in tension using a 15 kN load cell on the Model 858 MiniBionix II Testing System (MTS, Eden Prairie, MN). Samples were tested at 10%/min and 100%/min in preliminary testing, and results showed no dependence on strain rate, so the remaining samples were tested at 100%/min to limit time for samples to dry out. The samples were clamped in the grips, preloaded to 1 to 2N tensile load to determine gauge length, and pulled in tension until failure.

Tensile modulus: The tensile modulus was found using data from the ultimate tensile strength samples by calculating the slope of the trendline for the initial linear portion of the stress-strain curves, which usually fell in a segment between 1 to 4% strain. These strain levels also coincide with the physiologic region in a natural meniscus [112], [114].

Figure 25:
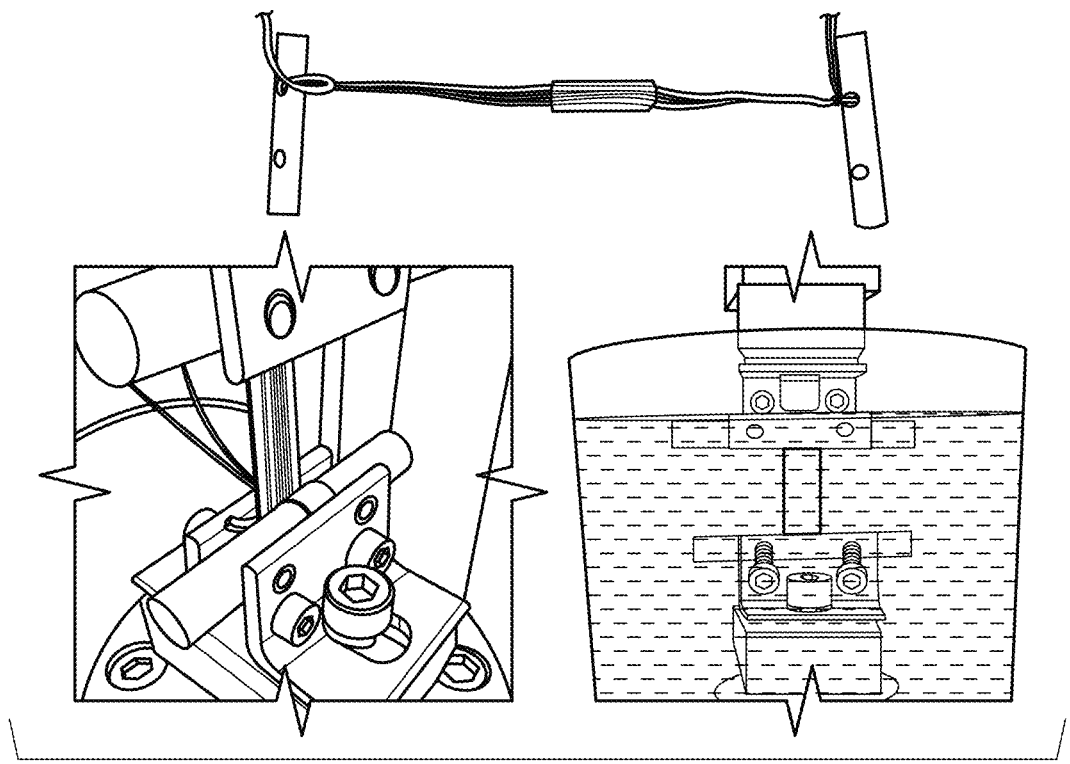
FIG. 25 shows a sample (top) tied to and wrapped around cylinders that are bolted in tensile grips (bottom left) before being submerged for testing (bottom right).

Cyclic tension testing: Samples were prepared as described previously, but the fiber extensions were not glued to wood. During cyclic testing, the samples were submerged in a tank of DI water at room temperature to prevent drying out, which would significantly weaken the wood-glued gripping method. The method ultimately used involved wrapping the extending fibers tightly around cylinders with through holes drilled into them outside of the wrapping area so that the bolts from the tensile grips could be inserted to hold the cylinders in place. The grips were tightened to hold the wrapped fibers between the grip walls and cylinders, as shown in FIG. 25.

Samples were subjected to a 10-cycle preconditioning to about 5% strain to determine the displacement needed to reach a 140N load. Samples were then loaded at 100%/min for 1000 cycles to a strain level that fell within the physiologic range of the native meniscus [112], which corresponded to a load of at least 140N. Following the cyclic tests, samples were inspected for deformities and/or defects due to cyclic tests, and then pulled in tension to failure to determine if there were any substantial losses in ultimate tensile strength or tensile modulus.

Sample preparation for impact strength testing: Samples were created in a similar way as previously described. Molten 40 wt % PVA was pushed into cylindrical 3D printed molds of 3 mm height and 10 mm diameter. Then a composite mat (see FIG. 20) was pressed on top of the molten PVA, ensuring flatness and full coverage of all cylinders. Another thin molten PVA layer was applied and the mold was covered, clamped, and freeze/thaw cycled. An example of a sample can be seen in FIG. 26. Samples were made in this way to simulate the bulk of the meniscal implant with a reinforcing base.

Figure 26:
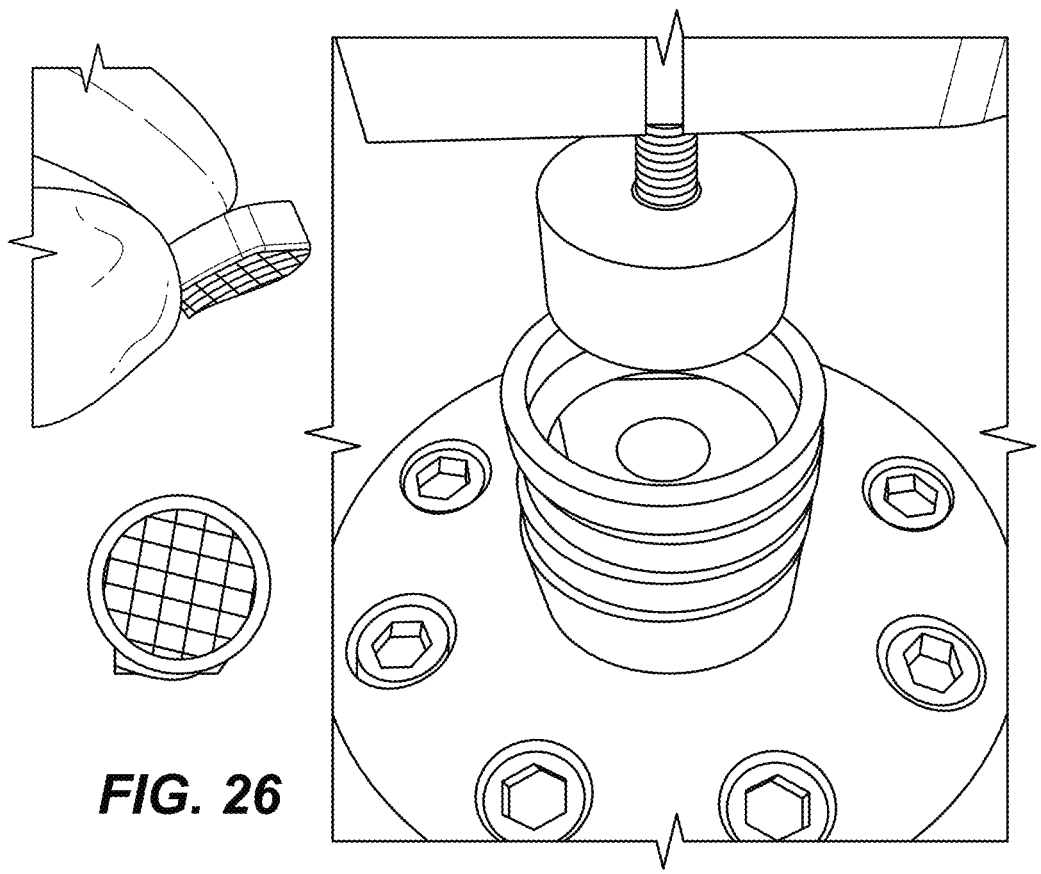
FIG. 26 shows a compression sample side (top left) and top (bottom left) views and the compression test setup (right).

Impact strength testing: All compressive tests were performed using the same machine as the tensile samples in unconfined compression between two flat plates while submerged in a tank of DI water, as shown in FIG. 26. The fiber mat reinforced side of the sample rested on the bottom plate, which had a layer of sandpaper to prevent sample movement during testing. For every step of the compression protocol, samples were preloaded to 1 to 2N and tested at 32% strain per second, which corresponds to the native meniscus's physiological strain rate of walking [118]. Prior to testing, a non-test sample was loaded to a very high strain to determine the strain level needed to reach the target specification stress of 5.4 MPa, which represents a worst-case scenario and will be referred to as the impact stress and/or load. Each test sample underwent 10 cycles of "conditioning" to about 15%, which is slightly larger than the estimated physiologic level in the meniscus, to determine initial compressive modulus [113], [118]. The samples were impact loaded to the strain that was previously found to correspond to 5.4 MPa for 0.2 seconds, which is the time that stress would be experienced in stair climbing, and then unloaded [88]. The change in sample height, which was found using the change in machine crosshead displacement needed to reach the 1 to 2 N preload, was used to determine any axial deformation and another 10 cycles of the conditioning loading was used to determine any change in modulus of the sample. The impact with subsequent conditioning loading protocol was repeated 2 more times, for 3 impact loads total, with about 2 minutes between tests. The initial preload height changes were noted between each impact step to determine any axial deformation.

Cyclic compression testing: The same samples from the impact loading tests were used in the cyclic tests with the same test setup. After the third impact load and conditioning cycles, samples were subjected to 1000 cycles of loading at 32%/s to a stress level of at least 2.0 MPa, which corresponds to a stress level the meniscus experiences in normal gait as previously described. This stress level was achieved in the same way as the impact tests, by setting the machine crosshead endpoint to a strain level that corresponded to a stress level greater than 2.0 MPa as determined by preliminary loading to a very high strain. During unloading cycles, the crosshead of the machine was set to a compressive strain level higher than 0% so that a small load would still be applied to the sample to prevent sample motion during cyclic testing. After the cyclic test, samples were subjected to another round of conditioning to determine height changes and modulus data as described previously. Then the samples were subjected to at least one more impact load followed by conditioning loading. The samples were then stored in DI water overnight as a "recovery" period before another conditioning and impact loading was conducted, followed by a final conditioning. Changes in displacements were determined in the same way as before during each conditioning step, during which the data for modulus determination was also collected.

Compressive modulus testing: The compressive modulus for each step in the compression protocol was calculated from the slope of a linear region in the stress-strain curve of the conditioning cycles between 2 and 12% strain, which is within the physiologic region [113], [118]. The average modulus for the $2^{nd}$, $5^{th}$, and $10^{th}$ cycle of each conditioning step was used. The initial 2% strain is excluded because strains lower than that were not always in the linear region of the stress-strain plot. Cycle 1 was not included in the modulus calculation because it always went to a higher stress level and had a different modulus than the remaining 9 cycles, which all overlaid well on a stress-strain plot due to similar responses.

After testing, small decreases in sample height were observed. The height changes caused the stress-strain curves to shift to the right (to a higher strain level) since the same amount of displacement would produce a higher strain and stress levels in shorter samples. This height change altered modulus calculations since the 2 to 12% strains were at different locations and reached different stress levels. To fix this problem, modulus values were also calculated using a linear portion of the stress strain curve that fell between 0.03 MPa and 0.14 MPa of compressive stress so that the samples' moduli could be compared in the same force ranges. Stress was calculated using the original cross-sectional area for each step, so force and stress were proportional for all steps in the loading protocol. The 0.03 MPa value corresponded to the sample's initial stress level at 2% strain, and the 0.14 MPa value corresponded to the stress level at 15% strain for the step in the loading protocol that experienced the lowest maximum stress during its conditioning step.

Figure 27:
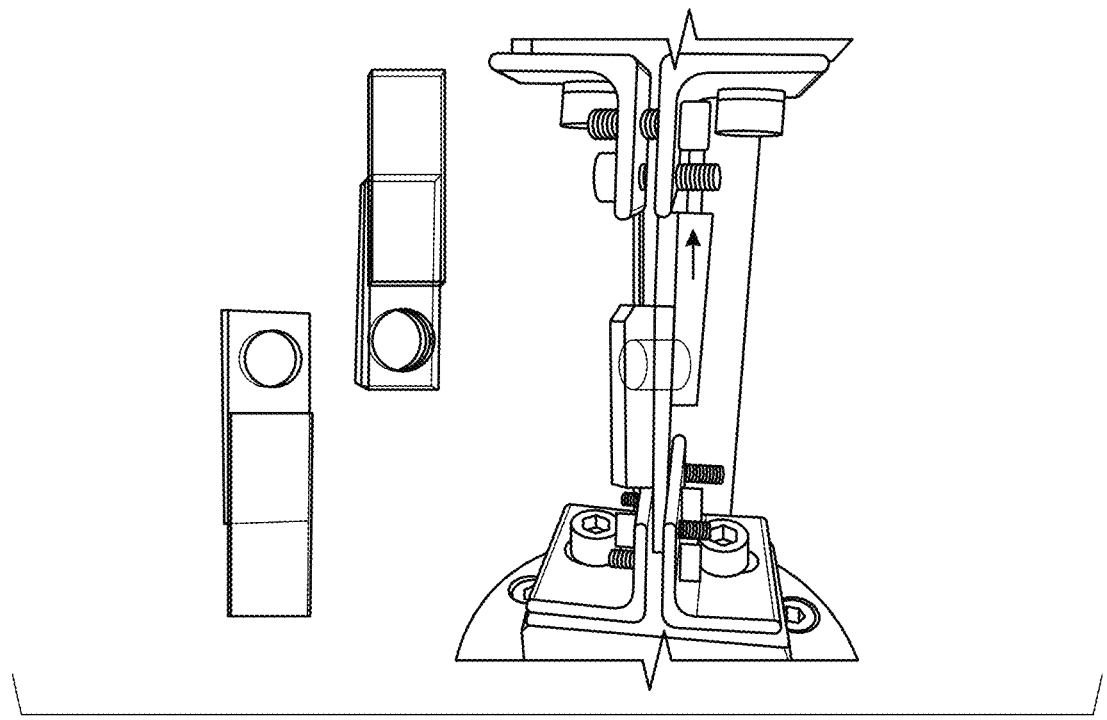
FIG. 27 shows a shear test setup. The testing apparatus before loading sample (left) and after loading sample, shown as white cylinder, into machine (right) with arrows depicting direction of loading.

Shear strength testing: Shear samples were made using a cylindrical 3D printed mold like the compression samples, but with 10 mm height, 10 mm diameter, and no fiber weave reinforcements. No reinforcement was used in these samples since the shear loading the implant would experience in use would mostly be on unreinforced areas, mainly the top surface of the implant. Samples were tested in shear loading using a custom two-piece plastic testing apparatus, as shown in FIG. 27, similar to methods found in the literature [67]. Each piece had a 10 mm diameter, 5 mm deep hole so that half of each hydrogel shear sample could be mounted in them while allowing both pieces to contact each other. The apparatus was mounted in tensile grips using the same test system as before so that the hydrogel samples were held in place between the two contacting pieces. The failure load showed no dependence on strain rate in initial testing, so the samples were tested at a high rate of 50 mm per minute to limit sample dry-out, in a direction perpendicular to the hydrogel's axial axis for shear loading, until failure (see FIG. 27). A wrench was used to constrain movement of the plastic pieces to the testing direction. Shear strength, $T_{max}$, was calculated using Equation 4, where $F_{max}$ is the maximum force measured and r is the sample radius.

$$\tau_{max} = \frac{F_{max}}{\pi r^2} \qquad \text{[Equation 4]}$$

Implant fiber tear out testing: A custom 3D printed testing apparatus was developed to perform this test to simulate the knee joint environment, with one side being flat to simulate the tibial plateau and one side having curvature to simulate the femoral condyle. The testing apparatus was a modified version of the meniscus prototype mold (simulated curved femur) and cover (simulated flat tibia). The area on each piece of the apparatus where the implant's fibers exited was cleared of any interfering walls so the fibers could be pulled straight in tension. The apparatus also had a rectangular extension to allow mounting in the materials testing machine's tensile grips. This apparatus can be seen in FIG. 28, with the CAD model shown in FIG. 29 for clarification. Prototype composites were made in a meniscal shape that matched the apparatus shape as previously described, but the base mat layer of reinforcement was not included since the prototype test samples would not be experiencing loading at this area. The prototype samples were inserted in the apparatus and covered and clamped, with some needing trimming at the inner periphery for a tight, secure fit. The extending fibers were gripped using the cylinder wrapping method described for the cyclic tensile testing samples, and the other end of the apparatus was mounted in the bottom grip so that the meniscal prototype samples were oriented vertically to be tested in tension. The apparatus held the PVA portion of the prototype in place while the gripped fiber ends were pulled away in tension, in the opposite direction of the periphery of the meniscus prototype and through the bulk PVA material. The test was run until a sudden decrease in force was observed, and then the test was stopped and the prototype samples were examined for failure mode.

Sample preparation for pressure distribution testing: The pressure distributions for different prototypes and conditions were assessed on the tibial plateau of a modified Somso NS 50 functional knee model (Marcus Sommer SOMSO Modelle GmbH, Coburg, Germany) under compressive loading. The functional knee model came equipped with a singular elastic meniscus piece, where the medial and lateral menisci were connected in the middle and inserted into the model by fitting a protrusion at the base of the meniscal piece into a cavity in the center of the tibial plateau. A mold of this model meniscal piece was created so that prototypes with the same shape could be made from the PVA-hydrogel and as a fiber composite. A 3D scan of the model meniscus was obtained using the FaroArm Edge (FARO Technologies, Inc. Lake Mary, FL) portable coordinate measuring machine and was converted to a 3D mesh using Geomagic® Design X (3D Systems, Rock Hill, SC). The highly detailed mesh was then simplified and smoothed using Meshlab open-source mesh processing software [124] and converted to a solid CAD model from which a mold was created in Solidworks V2016 (Dassault Systèmes Solidworks Corporation, Waltham, MA). The mold was 3D printed and prototypes were made in the model shape as previously described. A summary of this process can be seen in FIGS. 30A-30E. Some of the prototypes tested were also made using the original, CAD designed and dimensioned mold shapes as previously described (see FIG. 22).

Pressure distribution testing: The knee model was modified and mounted in the same materials testing machine as all other tests. This modification involved removing most of the ligaments to allow easier implantation of prototypes and addition of threads in the bone sections of the model for mounting in the testing machine, as shown in FIG. 31.

The knee model was loaded in full extension to about 1000 N of compressive force for each prototype or condition. This was accomplished by determining the testing machine's displacement set point needed to reach 1000 N prior to measurement for each case, and then setting the machine's endpoint to that displacement value for the tests.

A pressure indicating film (Fujifilm PreScale® Super Low, Pressure Metrics LLC, Whitehouse Station, NJ) was wrapped in plastic wrap to prevent it from getting wet from the hydrogel and placed on the medial tibial plateau for each test condition under the prototype being tested (see FIG. 35). Then the knee model was loaded at a physiologic strain rate, held for 5 seconds, and then unloaded. The strain rate used for all conditions was 2.25 mm per second and was determined by assuming all prototypes to be 7 mm thick, which is around the average maximum thickness for medial menisci, and using the physiologic 32% per second strain rate [91], [118]. The load was held for 5 seconds to allow sufficient color development on the film. The film samples were then analyzed using FPD-8010E software (Fujifilm Corporation, Valhalla, NY) to determine pressure distribution values such as pressurized areas, average pressure, and maximum pressure. The film's pressure range was 0.5 MPa to 2.5 MPa, and any pressure value below 0.5 MPa was filtered out of the calculations since these readings were likely due to contact from inserting and removing the film from the setup instead of the actual compression test on the knee model. The conditions tested using this setup are shown in Table 6, with visual depictions of each condition shown in FIG. 30 to FIG. 37.

Once all the data was collected and analyzed, the prototype that had the best results was tested again to 1500N for comparison with literature values, and then again to 2200N to simulate a normal joint force experienced during gait (2.5×BW for an average person) [88], [121]. The same low pressure indicating film previously mentioned was used in these tests. A second test with another film indicating a higher pressure range of 2.5 MPa to 10 MPa was used to assess whether any high-pressure areas existed. The films for the higher joint load tests were not analyzed using the previously mentioned software. Instead, a Color Correlation Manual (Sensor Products Inc., Madison, NJ) was used to estimate these contact pressures where a darker color indicates a higher contact pressure within the indication range of each film.

TABLE 6

Conditions tested for contact pressure distribution in the knee model

| ID# | Condition or Prototype | Description | Visualization |
|---|---|---|---|
| 1 | Original Model Meniscus | The meniscus that came with the functional knee model. A protrusion on the meniscus is inserted into a slot in knee model to hold it in place. | FIG. 30A, FIG. 31, FIG. 32 |
| 2 | Medial Meniscectomy | The medial meniscus of #1 is cut off to leave only the lateral meniscus to be inserted into the slot in the knee model. | FIG. 33 |
| 3 | Unreinforced PVA Model Meniscus | A PVA prototype in the same shape and inserted the same way as #1. It is not reinforced with any fibers. | FIG. 34 |
| 4 | Unattached Composite Model Meniscus | A hydrogel-fiber composite prototype with peripheral fibers and a fiber mat base in the shape of #1. It has the extending fibers for attachment, but is inserted using the slot in the knee model. | FIG. 30E, FIG. 35 |
| 5 | Attached Composite Model Meniscus | A hydrogel-fiber composite the same as #4, but the extending fibers are inserted into bone tunnels in the knee joint model and tied tightly around the outside of the bone for firm attachment. | FIG. 30E, FIG. 36 |
| 6 | Matched Shape Composite Meniscus | A hydrogel-fiber composite with a flat base and with a shape and dimensions created in CAD software, but matched to the dimensions of #1. It has all reinforcements and is attached like #5. The testing is performed with the lateral meniscus of #2 in the lateral side of the knee model. | FIG. 37A |
| 7 | Generic Shape Composite Meniscus | A hydrogel-fiber composite with all the same features and conditions as #6, but created in CAD software using generic dimensions from literature. | FIG. 37B |

Example 4: Prototype Testing Results

For all tensile and compressive results, engineering stresses and strains were used. Normal stresses, σ, were calculated according to Equation 5:

$$\sigma = \left| \frac{F}{A_0} \right| \quad \text{[Equation 5]}$$

where F is the perpendicular force measured at a specific displacement and AO is the initial, unstrained cross-sectional area of the specimen. The original cross-sectional area was used in the stress calculations for every step of the compression protocol. Strains, ε, were calculated according to Equation 6:

$$\varepsilon = \left| \frac{\Delta L}{L_0} \right| \quad \text{[Equation 6]}$$

Where ΔL is the displacement of the testing machine crosshead (or change in axial size of the specimen during testing) and $L_0$ is the original sample length for tension or original sample height for compression. The $L_0$ used for all steps in the compression protocol was the original sample height before any impact or cyclic loads. Absolute values are used for these calculations since the compressive tests would give negative values due to the negative force and displacement measurements given by the testing machine software.

Elastic modulus, E, is calculated using Equation 7, and can also be found from the slope in the initial linear portion of a stress-strain curve.

$$E = \frac{\sigma}{\varepsilon} \quad \text{[Equation 7]}$$

Figure 39:
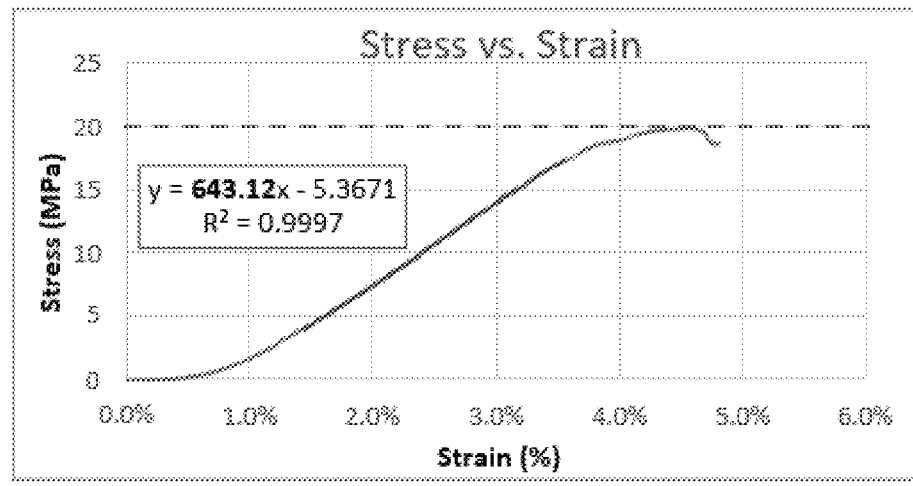
FIG. 39 shows a tensile stress versus strain plot showing linear portion in red with trendline slope value in bold text as the modulus, and the blue dashed line representing the tensile strength. Data is taken from sample 2.
Figure 41:
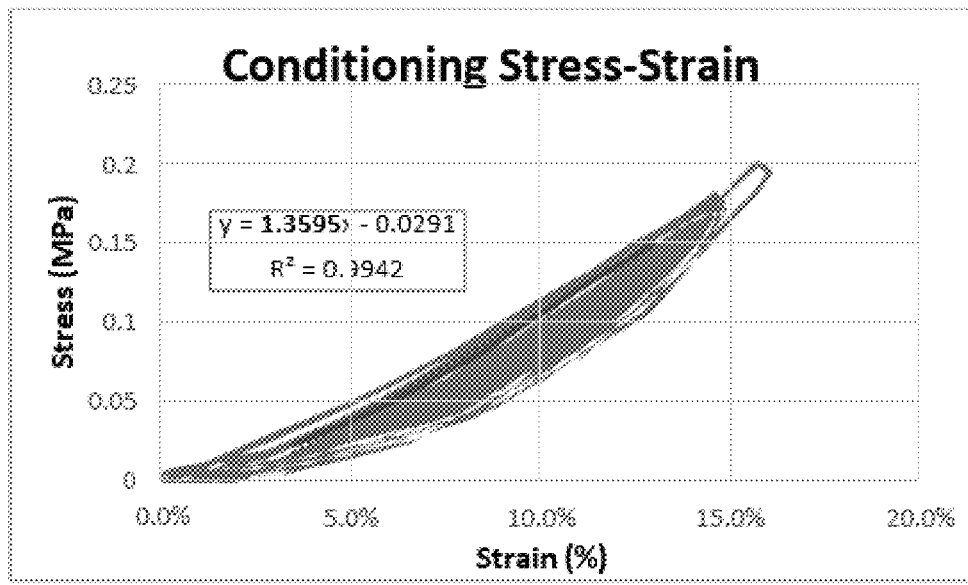
FIG. 41 shows a compressive sample stress-strain plot during 10-cycle conditioning step showing linear portion in red with trendline slope value in bold text as the modulus. Data is taken from sample 3 after one impact.

Reported elastic modulus values were calculated in Microsoft Excel® using the slope of the trendline in the initial linear portion of stress-strain plots for both compressive and tensile moduli (see FIG. 39 and FIG. 41).

Tensile Strength and Modulus: Rectangular composite samples of 40 wt % PVA-hydrogel and four fiber bundles were tested in tension to failure (n=4). Stress and strain was calculated from the force and displacement data as previously described, and plots were created to determine the tensile strength and modulus values. The tensile strength was defined as the maximum stress value achieved for each sample, and the modulus was found using the slope of the initial linear portion of the stress-strain plot as previously described (see FIG. 39). The calculated tensile strength and moduli values are presented in Table 7 with average and standard deviation values.

Figure 38:
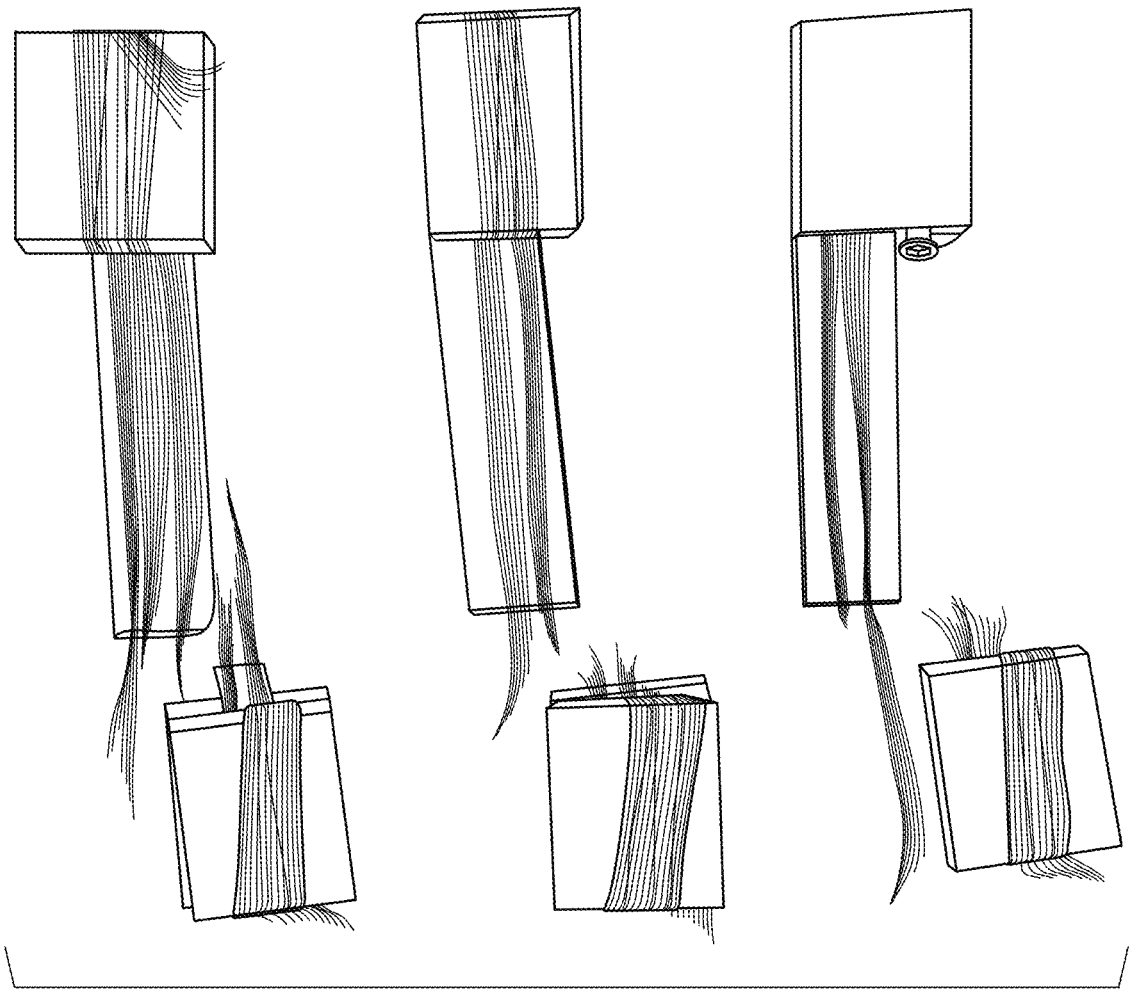
FIG. 38 shows failure mode of the tensile samples by fiber fracture, which occurred at the griped area for most samples.

The samples failed in tension by reinforcing fiber fracture, as seen in FIG. 38. Most failed outside of the PVA-H area and at the wood where the fibers were gripped. This likely means that there were stress concentrations at the grip areas or where the fibers were glued to the wood.

The tensile strength and modulus of the samples both met their respective design specifications. The accepted range for the tensile modulus of a meniscus implant was 50 MPa to 1000 MPa. With an average modulus of 589 MPa, the samples tested here fall within that range. The average tensile strength of the samples, 20.2 MPa, was also higher than the minimum specification value for a meniscus implant of 12 MPa.

It is important to note that the tensile strength values can also be increased by addition of more fiber bundles as reinforcements, which would also increase the modulus values. The number of reinforcing fibers is an important parameter for this specification, since they are the main contributor to the tensile strength of the test samples and the implant. The alignment of these fibers also influence the results. If fibers are not properly aligned within the sample, some fibers could prematurely fracture before the rest of them.

TABLE 7

Tensile strength and modulus values for samples pulled in tension directly to failure.

| Sample # | Tensile Strength (MPa) | Tensile Modulus (MPa) |
| --- | --- | --- |
| 1 | 19.1 | 410 |
| 2 | 19.9 | 643 |
| 3 | 19.7 | 618 |
| 4 | 22.0 | 685 |
| Average | 20.2 | 589 |
| SD | 1.28 | 122 |

Figure 40:
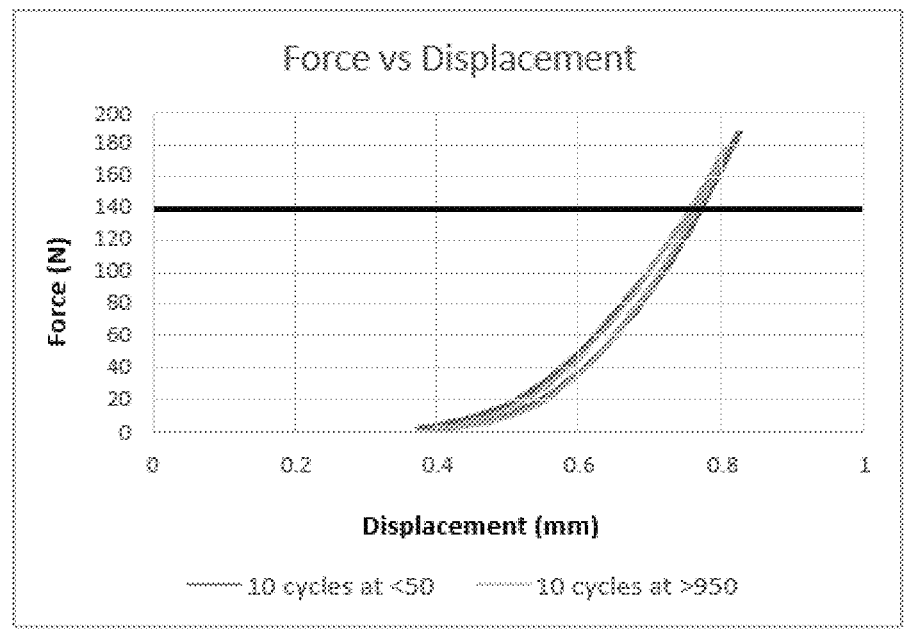
FIG. 40 shows a plot of force versus displacement showing 10 cycles within the first 50 cycles and 10 cycles in the last 50 cycles where the specification load of 140 N, shown as the black dashed line, is sustained during all cycles.

Cyclic Tension Results: Composite samples of 40 wt % PVA with four fiber bundles were loaded for 1000 cycles to a tensile load greater than 140 N to simulate an extreme case of repeated loading that the native meniscus would experience (n=4). This repeated load was sustained for all 1000 cycles, as seen in FIG. 40. As cycling continued, the testing machine did not strain the samples as much as in earlier cycles, so there is a slight discrepancy in the load that the cycles reached between early and late cycles. Without being wed to theory, the cycling also likely forced water out of the hydrogel during stretching, so the samples became slightly stiffer and reached a higher load at a lower strain level.

After the cycles, samples were pulled in tension to failure to determine tensile strength and tensile modulus. These values, along with the approximate cycle load of each sample for reference, are reported in Table 8 with averages and standard deviations. The samples also failed by fiber fracture near the grips like the other tensile samples.

The average tensile strength (21.9 MPa) and tensile modulus (709 MPa) values for the cyclic samples after being loaded to at least 140 N for 1000 cycles remain within the specification for a meniscus implant, which was >12 MPa tensile strength and 50 MPa to 1 GPa tensile modulus. The values for tensile strength and modulus for the cyclic samples were in fact slightly larger than those of the samples that were tested directly to failure. Without being wed to theory, this could be attributed to the loss of water from the hydrogel mentioned earlier, or could be due to the cyclic samples being slightly smaller in cross-sectional area overall (Poisson ratio effect) than the samples pulled directly to failure. This smaller area would alter the calculations for the stress levels and in turn the tensile modulus.

TABLE 8

Tensile strength and modulus values during pull to failure tests for cyclic samples after cycling, and the approximate cycle loads of each sample.

| Sample # | Tensile Strength (MPa) | Tensile Modulus (MPa) | App. Cycle Load (N) |
|---|---|---|---|
| 1 | 19.6 | 811 | 180 |
| 2 | 20.0 | 803 | 175 |
| 3 | 24.0 | 562 | 150 |
| 4 | 24.0 | 660 | 170 |
| Average | 21.9 | 709 | 169 |
| SD | 2.42 | 120 | 13.1 |

Compressive property testing overview: Cylindrical composite samples of 40 wt % PVA with a reinforcing fiber mat at the base were subjected to a 10-cycle conditioning loading to 15% compressive strain, followed by three impact loads to over 5.4 MPa compressive stress (n=3). Following the three impact loads, the same samples were subjected to 1000 cycles of compression to at least 2.0 MPa, an additional post-cycle impact load, and another impact load after storage in DI water for at least 24 hours as a recovery period. A conditioning step was performed before and after all steps of the loading protocol. Since the same samples were used for the impact and cyclic loading tests, the results were combined and are presented together. The conditioning steps were used to determine the modulus of the samples before and after each loading step and the modulus was found using the initial linear portion of the stress-strain curve as previously described (see FIG. 41). The conditioning steps were also used to determine the change in preload height of each sample (the machine's crosshead position needed to reach 1 N to 2 N of compressive load) which gave the residual axial deformation after each step.

Figure 42:
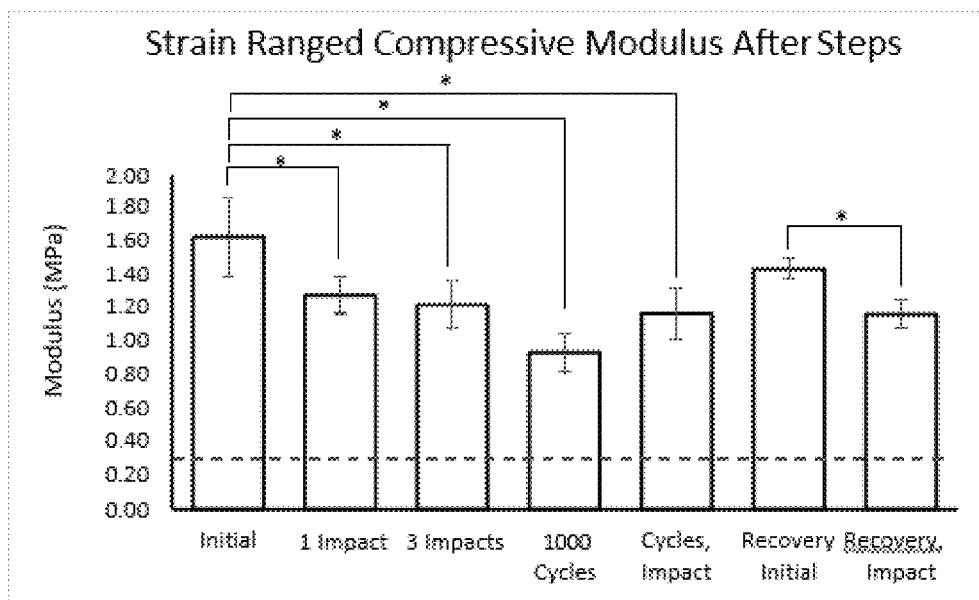
FIG. 42 shows a comparison of compressive moduli after each step in the compression loading protocol using a 2% to 12% strain range. A (*) indicates significance, but the modulus after 1000 cycles was significantly different from all others except for after recovery, impact. The minimum specification of 0.30 MPa is shown in red.

Compressive Modulus Changes Using Strain Range: The compressive modulus data using the 2% to 12% strain range for all samples after each step can be seen in Table 9 with the average and standard deviations for each step, which are also shown in FIG. 42. The compressive modulus was highest initially before any loading at 1.63 MPa. The lowest the compressive modulus value reached during the loading protocol was after the 1000 cycles at 0.94 MPa and the highest was after recovery at 1.44 MPa. After every step in the loading protocol, the modulus remained well within the acceptable specification range of 0.30 MPa to 100 MPa. The modulus values were also very close to or even below the native meniscus's upper range of 1.13 MPa [118]. A two-tailed paired t-test was performed at a 5% confidence level to assess significant differences in moduli between steps. The modulus after the 1000 cycles was significantly lower than all other points in the loading protocol, except for the modulus after one impact following the recovery period. The modulus increased again after a subsequent impact loading step and returned to a non-significant difference to the value prior to cycling. The rest of the significant differences are shown in FIG. 42, denoted by asterisks. The modulus was significantly higher initially and immediately after the recovery period than after any impact load that followed the same day, but no significant differences between initial modulus and modulus after a recovery period existed. This shows that the hydrogel composite samples regained some of their stiffness during recovery. No significant differences exist between moduli following different impact loads, including those after cyclic compression and after a day of recovery. This shows that after an initial impact, the hydrogel composite maintains its stiffness after subsequent impacts, and that stiffness is also maintained after impact loads following cyclic loading and a recovery. This can be better seen by assessing the percent change between subsequent impacts steps, as shown in Table 10.

TABLE 9

Calculated compressive modulus values initially and after each loading step using a 2% to 12% strain range. All moduli remained within the acceptance criteria of 0.30 Mpa to 100 MPa.

| | Initial | Compressive Modulus (MPa) After Load Step: | | | | | |
|---|---|---|---|---|---|---|---|
| Sample # | Modulus (MPa) | One Impact | Three Impacts | 1000 Cycles | Cycles, Impact | Recovery Initial | Recovery, Impact |
| 1 | 1.36 | 1.15 | 1.06 | 0.80 | 1.00 | 1.51 | 1.23 |
| 2 | 1.76 | 1.36 | 1.29 | 0.98 | 1.21 | 1.39 | 1.07 |
| 3 | 1.77 | 1.34 | 1.32 | 1.03 | 1.30 | 1.42 | 1.20 |
| Average | 1.63 | 1.28 | 1.22 | 0.94 | 1.17 | 1.44 | 1.17 |
| SD | 0.24 | 0.11 | 0.14 | 0.12 | 0.15 | 0.06 | 0.08 |

TABLE 10

Percent change in compressive modulus after different impact steps compared to the previous impact step using a 2% to 12% strain range.

| Sample # | 1 Impact vs 3 Impacts | 3 Impacts vs Post Cycle Impact | Post Cycle Impact vs Post Recovery Impact |
|---|---|---|---|
| 1 | −8.3% | −5.4% | 22.6% |
| 2 | −4.7% | −6.5% | −11.6% |
| 3 | −1.2% | −1.5% | −7.3% |
| Average | −4.7% | −4.5% | 1.2% |
| SD | 3.5% | 2.6% | 18.6% |

Figure 43:
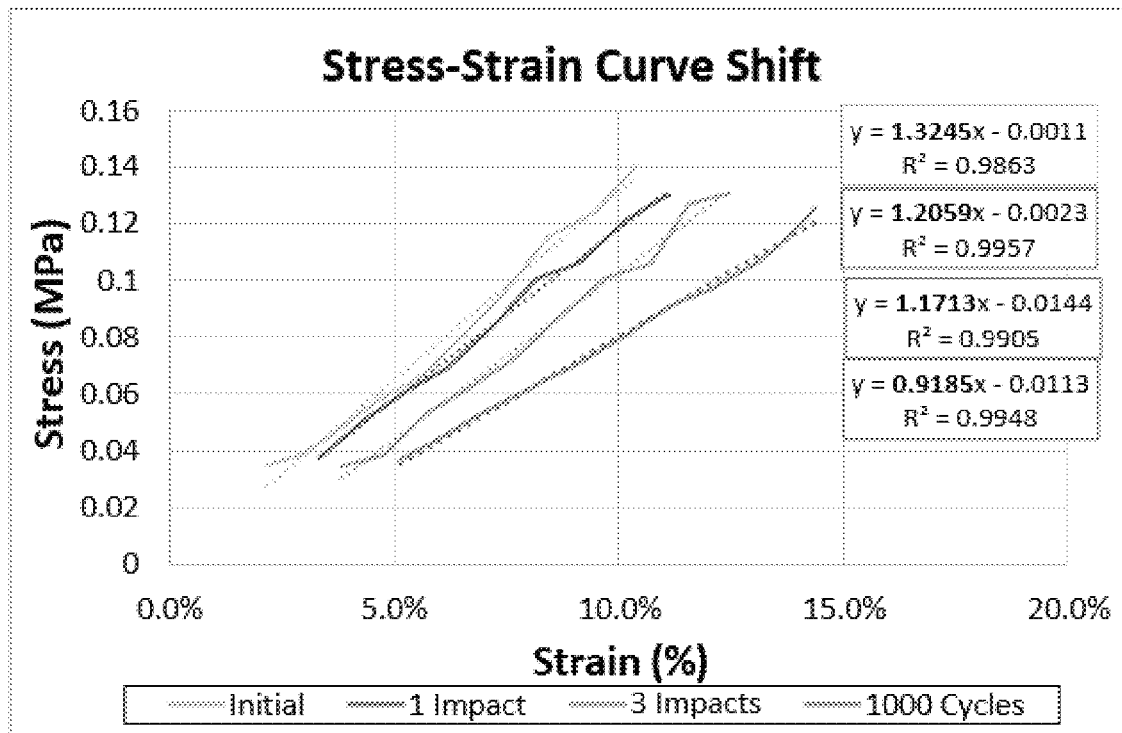
FIG. 43 shows a stress-strain curve shift during different steps of the loading protocol due to samples reducing in height and affecting the strain calculations. Data shown is for sample 1, and modulus values from the trendline equations are in bold font.
Figure 44:
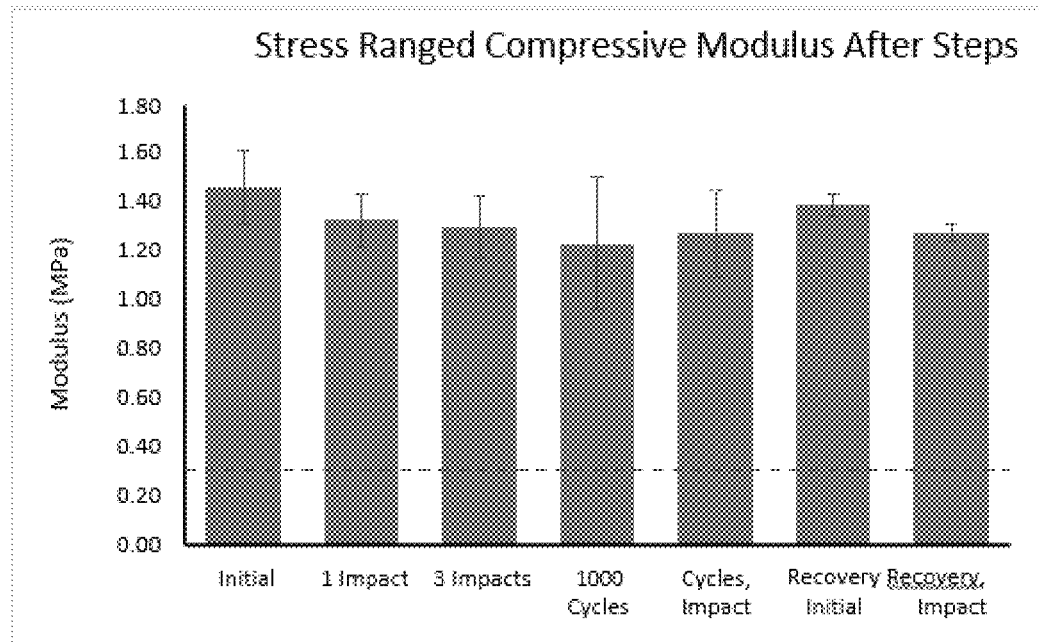
FIG. 44 shows a comparison of compressive moduli after each step in the compression loading protocol using a 0.03 MPa to 0.14 MPa stress range. No significant differences exist between any steps. The minimum specification of 0.30 MPa is shown in red.

Compressive Modulus Changes Using Stress Range: The shift of the stress-strain curves for shorter samples to the right in the later steps of the loading protocol, as described earlier, is shown in FIG. 43. To resolve this issue, compressive modulus values were also calculated in a linear portion of the conditioning stress-strain curves corresponding to a fixed strain range, 0.03 MPa to 0.14 MPa, as mentioned previously. After this fix, modulus values between steps became much closer to each other, as shown in FIG. 44 and Table 11. The initial modulus was still the highest at 1.46 MPa. The modulus after 1000 cycles was the lowest at 1.23 MPa and the modulus after recovery was the highest during the loading protocol at 1.39 MPa. Although the same trend for increasing and decreasing of the modulus values between steps exists after this method of modulus calculation, no significant differences exist between any steps after a two-tailed paired t-test at a 5% confidence level was employed. All moduli also remained within the acceptable range of 0.30 MPa to 100 MPa.

Without being wed to theory, an explanation for the modulus change trend is that after the impact loads or cycles, the PVA chains shift to allow channels for water to more easily flow through, reducing the friction of water moving through the matrix and in turn the stiffness. During recovery, the PVA chains shift back to their original conformation and the friction for water motion through the matrix is reintroduced.

TABLE 11

Calculated compressive modulus values initially and after each loading step using a 0.03 MPa to 0.14 MPa strain range. All moduli remained within the acceptance criteria of 0.30 MPa to 100 MPa.

| Sample # | Initial Modulus (MPa) | Compressive Modulus (MPa) After Load Step: | | | | |
|---|---|---|---|---|---|---|
| | | One Impact | Three Impacts | 1000 Cycles | Cycles, Impact | Recovery Initial | Recovery, Impact |
| 1 | 1.29 | 1.21 | 1.17 | 0.94 | 1.14 | 1.37 | 1.24 |
| 2 | 1.55 | 1.35 | 1.29 | 1.27 | 1.19 | 1.36 | 1.30 |
| 3 | 1.55 | 1.42 | 1.43 | 1.49 | 1.48 | 1.44 | 1.29 |
| Average | 1.46 | 1.33 | 1.30 | 1.23 | 1.27 | 1.39 | 1.28 |
| SD | 0.15 | 0.11 | 0.13 | 0.27 | 0.18 | 0.05 | 0.03 |

Compressive properties—sample height changes: The height change data for each sample after the first three impact loads and after 1000 cycles can be found in Table 12. The percent change in height after the impact loads (reduced by 2.8% of initial height) and after the cyclic loading (reduced by 1.6% of initial height) both remain under the acceptable criteria maximum of 5% axial deformation. The total height change when all loading steps are combined (reduced by 4.3%) also remains below the specification. After the 1000 cycles loading, additional impact loads did not cause any more height changes or deformation to any of the samples. This suggests that most, if not all, the height change or deformation occurs in the first few impacts and/or cyclic loadings. This could be because any air bubbles or voids in the hydrogel test samples are compacted or pushed out of the hydrogel surface in the initial loadings, or the hydrogel wasn't loaded enough times after the cycles to find that more height change could occur. If the hydrogels in fact do not experience any more deformation after a few initial loadings, an artificial meniscus implant could be conditioned into its final shape and size prior to use in a patient.

TABLE 12

Height changes of each sample after the first 3 impact loads and after 1000 cycles. No additional height changes occurred following the cycles, and the total height change remains below the specification of 5%.

| | | After 3 Impact Loads | | After 1000 Cycles | | |
|---|---|---|---|---|---|---|
| Sample # | Initial Height (mm) | Height Change (mm) | % Change | Height Change (mm) | % Change | Total % Change |
| 1 | 4.50 | −0.10 | −2.2% | −0.10 | −2.2% | −4.4% |
| 2 | 3.80 | −0.10 | −2.6% | −0.050 | −1.3% | −3.9% |
| 3 | 4.30 | −0.15 | −3.5% | −0.050 | −1.2% | −4.7% |
| Average | 4.20 | −0.12 | −2.8% | −0.067 | −1.6% | −4.3% |
| SD | 0.36 | 0.029 | 0.65% | 0.029 | 0.57% | 0.36% |

Figure 45:
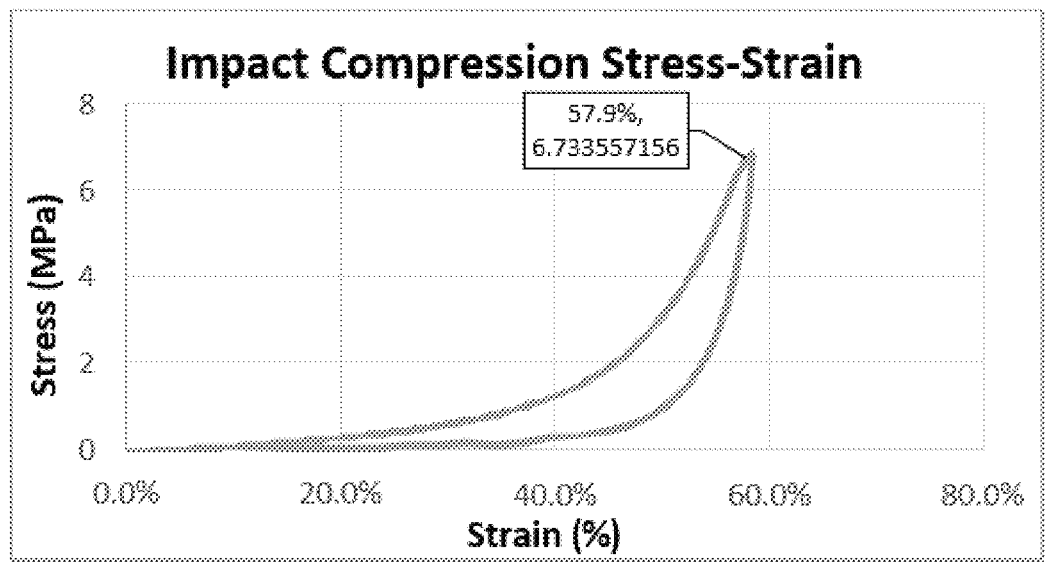
FIG. 45 shows a plot of stress versus strain during an impact load where the impact stress value of 6.73 is extracted at a 57.9% strain. Data is from impact 3 of sample 2.
Figure 46:
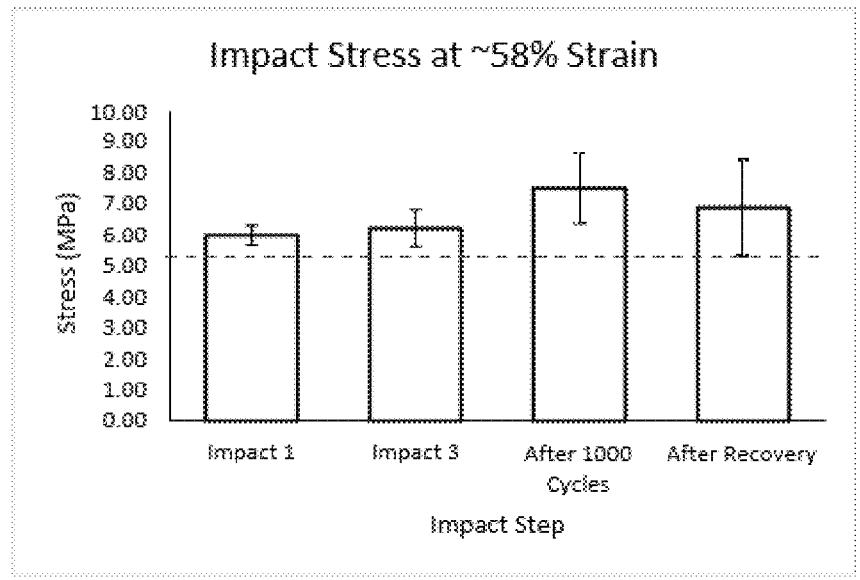
FIG. 46 shows a comparison of the average impact stresses for each step in the loading protocol, with the 5.4 MPa threshold shown as a red dashed line. No significant differences among steps exist.

Compressive Stress During Impacts: The samples were loaded to at least 5.4 MPa during all impact tests to simulate a worst-case type load on the natural meniscus. While performing the impact tests, the testing machine would occasionally compress the sample farther and impart a higher stress on the sample than intended. To correct for this and to draw comparisons, the impact stress level at a specific strain was found for each sample, which coincided with the lowest-strained step that sample experienced in the loading protocol. For example, if a sample was loaded to 58% strain in one impact load and over 58% strain in the remaining impact loads, the stress level at 58% strain was recorded for each step (see FIG. 45). These values are reported for each sample at different impact steps in Table 13, along with the averages and standard deviations among all samples, which is also shown in FIG. 46 for comparison. The second impact load for the samples is not reported because little change occurred between the first and third impacts and the results did not reveal any useful information. Every impact load for all samples exceeded the 5.4 MPa needed to reach the specification, with some reaching as high as 10.8 MPa. A two-tailed paired t-test at a 5% confidence level was performed to determine if the impact stresses were statistically different between the different steps, but none were found to be significant. This indicates that the hydrogel material can withstand these high stress levels repeatedly, and shows that the samples likely had no damage that could not be visually seen after the impact loads and 1000 cycle load.

TABLE 13

Calculated impact stress values for each sample at different steps in the loading protocol.

| | Stress Level (MPa) at approx. 58% strain | | | |
|---|---|---|---|---|
| Sample # | Impact 1 | Impact 3 | After 1000 Cycles | After Recovery |
| 1 | 6.23 | 5.57 | 7.12 | 8.65 |
| 2 | 5.62 | 6.73 | 6.61 | 5.83 |
| 3 | 6.12 | 6.34 | 8.78 | 6.14 |
| Average | 5.99 | 6.21 | 7.50 | 6.87 |
| SD | 0.33 | 0.59 | 1.13 | 1.55 |

Figure 47:
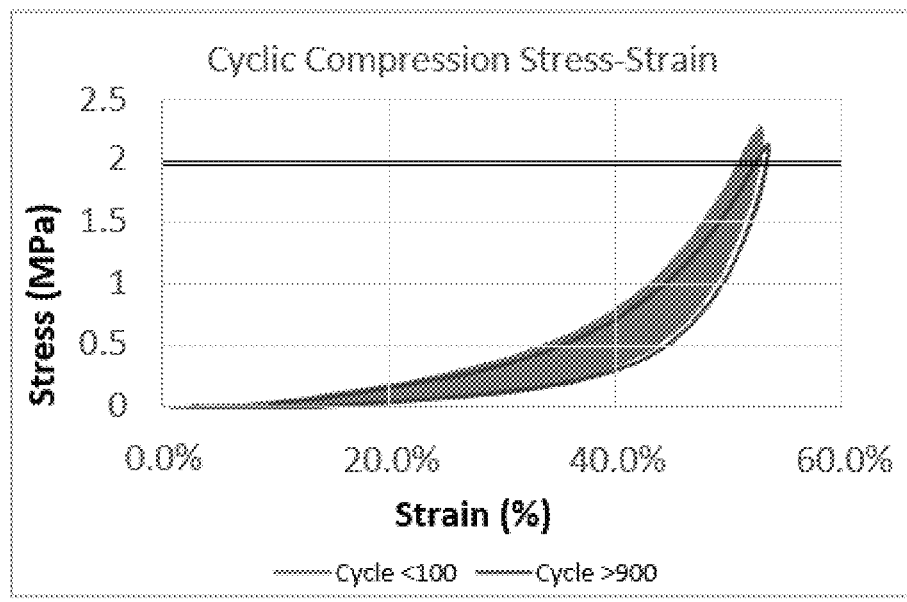
FIG. 47 shows an example plot of stress versus strain for a cycle at less than 100 cycles and a cycle at greater than 900 cycles during cyclic compression testing with the stress level remaining above the 2.0 MPa specification, shown as the black dashed line.

Compressive Stress During Cycles: The samples were loaded to at least 2.0 MPa for 1000 cycles to simulate the load experienced by the medial meniscus during gait. The samples were loaded to a stress level slightly higher than the 2.0 MPa value to ensure that even at the end of the cycles, they were being loaded to the 2.0 MPa specification. The stress level on all samples remained above this value by the end of the cycles, as shown in FIG. 47. Without being wed to theory, this slight drop in stress level from early to later cycles is likely due to the samples losing small amounts of axial height from the constantly repeated compression, which temporarily forces water out of the hydrogel matrix to cause the height change. From manual caliper measurements of the samples, the samples recovered some of this height change during the recovery periods (data not shown), but the exact amount is unknown since the change in preload height could not be recorded between different days.

Figure 48:
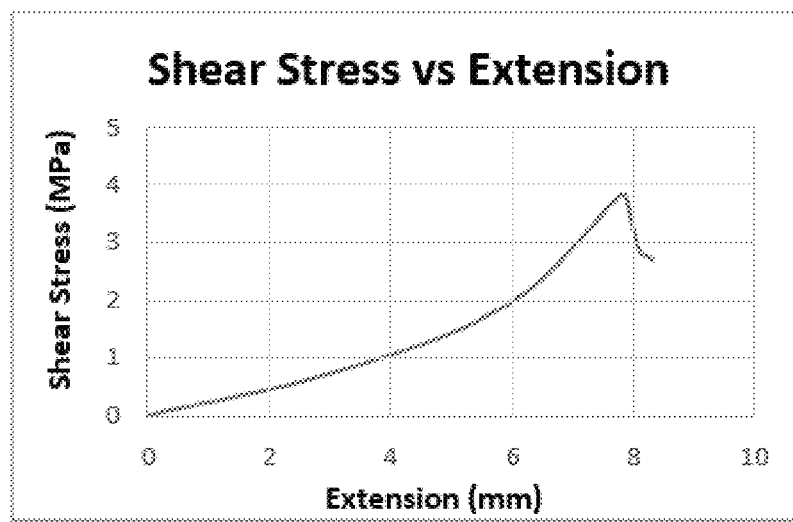
FIG. 48 shows a plot of shear stress versus extension of the test grips, where shear strength is the maximum shear stress value. Data from sample 4.
Figure 49:
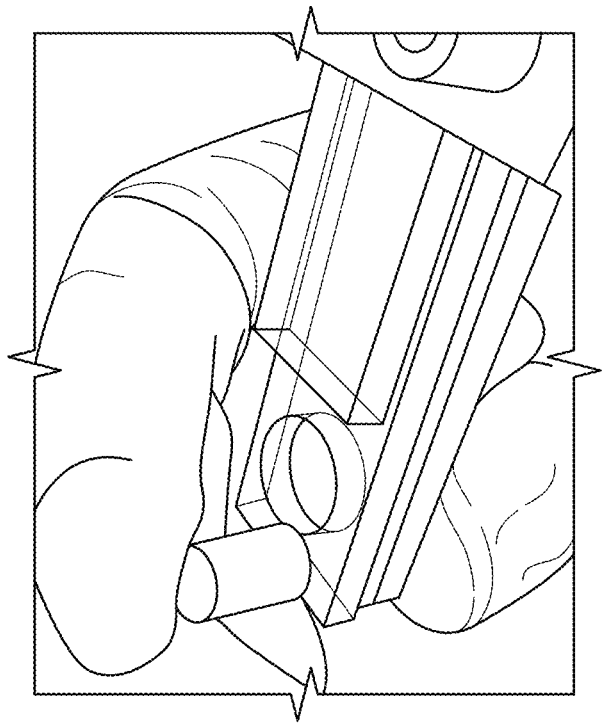
FIG. 49 shows a sample failure mode is shear within the custom testing apparatus when the two pieces are pulled in tension.

Shear strength: Cylindrical samples of 40 wt % PVA were pulled in tension perpendicularly to the sample's axial axis until shear failure using a custom two-piece testing apparatus to determine shear strength. An example plot of the shear data for one sample can be seen in FIG. 48, where the maximum shear stress is the shear strength. Failure was confirmed to occur in shear (see FIG. 49). The shear strength of each sample, along with the average and standard deviation values, can be found in Table 14. With an average shear strength of 3.7 MPa, these samples exceed the acceptable criteria of 0.75 MPa for an artificial meniscus implant by over 3 times, so the specification is met.

TABLE 14

Shear strength values for each sample calculated from the maximum recorded load and sample cross sectional area.

| Sample # | Max Load (N) | Area (mm$^2$) | Shear Strength (MPa) |
|---|---|---|---|
| 1 | 347.5 | 84.9 | 4.09 |
| 2 | 324.3 | 86.6 | 3.74 |
| 3 | 277.8 | 88.2 | 3.15 |
| 4 | 325.7 | 84.9 | 3.83 |
| Average | | | 3.70 |
| SD | | | 0.48 |

Figure 50:
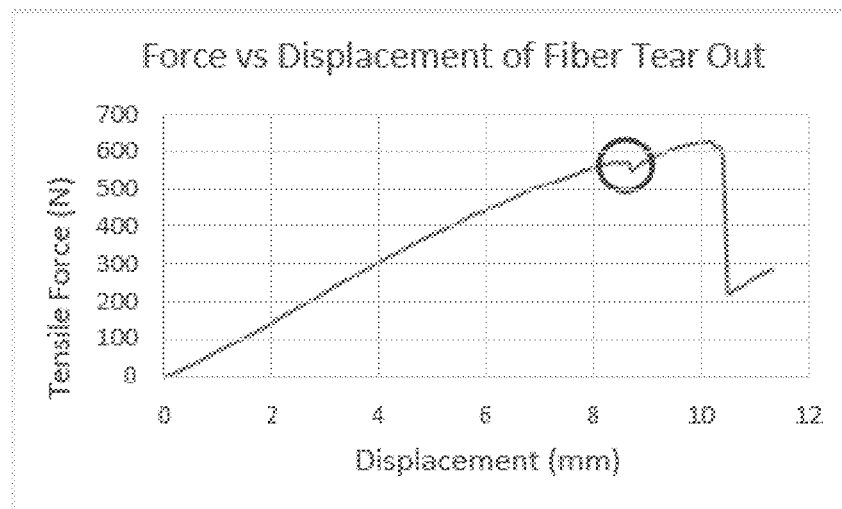
FIG. 50 shows a plot of force versus displacement for a fiber tear out test with the fiber tear out strength defined as the point of plastic deformation, outlined with a red circle. Data shown is for sample 3.
Figure 51:
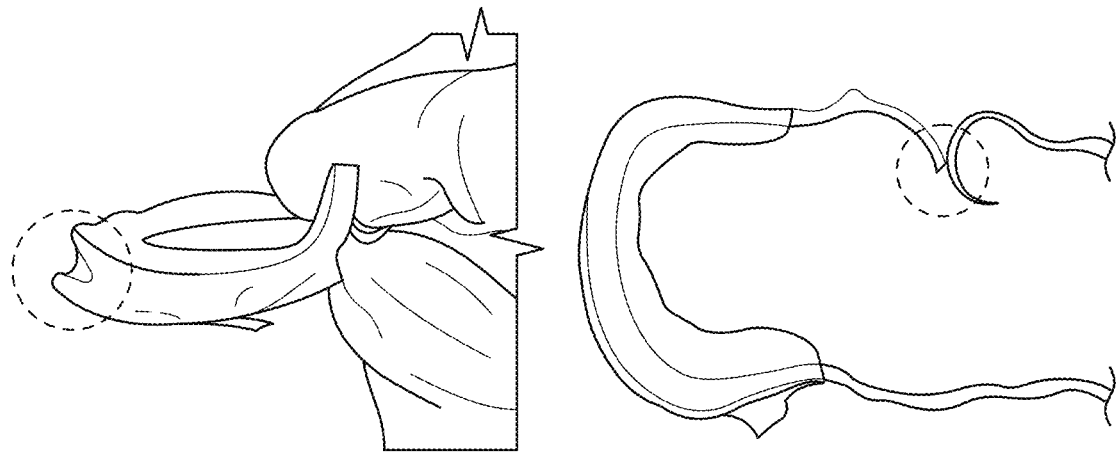
FIG. 51 shows implant failure modes, highlighted with red circles, of peripheral concavity (left) and fiber fracture (right) from fiber tear out tests.

Fiber Tear Out Strength: Prototype-shaped 40 wt % hydrogel composite samples were pulled by the reinforcing fiber extensions in tension while housed in a custom testing apparatus designed to simulate a knee joint. Samples were pulled in tension this way to mimic the hoop stresses that develop in the meniscus due to its firm attachment at the horns. The fiber tear out strength was assessed by finding the maximum tensile load reached before any plastic deformation in the sample, which was defined as a sudden decrease in force or obvious change in the slope of the force-displacement curve, as shown in FIG. 50. All prototype samples failed either by fiber fracture outside of the hydrogel area, or by deformation around the periphery of the prototype, where the originally straight peripheral wall of the implant became concave as the fibers were being pulled away from it and into the bulk hydrogel. An example of a prototype that failed in both ways can be seen in FIG. 51. Fiber tear out strength for each sample, along with average and standard deviation values, are reported in Table 15. The 531 N value for average fiber tear out strength easily surpasses the acceptance criteria of 140N, by almost four times. This result suggests that this implant would be able to withstand the tensile and hoop stresses that are normally present in the meniscus without interfacial composite failure and the reinforcing fibers moving within the hydrogel matrix.

TABLE 15

Fiber tear out strength for each sample.

| Sample # | Fiber Tear Out Strength (N) |
|---|---|
| 1 | 642 |
| 2 | 400 |
| 3 | 573 |
| 4 | 511 |
| Average | 531 |
| SD | 103 |

Figure 52:
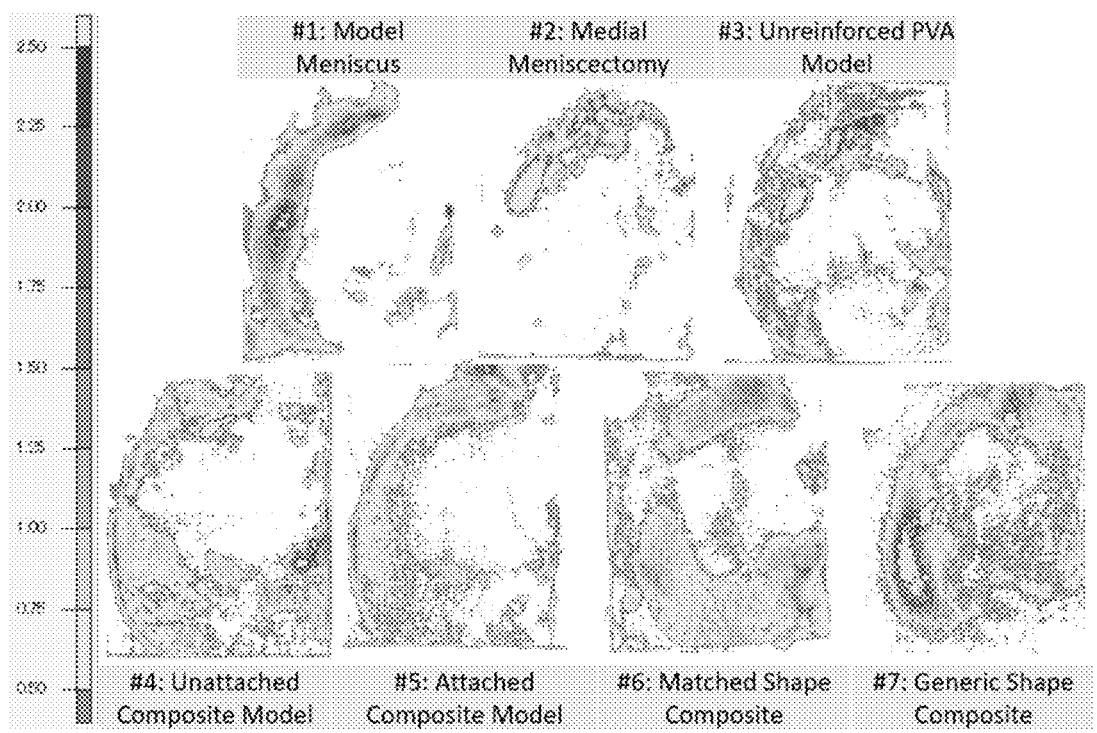
FIG. 52 shows a visual analysis of pressure distribution for each condition and color key for contact pressure in MPa.
Figure 53:
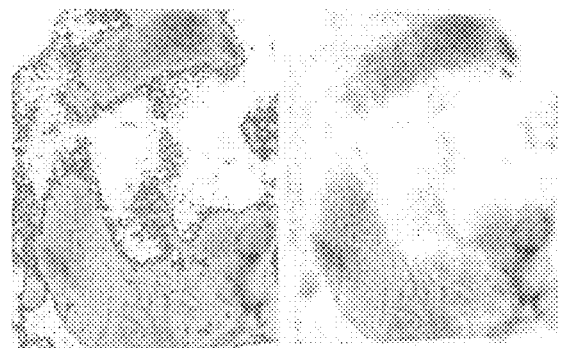
FIG. 53 shows an original visual analysis image #6 with green areas showing less than 0.5 MPa contact pressure (left) and image after green area removal for average pressure calculation (right).

Pressure Distribution—Visual and Numerical Analyses: Seven different conditions or prototypes were assessed for contact pressure distribution on the tibial plateau of a functional knee model while under a 1000 N compressive joint load. A visual analysis of the pressure distributions for all conditions are shown in FIG. 52 and a numerical analysis of the average and maximum pressures for each condition are shown in Table 16, along with the percent of the contact area that had a pressure of 2.5 MPa or greater. The 2.5 MPa value was the upper limit for the visual analysis of the pressure film used, although the maximum pressure could be read up to 3.06 MPa in the numerical analysis (Table 16). In the numerical analysis, the areas of a contact pressure less than 0.5 MPa, shown as green in FIG. 52, were removed for the average pressure calculation (see FIG. 53). This was done because pressures that low were more likely due to the contact from inserting the film into the setup rather than the actual test, and therefore skewed the results. Any maximum pressure values that are reported as 3.06 MPa are in fact greater than that value, since 3.06 MPa was the highest pressure that the pressure indicating film could measure. This upper limit for the pressure film also influenced the average pressure calculation. Since 3.06 MPa is the maximum value used in the average pressure calculation, the average pressures for conditions that experienced any area at this maximum would realistically be greater than the reported values.

TABLE 16

Quantitative analysis of conditions for average and maximum pressures, and the percent area of contact pressure greater than 2.5 MPa.

| ID # | Condition | Avg Pressure (MPa) | Max Pressure (MPa) | % Area at >2.5 MPa |
|---|---|---|---|---|
| 1 | Model Meniscus | 1.09 | 3.04 | 0.82 |
| 2 | Medial Meniscectomy | 1.38 | >3.06 | 18.8 |
| 3 | Unreinforced PVA Model | 1.10 | >3.06 | 8.50 |
| 4 | Unattached Composite Model | 0.89 | >3.06 | 2.23 |
| 5 | Attached Composite Model | 0.80 | 2.82 | 0.02 |
| 6 | Matched Shape Composite | 0.89 | 2.50 | 0.00 |
| 7 | Generic Shape Composite | 1.08 | >3.06 | 7.53 |

Figure 54:
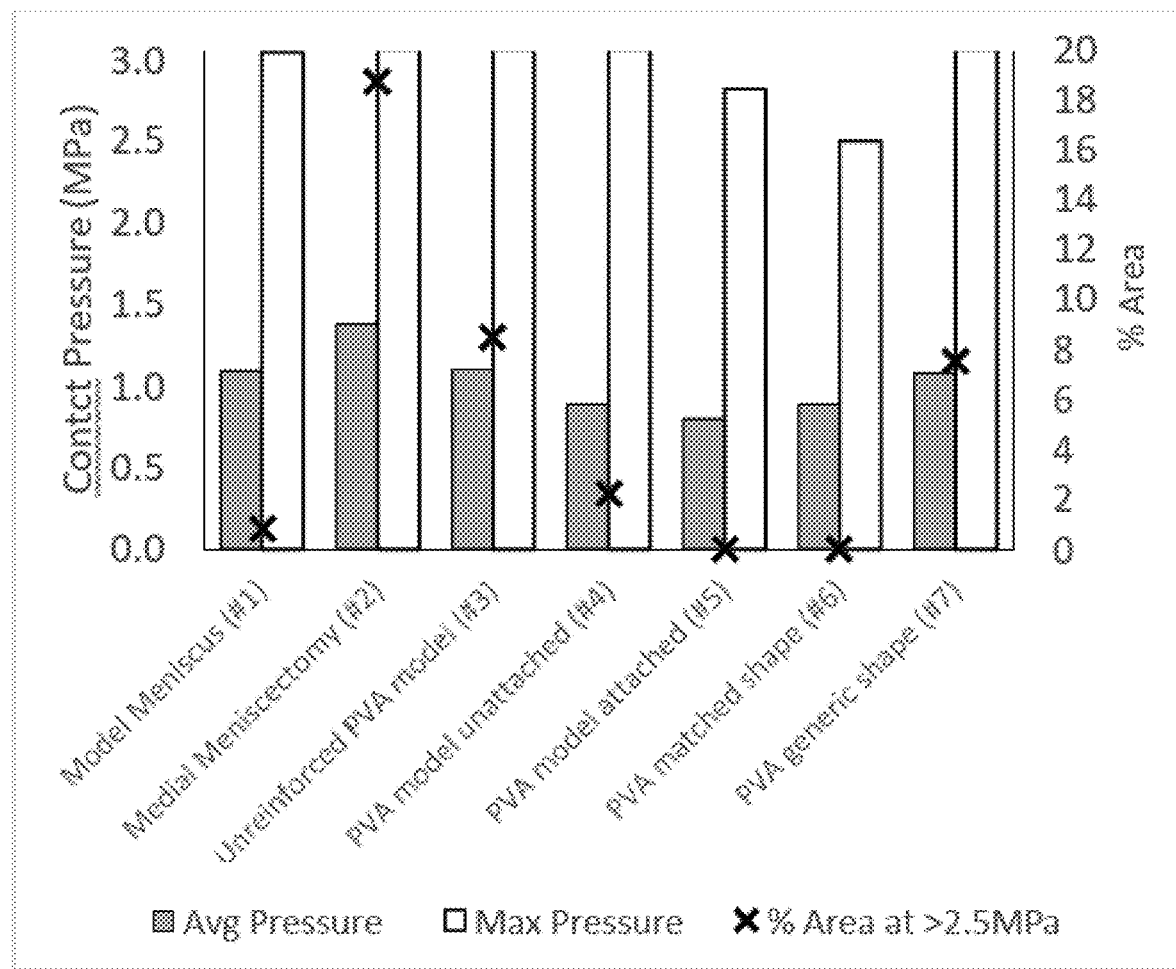
FIG. 54 shows a comparison for all conditions of average and max contact pressures (left axis), where no line at the top of the max pressure bars signifies an unknown value above 3.06 MPa, and the percent of the contact area at a pressure greater than 2.5 MPa (right axis). Results are shown for all conditions described in Table 6.

Pressure Distribution—Comparison Between Conditions: A comparison between all conditions can be seen in FIG. 54, showing contact pressure on the left axis and percent area on the right axis. Conditions that had areas at the maximum measurable pressure, 3.06 MPa, have open bars in the top of the chart to depict an unknown maximum value. These conditions included the medial meniscectomy (#2), the unreinforced PVA model-shaped prototype (#3), the unattached model-shaped composite prototype (#4), and the generic-shaped CAD designed composite prototype (#7). It is important to note that for these four conditions, the reported average pressures are likely higher than those shown here due to the upper limit for pressure film measurement affecting the calculation. There was also noticeable radial extrusion in the unreinforced PVA prototype and in the unattached composite implant. All other composite prototypes experienced slight extrusion, but the attachment of these implants prevented them from extruding very much.

The medial meniscectomy (#2) was the worst overall condition tested, with the highest average pressure at 1.38 MPa, the highest contact area greater than 2.5 MPa pressure at 18.8%, and peak pressure exceeding the maximum measurable value of 3.06 MPa. This result was to be expected since there is no meniscus prototype in the meniscectomy condition to share the load on the medial side.

The unreinforced PVA model (#3) had the second highest average pressure at 1.10 MPa and the second highest percentage of high pressure contact area at 8.50%. This result confirms that no reinforcements in the hydrogel prototype leaves considerable risk for high contact pressure areas and potential cartilage damage.

The generic shaped composite prototype designed in CAD (#7) came in the middle with the fourth highest average at 1.08 MPa, but had the third highest area at high contact pressure with 7.53%. This suggests that size and shape are important parameters to prevent high pressure areas, which can cause damage to the implant or knee joint. The high percentage of area at the maximum measurable pressure also means the average pressure is probably higher than the 1.08 MPa reported.

The unattached, model-shaped composite prototype (#4) still reached the maximum readable pressure, but had an average pressure of 0.89 MPa (one of the lowest tested) and 2.23% of area at a high contact pressure. Although the average pressure was tied for the second lowest, the areas of maximum pressure would likely make this value increase if the true peak contact pressures could be determined. This shows that even if a hydrogel meniscus implant has reinforcement, risk of high contact pressure is still present if there is no attachment within the joint space.

The original model meniscus (#1) did not reach the maximum measurable pressure, but was very close at 3.04 MPa. Although it had the third lowest percent of high pressure areas at 0.82%, it also had the third highest average pressure at 1.09 MPa. This result shows that even if the shape and size of the prototype is closely fit to the joint, the material of the implant and attachment within the joint are still key parameters for proper pressure distribution.

Only two of the prototypes tested met the preferred acceptance criteria of less than 3 MPa maximum pressure for a 1000N joint load. These were the attached, model-shaped composite (#5) and the CAD-designed, matched shape composite (#6).

The attached, model-shaped composite prototype (#5) had the lowest average pressure at 0.80 MPa, the second lowest maximum pressure at 2.82 MPa, and the second lowest percent of high contact pressure areas at 0.02%. This prototype performed better than all of those previously mentioned in all the categories examined. This shows that a proper combination of reinforcements, size and shape, firm attachment, and material for a meniscus implant can greatly improve contact mechanics in a knee joint and reduce the risk of cartilage damage over the medial meniscectomy condition.

The matched shape composite prototype designed in CAD (#6) had the second lowest average pressure of 0.89 MPa, the lowest maximum pressure of 2.50 MPa, and an essentially negligible area of contact pressure over 2.50 MPa to give a 0.00% value. Although the average pressure for this prototype was higher than its model-shaped counterpart, the contact pressure was better distributed over a large area and the peak pressure remained below 2.50 MPa everywhere. The high magnitude pressure areas on the articular cartilage are believed to be responsible for the biological changes in the cartilage and bone that may lead to osteoarthritis [125]. Therefore, a lower peak pressure may be more crucial than a lower average pressure for a meniscal implant. The improvement in contact mechanics with this implant when compared to the generic shaped implant (#7) demonstrates that the risk of high contact pressure and resulting cartilage damage can be reduced if a proper implant shape is used. On the other hand, this prototype also performed as well if not better than the model-shaped prototype (#5), so an exact size and shape match, including contours of the tibial plateau at the base of the implant, is not needed for proper contact mechanics. This finding shows that while a meniscus implant cannot just be a generic shape, it also does not need to be customized for each patient. A reasonable number of implant size and shape variations may be sufficient for most patients needing a meniscus replacement.

Pressure Distribution—Higher Joint Loads: The best performing prototype under a 1000 N load in terms of contact mechanics was determined to be the matched-shape, CAD designed implant (#6). To assess its performance under higher, more physiologically relevant gait loads, the prototype was loaded to 1500 N (for comparison with literature values) and to 2200 N (gait load for average person) using the original pressure indicating film with the range of 0.5 MPa to 2.5 MPa, and with a higher pressure indicating film with the range of 2.5 MPa to 10 MPa.

Figure 55:
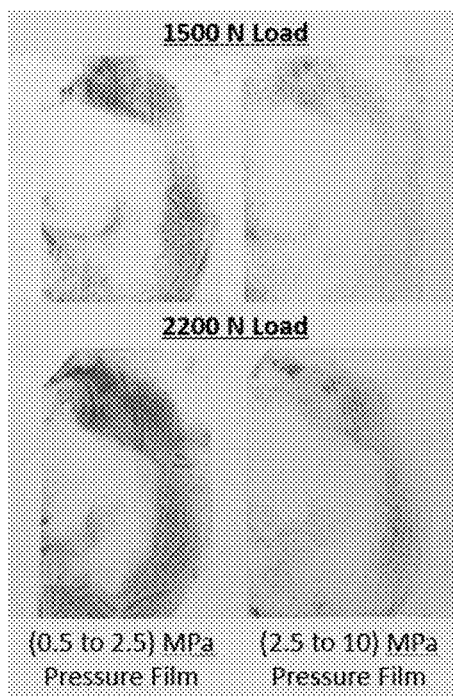
FIG. 55 shows a photo of two ranges of pressure indicating film after testing the matched shape composite prototype at two higher joint loads, such as gait conditions. The 1500N and 2200N (gait) loads produced max contact stresses of about 4 MPa and 6 MPa, respectively, determined by color correlation charts.

These results are shown in FIG. 55, where a color correlation chart was used to estimate the peak contact pressure values instead of a digital analysis. At a load of 1500 N, the higher ranged film shows little to no dark colors, with a maximum pressure value estimated at less than 4 MPa, which is the same as a natural meniscus at a 1500N joint load [122]. At a load of 2200 N, small darker areas can be seen and these spots were estimated to be about 6.5 MPa of contact pressure. These spots of 6.5 MPa peak pressure remain at the same level or below values found in the literature for the natural intact meniscus at peak gait cycle loads and meet the acceptance criteria of less than 7.4 MPa peak pressure [123]. The 6.5 MPa peak pressure for the implant at 2200N is also much less than the peak pressure for meniscectomy conditions at gait loading, which is about 10 MPa [123]. Therefore, the contact mechanics at higher joint loads using the matched shape composite prototype is consistent with the natural meniscus and an improvement over alternative treatment conditions. In addition, these high-pressure spots could potentially be eliminated with more careful attachment of the prototype, since the attachment fibers were just threaded through arbitrary bone tunnels and tied around the outside of the model's tibia in these tests.

A summary of the acceptance criteria and measured values is found in Table 17, below.

TABLE 17

Acceptance criteria and measured values from the mechanical evaluation. All specifications were met.

| Design Specification | Acceptance Criteria | Measured Value |
|---|---|---|
| Tensile Strength | >12 MPa | 20.2 MPa |
| Tensile Modulus | 50 MPa to 1000 MPa | 589 MPa |
| Cyclic Tension Resistance (After 1000 Cycles) | Tensile strength: >12 MPa Tensile Modulus: 50 MPa to 1000 MPa | Tensile strength: 21.9 MPa Tensile Modulus: 709 MPa |
| Compressive Modulus | 0.30 MPa to 100 MPa | 1.63 MPa |
| Impact Load Resistance (After 3 Impact Loads) | Height Change: <5% Compressive Modulus: 0.30 MPa to 100 MPa | Height Change: 2.8% Compressive Modulus: 1.22 MPa |
| Cyclic Compression Resistance (After 1000 Cycles) | Height Change: <5% Compressive Modulus: 0.30 MPa to 100 MPa | Height Change: 1.6% Compressive Modulus: 0.94 MPa |
| Shear Strength | >0.75 MPa | 3.7 MPa |
| Fiber Tear Out Strength | >140N | 531N |
| Peak Contact Pressure at Standing Load | <3 MPa | 2.5 MPa |
| Peak Contact Pressure at Gait Load | <7.4 MPa | 6.5 MPa |

While the invention has been described with reference to particular embodiments and implementations, it will understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular implementations disclosed herein, but that the invention will include all implementations falling within the scope of the appended claims.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various implementations with various modifications as are suited to the particular use contemplated.

REFERENCES

[1] T. Kusayama, C. D. Harner, G. J. Carlin, J. W. Xerogeanes, and B. A. Smith, "Anatomical and biomechanical characteristics of human meniscofemoral ligaments.," *Knee Surg. Sports Traumatol. Arthrosc.*, vol. 2, no. 4, pp. 234-7, 1994.

[2] K. R. Stone, A. Freyer, T. Turek, A. W. Walgenbach, S. Wadhwa, and J. Crues, "Meniscal Sizing Based on Gender, Height, and Weight," *Arthrosc. —J. Arthrosc. Relat. Surg.*, vol. 23, no. 5, pp. 503-508, 2007.

[3] C. R. Clark and J. A. Ogden, "Development of the menisci of the human knee joint. Morphological changes and their potential role in childhood meniscal injury.," *J. Bone Joint Surg. Am.*, vol. 65, no. 4, pp. 538-47, April 1983.

[4] S. P. Arnoczky and R. F. Warren, "Microvasculature of the human meniscus," *Am. J. Sports Med.*, vol. 10, no. 2, pp. 90-95, March 1982.

[5] C. S. Proctor, M. B. Schmidt, R. R. Whipple, M. A. Kelly, and V. C. Mow, "Material properties of the normal medial bovine meniscus," *J. Orthop. Res.*, vol. 7, no. 6, pp. 771-782, 1989.

[6] J. Herwig, E. Egner, and E. Buddecke, "Chemical changes of human knee joint menisci in various stages of degeneration.," *Ann. Rheum. Dis.*, vol. 43, no. 4, pp. 635-40, August 1984.

[7] I. D. McDermott, S. D. Masouros, and A. A. Amis, "Biomechanics of the menisci of the knee," *Curr. Orthop.*, vol. 22, no. 3, pp. 193-201, 2008.

[8] A. Beaupré, R. Choukroun, R. Guidouin, R. Garneau, H. Gérardin, and A. Cardou, "Knee menisci. Correlation between microstructure and biomechanics.," *Clin. Orthop. Relat. Res.*, no. 208, pp. 72-5, July 1986.

[9] P. G. Bullough, L. Munuera, J. Murphy, and A. M. Weinstein, "The strength of the menisci of the knee as it relates to their fine structure.," *J. Bone Joint Surg. Br.*, vol. 52, no. 3, pp. 564-7, August 1970.

[10] A. J. S. Fox, A. Bedi, and S. A. Rodeo, "The Basic Science of Human Knee Menisci," *Sport. Heal. A Multidiscip. Approach*, vol. 4, no. 4, pp. 340-351, 2012.

[11] D. C. Fithian, M. A. Kelly, and V. C. Mow, "Material properties and structure-function relationships in the menisci.," *Clin. Orthop. Relat. Res.*, no. 252, pp. 19-31, March 1990.

[12] D. L. Skaggs, W. H. Warden, and V. C. Mow, "Radial tie fibers influence the tensile properties of the bovine medial meniscus," *J. Orthop. Res.*, vol. 12, no. 2, pp. 176-185, March 1994.

[13] E. A. Makris, P. Hadidi, and K. A. Athanasiou, "The knee meniscus: Structure-function, pathophysiology, current repair techniques, and prospects for regeneration," *Biomaterials*, vol. 32, no. 30, pp. 7411-7431, 2011.

[14] A. S. Voloshin and J. Wosk, "Shock absorption of meniscectomized and painful knees: a comparative in vivo study.," *J. Biomed. Eng.*, vol. 5, no. 2, pp. 157-61, April 1983.

[15] H. Kurosawa, T. Fukubayashi, and H. Nakajima, "Load-bearing mode of the knee joint: physical behavior of the knee joint with or without menisci.," *Clin. Orthop. Relat. Res.*, no. 149, pp. 283-90, June 1980.

[16] I. M. Levy, P. A. Torzilli, and R. F. Warren, "The effect of medial meniscectomy on anterior-posterior motion of the knee.," *J. Bone Joint Surg. Am.*, vol. 64, no. 6, pp. 883-8, July 1982.

[17] K. Messner and J. Gao, "The menisci of the knee joint. Anatomical and functional characteristics, and a rationale for clinical treatment.," *J. Anat.*, vol. 193 (Pt 2), pp. 161-78, August 1998.

[18] W. R. Krause, M. H. Pope, R. J. Johnson, and D. G. Wilder, "Mechanical changes in the knee after meniscectomy.," *J. Bone Joint Surg. Am.*, vol. 58, no. 5, pp. 599-604, July 1976.

[19] R. S. Jones et al., "Direct measurement of hoop strains in the intact and torn human medial meniscus.," *Clin. Biomech. (Bristol, Avon)*, vol. 11, no. 5, pp. 295-300, July 1996.

[20] K. A. Athanasiou and J. Sanchez-Adams, *Engineering the Knee Meniscus*. Morgan & Claypool, 2009.

[21] M. Drakos and A. Allen, "Meniscal Structure, Function, Repair, and Replacement," *Oncology and Basic Science*, 2016. [Online]. Available: https://oncohemakey.com/meniscal-structure-function-repair-and-replacement/. [Accessed: 8 Apr. 2018].

[22] A. A. Amis, A. M. J. Bull, and I. D. McDermott, "Caracteristiques biomecaniques des ligaments et des menisques du genou [Biomechanical function of knee ligaments and menisci]," in *Pathologic ligamentaire du genou*, no. 2, Springer Verlag, 2004, pp. 45-60.

[23] P. E. Greis, D. D. Bardana, M. C. Holmstrom, and R. T. Burks, "Meniscal injury: I. Basic science and evaluation.," *J. Am. Acad. Orthop. Surg.*, vol. 10, no. 3, pp. 168-76.

[24] N. Maffulli, U. G. Longo, S. Campi, and V. Denaro, "Meniscal tears.," *Open access J. Sport. Med.*, vol. 1, pp. 45-54, April 2010.

[25] L. S. Lohmander, P. M. Englund, L. L. Dahl, and E. M. Roos, "The Long-term Consequence of Anterior Cruciate Ligament and Meniscus Injuries," *Am. J. Sports Med.*, vol. 35, no. 10, pp. 1756-1769, October 2007.

[26] I. D. McDermott and A. A. Amis, "The consequences of meniscectomy," *J. Bone Joint Surg. Br.*, vol. 88-B, no. 12, pp. 1549-1556, December 2006.

[27] K. Messner and J. Gillquist, "Prosthetic replacement of the rabbit medial meniscus," *J. Biomed. Mater. Res.*, vol. 27, no. 9, pp. 1165-1173, September 1993.

[28] P. Verdonk and P. Vererfve, "Traumatic Lesions: Stable Knee, ACL Knee," in *The Meniscus*, Berlin, Heidelberg: Springer Berlin Heidelberg, 2010, pp. 45-49.

[29] I. P. Terzidis, A. Christodoulou, A. Ploumis, P. Givissis, K. Natsis, and M. Koimtzis, "Meniscal Tear Characteristics in Young Athletes with a Stable Knee," *Am. J. Sports Med.*, vol. 34, no. 7, pp. 1170-1175, July 2006.

[30] M. T. Hirschmann and N. F. Friederich, "Classification: Discoid Meniscus, Traumatic Lesions," in *The Meniscus*, Berlin, Heidelberg: Springer Berlin Heidelberg, 2010, pp. 241-246.

[31] W. E. GarrettJr. et al., "American Board of Orthopaedic Surgery Practice of the Orthopaedic Surgeon: Part-II, Certification Examination Case Mix," *J. Bone Jt. Surg.*, vol. 88, no. 3, p. 660, March 2006.

[32] M. Majewski, H. Susanne, and S. Klaus, "Epidemiology of athletic knee injuries: A 10-year study," *Knee*, vol. 13, no. 3, pp. 184-188, June 2006.

[33] A. C. T. Vrancken, P. Buma, and T. G. Van Tienen, "Synthetic meniscus replacement: A review," *Int. Orthop.*, vol. 37, no. 2, pp. 291-299, 2013.

[34] A. B. Nielsen and J. Yde, "Epidemiology of acute knee injuries: a prospective hospital investigation.," *J. Trauma*, vol. 31, no. 12, pp. 1644-8, December 1991.

[35] T. D. Lauder, S. P. Baker, G. S. Smith, and A. E. Lincoln, "Sports and physical training injury hospitalizations in the army.," *Am. J. Prev. Med.*, vol. 18, no. 3 Suppl, pp. 118-28, April 2000.

[36] J. C. Jones, R. Burks, B. D. Owens, R. X. Sturdivant, S. J. Svoboda, and K. L. Cameron, "Incidence and risk factors associated with meniscal injuries among active-duty US military service members.," *J. Athl. Train.*, vol. 47, no. 1, pp. 67-73.

[37] F. A. Barber and J. E. McGarry, "Meniscal Repair Techniques," *Sports Med. Arthrosc.*, vol. 15, no. 4, pp. 199-207, December 2007.

[38] P. Beaufils and N. Pujol, "Meniscal repair: Technique," *Orthop. Traumatol. Surg. Res.*, vol. 104, no. 1, pp. S137-S145, February 2018.

[39] S. C. Mordecai, N. Al-Hadithy, H. E. Ware, and C. M. Gupte, "Treatment of meniscal tears: An evidence based approach.," *World J. Orthop.*, vol. 5, no. 3, pp. 233-41, July 2014.

[40] S. P. Arnoczky and R. F. Warren, "Microvasculature of the human meniscus," *Am. J. Sports Med.*, vol. 10, no. 2, pp. 90-95, March 1982.

[41] R. Seil and D. Pape, "Meniscal Repair: Biomechanics," in *The Meniscus*, Berlin, Heidelberg: Springer Berlin Heidelberg, 2010, pp. 107-117.

[42] B. E. Baker, A. C. Peckham, F. Pupparo, and J. C. Sanborn, "Review of meniscal injury and associated sports," *Am. J. Sports Med.*, vol. 13, no. 1, pp. 1-4, January 1985.

[43] A. Hede, D. B. Jensen, P. Blyme, and S. Sonne-Holm, "Epidemiology of meniscal lesions in the knee. 1,215 open operations in Copenhagen 1982-84.," *Acta Orthop. Scand.*, vol. 61, no. 5, pp. 435-7, October 1990.

[44] T. J. FAIRBANK, "Knee joint changes after meniscectomy.," *J. Bone Joint Surg. Br.*, vol. 30B, no. 4, pp. 664-70, November 1948.

[45] A. M. Ahmed and D. L. Burke, "In-vitro measurement of static pressure distribution in synovial joints—Part I: Tibial surface of the knee," *J. Biomech. Eng.*, vol. 105, no. 3, pp. 216-225, 1983.

[46] M. E. Baratz, F. H. Fu, and R. Mengato, "Meniscal tears: The effect of meniscectomy and of repair on intraarticular contact areas and stress in the human knee," *Am. J. Sports Med.*, vol. 14, no. 4, pp. 270-275, July 1986.

[47] J.-M. Fayard, H. Pereira, E. Servien, S. Lustig, and P. Neyret, "Meniscectomy: Global Results-Complications," in *The Meniscus*, Berlin, Heidelberg: Springer Berlin Heidelberg, 2010, pp. 177-190.

[48] J. L. Cook, "The current status of treatment for large meniscal defects.," *Clin. Orthop. Relat. Res.*, no. 435, pp. 88-95, June 2005.

[49] A. Hede, E. Larsen, and H. Sandberg, "The long term outcome of open total and partial meniscectomy related to the quantity and site of the meniscus removed.," *Int. Orthop.*, vol. 16, no. 2, pp. 122-5, 1992.

[50] H. Roos, M. Lauren, T. Adalberth, E. M. Roos, K. Jonsson, and L. S. Lohmander, "Knee osteoarthritis after meniscectomy: Prevalence of radiographic changes after twenty-one years, compared with matched controls," *Arthritis Rheum.*, vol. 41, no. 4, pp. 687-693, April 1998.

[51] M. Englund and L. S. Lohmander, "Risk factors for symptomatic knee osteoarthritis fifteen to twenty-two years after meniscectomy," *Arthritis Rheum.*, vol. 50, no. 9, pp. 2811-2819, September 2004.

[52] I. D. McDermott and A. A. Amis, "The consequences of meniscectomy," *J. Bone Jt. Surg. —Br. Vol.*, vol. 88-B, no. 12, pp. 1549-1556, 2006.

[53] H. Luks, "Recovery After Meniscal Tear Surgery," *Orthopedic Surgery and Sports Medicine*, 2018. [Online]. Available: https://www.howardluksmd.com/meniscal-tear-recovery-surgery/.[Accessed: 8 Apr. 2018].

[54] M. ElAttar, A. Dhollander, R. Verdonk, K. F. Almqvist, and P. Verdonk, "Twenty-six years of meniscal allograft transplantation: Is it still experimental? A meta-analysis of 44 trials," *Knee Surgery, Sport. Traumatol. Arthrosc.*, vol. 19, no. 2, pp. 147-157, 2011.

[55] Y. Wada, M. Amid, F. Harwood, H. Moriya, and D. Amiel, "Architectural remodeling in deep frozen meniscal allografts after total meniscectomy.," *Arthroscopy*, vol. 14, no. 3, pp. 250-7, April 1998.

[56] B.-S. Lee, J.-W. Chung, J.-M. Kim, W.-J. Cho, K.-A. Kim, and S.-I. Bin, "Morphologic Changes in Fresh-Frozen Meniscus Allografts Over 1 Year," *Am. J. Sports Med.*, vol. 40, no. 6, pp. 1384-1391, June 2012.

[57] T. G. van Tienen, G. Hannink, and P. Buma, "Meniscus Replacement Using Synthetic Materials," *Clin. Sports Med.*, vol. 28, no. 1, pp. 143-156, January 2009.

[58] K. Messner, "Meniscal substitution with a Teflon-periosteal composite graft: a rabbit experiment," *Biomaterials*, vol. 15, no. 3, pp. 223-230, February 1994.

[59] K. Sommerlath, M. Gallino, and J. Gillquist, "Biomechanical characteristics of different artificial substitutes for rabbit medial meniscus and effect of prosthesis size on knee cartilage," *Clin. Biomech.*, vol. 7, no. 2, pp. 97-103, May 1992.

[60] S.-W. Kang et al., "Regeneration of whole meniscus using meniscal cells and polymer scaffolds in a rabbit total meniscectomy model," *J. Biomed. Mater. Res. Part A*, vol. 78A, no. 3, pp. 638-651, September 2006.

[61] C. Chiari et al., "A tissue engineering approach to meniscus regeneration in a sheep model," *Osteoarthr. Cartil.*, vol. 14, no. 10, pp. 1056-1065, October 2006.

[62] E. Kon et al., "Tissue engineering for total meniscal substitution: animal study in sheep model—results at 12 months.," *Tissue Eng. Part A*, vol. 18, no. 15-16, pp. 1573-82, August 2012.

[63] M. Kobayashi, J. Toguchida, and M. Oka, "Development of an artificial meniscus using polyvinyl alcohol-hydrogel for early return to, and continuance of, athletic life in sportspersons with severe meniscus injury. I: Mechanical evaluation," *Knee*, vol. 10, no. 1, pp. 47-51, 2003.

[64] M. Kobayashi, Y. S. Chang, and M. Oka, "A two year in vivo study of polyvinyl alcohol-hydrogel (PVA-H) artificial meniscus," *Biomaterials*, vol. 26, no. 16, pp. 3243-3248, 2005.

[65] B. T. Kelly et al., "Hydrogel meniscal replacement in the sheep knee: Preliminary evaluation of chondroprotective effects," *Am. J. Sports Med.*, vol. 35, no. 1, pp. 43-52, 2007.

[66] J. L. Holloway, A. M. Lowman, and G. R. Palmese, "Mechanical evaluation of poly(vinyl alcohol)-based fibrous composites as biomaterials for meniscal tissue replacement," *Acta Biomater.*, vol. 6, no. 12, pp. 4716-4724, 2010.

[67] J. L. Holloway, A. M. Lowman, M. R. Vanlandingham, and G. R. Palmese, "Interfacial optimization of fiber-reinforced hydrogel composites for soft fibrous tissue applications," *Acta Biomater.*, vol. 10, no. 8, pp. 3581-3589, 2014.

[68] J. L. Holloway, "Development and Characterization of UHMWPE Fiber-Reinforced Hydrogels For Meniscal Replacement," Drexel University, 2012.

[69] W. G. Rodkey et al., "Comparison of the Collagen Meniscus Implant with Partial Meniscectomy," *J. Bone Jt. Surgery—American Vol.*, vol. 90, no. 7, pp. 1413-1426, July 2008.

[70] P. Buma, N. N. Ramrattan, T. G. van Tienen, and R. P. H. Veth, "Tissue engineering of the meniscus.," *Biomaterials*, vol. 25, no. 9, pp. 1523-32, April 2004.

[71] K. R. Stone, W. G. Rodkey, R. Webber, L. McKinney, and J. R. Steadman, "Meniscal regeneration with copolymeric collagen scaffolds," *Am. J. Sports Med.*, vol. 20, no. 2, pp. 104-111, March 1992.

[72] J. C. Monllau, X. Pelfort, and M. Tey, "Collagen Meniscus Implant: Technique and Results," in *The Meniscus*, Berlin, Heidelberg: Springer Berlin Heidelberg, 2010, pp. 373-382.

[73] J. C. Monllau et al., "Outcome After Partial Medial Meniscus Substitution With the Collagen Meniscal Implant at a Minimum of 10 Years' Follow-up," *Arthrosc. J. Arthrosc. Relat. Surg.*, vol. 27, no. 7, pp. 933-943, July 2011.

[74] A. Ginés, P. Hinarejos, M. Tey, and J. C. Monllau, "COLLAGEN MENISCUS IMPLANT. OUTCOMES AFTER 4 TO 7 YEARS," *Orthop. Proc.*, vol. 88-B, no. SUPP_II, p. 329, May 2006.

[75] S. J. Spencer, A. Saithna, M. R. Carmont, M. S. Dhillon, P. Thompson, and T. Spalding, "Meniscal scaffolds: Early experience and review of the literature," *Knee*, vol. 19, no. 6, pp. 760-765, December 2012.

[76] E. Genovese et al., "Follow-up of collagen meniscus implants by MRI," *Radiol. Med.*, vol. 112, no. 7, pp. 1036-1048, October 2007.

[77] T. G. Tienen et al., "Replacement of the Knee Meniscus by a Porous Polymer Implant," *Am. J. Sports Med.*, vol. 34, no. 1, pp. 64-71, January 2006.

[78] R. T. C. Welsing et al., "Effect on Tissue Differentiation and Articular Cartilage Degradation of a Polymer Meniscus Implant," *Am. J. Sports Med.*, vol. 36, no. 10, pp. 1978-1989, October 2008.

[79] S. A. Maher et al., "Evaluation of a Porous Polyurethane Scaffold in a Partial Meniscal Defect Ovine Model," *Arthrosc. J. Arthrosc. Relat. Surg.*, vol. 26, no. 11, pp. 1510-1519, November 2010.

[80] R. H. Brophy, J. Cottrell, S. A. Rodeo, T. M. Wright, R. F. Warren, and S. A. Maher, "Implantation of a synthetic meniscal scaffold improves joint contact mechanics in a partial meniscectomy cadaver model," *J. Biomed. Mater. Res. Part A*, vol. 9999A, no. 3, p. NA-NA, March 2009.

[81] P. Verdonk et al., "Successful Treatment of Painful Irreparable Partial Meniscal Defects With a Polyurethane Scaffold," *Am. J. Sports Med.*, vol. 40, no. 4, pp. 844-853, April 2012.

[82] C. Van Der Straeten, B. Doyen, C. Dutordoir, W. Goedertier, S. Pirard, and J. Victor, "SHORT-AND MEDIUM-TERM RESULTS OF ARTIFICIAL MENISCAL IMPLANTS," *Orthop. Proc.*, vol. 98-B, no. SUPP_4, p. 91, January 2016.

[83] J. J. Elsner, S. Portnoy, G. Zur, F. Guilak, A. Shterling, and E. Linder-Ganz, "Design of a Free-Floating Polycarbonate-Urethane Meniscal Implant Using Finite Element Modeling and Experimental Validation," *J. Biomech. Eng.*, vol. 132, no. 9, p. 95001, 2010.

[84] M. Shemesh, R. Asher, E. Zylberberg, F. Guilak, E. Linder-Ganz, and J. J. Elsner, "Viscoelastic properties of a synthetic meniscus implant," *J. Mech. Behav. Biomed. Mater.*, vol. 29, pp. 42-55, 2014.

[85] R. Pollanen, A.-M. Tikkanen, M J Lammi, and R. Lappalainen, "The effect of loading and material on the biomechanical properties and vitality of bovine cartilage in vitro.," *J. Appl. Biomater. Biomech.*, vol. 9, no. 1, pp. 47-53, 2011.

[86] G. Zur et al., "Chondroprotective effects of a polycarbonate-urethane meniscal implant: Histopathological results in a sheep model," *Knee Surgery, Sport. Traumatol. Arthrosc.*, vol. 19, no. 2, pp. 255-263, 2011.

[87] S. A. Maher, S. A. Rodeo, H. G. Potter, L. J. Bonassar, T. M. Wright, and R. F. Warren, "A Pre-Clinical Test Platform for the Functional Evaluation of Scaffolds for Musculoskeletal Defects: The Meniscus," *HSS J.*, vol. 7, no. 2, pp. 157-163, 2011.

[88] I. Kutzner et al., "Loading of the knee joint during activities of daily living measured in vivo in five subjects," *J. Biomech.*, vol. 43, no. 11, pp. 2164-2173, 2010.

[89] C. Tudor-Locke et al., "How many steps/day are enough? For adults.," *Int. J. Behav. Nutr. Phys. Act.*, vol. 8, p. 79, July 2011.

[90] A. C. T. Vrancken et al., "3D geometry analysis of the medial meniscus—a statistical shape modeling approach.," *J. Anat.*, vol. 225, no. 4, pp. 395-402, October 2014.

[91] K. Bloecker et al., "Revision 1 Size and position of the healthy meniscus, and its Correlation with sex, height, weight, and bone area—a cross-sectional study," *BMC Musculoskelet. Disord.*, vol. 12, pp. 1-9, 2011.

[92] A. M. Lowman and N. A. Peppas, "Hydrogels," *Encycl. Control. drug Deliv.*, vol. 1, pp. 397-418, 1999.

[93] C. M. Hassan and N. A. Peppas, "Structure and Morphology of Freeze/Thawed PVA Hydrogels," *Macromolecules*, vol. 33, no. 7, pp. 2472-2479, April 2000.

[94] V. I. Lozinsky, L. G Damshkaln, I. N. Kurochkin, and I. I. Kurochkin, "Study of cryostructuring of polymer systems: 28. Physicochemical properties and morphology of poly(vinyl alcohol) cryogels formed by multiple freezing-thawing," *Colloid J.*, vol. 70, no. 2, pp. 189-198, April 2008.

[95] R. Ricciardi, F. Auriemma, C. Gaillet, C. De Rosa, and F. Lauprêtre, "Investigation of the Crystallinity of Freeze/Thaw Poly(vinyl alcohol) Hydrogels by Different Techniques," *Macromolecules*, vol. 37, no. 25, pp. 9510-9516, December 2004.

[96] T. Hatakeyema, J. Uno, C. Yamada, A. Kishi, and H. Hatakeyama, "Gel-sol transition of poly(vinyl alcohol) hydrogels formed by freezing and thawing," *Thermochim. Acta*, vol. 431, no. 1-2, pp. 144-148, June 2005.

[97] C. M. Hassan and N. A. Peppas, "Structure and Applications of Poly(vinyl alcohol) Hydrogels Produced by Conventional Crosslinking or by Freezing/Thawing Methods," in *Biopolymers—PVA Hydrogels, Anionic Polymerisation Nanocomposites, Berlin, Heidelberg: Springer Berlin Heidelberg*, 2000, pp. 37-65.

[98] A. JOSHI et al., "Functional compressive mechanics of a PVA/PVP nucleus pulposus replacement," *Biomaterials*, vol. 27, no. 2, pp. 176-184, January 2006.

[99] N. A. Peppas, "Turbidimetric studies of aqueous poly (vinyl alcohol) solutions," *Die Makromol. Chemie*, vol. 176, no. 11, pp. 3433-3440, November 1975.

[100] S. R. Stauffer and N. A. Peppast, "Poly(vinyl alcohol) hydrogels prepared by freezing-thawing cyclic processing," *Polymer (Guildf).*, vol. 33, no. 18, pp. 3932-3936, September 1992.

[101] K. L. Spiller, S. J. Laurencin, D. Charlton, S. A. Maher, and A. M. Lowman, "Superporous hydrogels for cartilage repair: Evaluation of the morphological and mechanical properties," *Acta Biomater.*, vol. 4, no. 1, pp. 17-25, January 2008.

[102] M. I. Baker, S. P. Walsh, Z. Schwartz, and B. D. Boyan, "A review of polyvinyl alcohol and its uses in cartilage and orthopedic applications," *J. Biomed. Mater. Res. —Part B Appl. Biomater.*, vol. 100 B, no. 5, pp. 1451-1457, 2012.

[103] Y.-S. Chang, H.-O. Gu, M. Kobayashi, and M. Oka, "Comparison of the bony ingrowth into an osteochondral defect and an artificial osteochondral composite device in load-bearing joints," *Knee*, vol. 5, no. 3, pp. 205-213, June 1998.

[104] J. D. Henderson, R. H. Mullarky, and D. E. Ryan, "Tissue biocompatibility of kevlar aramid fibers and polymethylmethacrylate, composites in rabbits," *J. Biomed. Mater. Res.*, vol. 21, no. 1, pp. 59-64, January 1987.

[105] E. Salernitano and C. Migliaresi, "Composite Materials for Biomedical Applications: A Review," https://doi.org/10.1177/228080000300100102, January 2018.

[106] M. Jassal and S. Ghosh, *Aramid fibres—An overview*, vol. 27.2002.

[107] F. Franceschini and M. Galetto, "A new approach for evaluation of risk priorities of failure modes in FMEA," *Int. J. Prod. Res.*, vol. 39, no. 13, pp. 2991-3002, January 2001.

[108] A. Bedi et al., "Dynamic Contact Mechanics of the Medial Meniscus as a Function of Radial Tear, Repair, and Partial Meniscectomy," *J. Bone Jt. Surgery—American Vol.*, vol. 92, no. 6, pp. 1398-1408, June 2010.

[109] J. Babu, R. M. Shalvoy, and S. B. Behrens, "Diagnosis and Management of Meniscal Injury.," *R. I. Med. J.* (2013), vol. 99, no. 10, pp. 27-30, October 2016.

[110] M. Tissakht and A. M. Ahmed, "Tensile stress-strain characteristics of the human meniscal material," *J. Biomech.*, vol. 28, no. 4, pp. 411-422, 1995.

[111] D. Bruni, F. Iacono, I. Akkawi, M. Gagliardi, S. Zaffagnini, and M. Marcacci, "Unicompartmental knee replacement: A historical overview," *Joints*, vol. 1, no. 2, pp. 45-47, 2013.

[112] R. Spencer Jones et al., "Direct measurement of hoop strains in the intact and torn human medial meniscus," *Clin. Biomech.*, vol. 11, no. 5, pp. 295-300, 1996.

[113] M. Freutel et al., "Medial meniscal displacement and strain in three dimensions under compressive loads: MR assessment," *J. Magn. Reson. Imaging*, vol. 40, no. 5, pp. 1181-1188, 2014.

[114] A. Seitz, R. Kasisari, L. Claes, A. Ignatius, and L. Dürselen, "Forces acting on the anterior meniscotibial ligaments," *Knee Surgery, Sport. Traumatol. Arthrosc.*, vol. 20, no. 8, pp. 1488-1495, 2012.

[115] K. L. Markolf, S. R. Jackson, and D. R. McAllister, "Force measurements in the medial meniscus posterior horn attachment: Effects of anterior cruciate ligament removal," *Am. J. Sports Med.*, vol. 40, no. 2, pp. 332-338, 2012.

[116] M. A. Sweigart et al., "Intraspecies and interspecies comparison of the compressive properties of the medial meniscus," *Ann. Biomed. Eng.*, vol. 32, no. 11, pp. 1569-1579, 2004.

[117] M. D. Joshi, J.-K Suh, T. Marui, and S. L.-. Woo, "Interspecies variation of compressive biomechanical properties of the meniscus," *J. Biomed. Mater. Res.*, vol. 29, no. 7, pp. 823-828, 1995.

[118] H. N. Chia and M. L. Hull, "Compressive moduli of the human medial meniscus in the axial and radial directions at equilibrium and at a physiological strain rate," *J. Orthop. Res.*, vol. 26, no. 7, pp. 951-956, 2008.

[119] D. Kumar, K. T. Manal, and K. S. Rudolph, "Knee joint loading during gait in healthy controls and individuals with knee osteoarthritis," *Osteoarthr. Cartil.*, vol. 21, no. 2, pp. 298-305, 2013.

[120] B. B. Seedhom, D. Dowson, and V. Wright, "Proceedings: Functions of the menisci. A preliminary study.," *Ann. Rheum. Dis.*, vol. 33, no. 1, pp. 111-111, 1974.

[121] M. McDowell, C. Fryar, C. Ogden, and K. Flegal, "Anthropometric reference data for children and adults: United States, 2003-2006," *Natl. Health Stat. Report.*, no. 10, pp. 2003-2006, 2008.

[122] T. Fukubayashi and H. Kurosawa, "the contact area and pressure distribution pattern of the knee: A study of normal and osteoarthrotic knee joints," *Acta Orthop.*, vol. 51, no. 1-6, pp. 871-879, 1980.

[123] A. Bedi et al., "Dynamic contact mechanics of the medial meniscus as a function of radial tear, repair, and partial meniscectomy," *J. Bone Jt. Surg. —Ser. A*, vol. 92, no. 6, pp. 1398-1408, 2010.

[124] P. Cignoni et al., "MeshLab: an Open-Source Mesh Processing Tool," *Sixth Eurographics Ital. Chapter Conf.*, pp. 129-136, 2008.

[125] L. McCann, E. Ingham, Z. Jin, and J. Fisher, "Influence of the meniscus on friction and degradation of cartilage in the natural knee joint," *Osteoarthr. Cartil.*, vol. 17, no. 8, pp. 995-1000, August 2009.

[126] A. Lowman, G. Palmese, S. Maher, R. Warren, T. Wright, and J. Holloway, "Fiber-Hydrogel Composite for Tissue Replacement," 288199, 19 May 2010.

What is claimed is:

1. An artificial meniscus for a knee joint, the artificial meniscus comprising:
   a peripheral edge, an interior edge, anterior and posterior horns, an inferior surface, and a superior surface;
   a polymer material;
   at least one circumferential fiber bundle extending in a circumferential direction between the anterior horn and the posterior horn; and
   at least one non-circumferential fiber bundle separate and distinct from the at least one circumferential fiber bundle and defining radial segments extending in a direction perpendicular to the circumferential direction to inhibit tears in the circumferential direction;
   wherein the at least one circumferential fiber bundle and the at least one non-circumferential fiber bundle are each embedded in the polymer material, the at least one non-circumferential fiber bundle fully encapsulated within the polymer material, and the at least one circumferential fiber bundle extending out of the anterior and posterior horns of the artificial meniscus and terminating in ends that are configured for fixation to bone;
   wherein the at least one non-circumferential fiber bundle extends back and forth in an at least partially curved line from positions near the peripheral edge of the artificial meniscus to positions near the interior edge of the artificial meniscus;
   wherein the at least one non-circumferential fiber bundle alternates between curved segments near the peripheral edge and the interior edge of the artificial meniscus and straight radial segments between the peripheral edge and the interior edge of the artificial meniscus; and
   wherein the at least one circumferential fiber bundle has a shape different from a shape of the at least one non-circumferential fiber bundle.

2. The artificial meniscus of claim 1, wherein the at least one circumferential fiber bundle includes multiple circumferential fiber bundles spaced from each other in a Z-direction.

3. The artificial meniscus of claim 2, wherein the multiple circumferential fiber bundles spaced from each other in the Z-direction are positioned adjacent to the peripheral edge of the artificial meniscus.

4. The artificial meniscus of claim 1, wherein the at least one circumferential fiber bundle includes multiple circumferential fiber bundles spaced between the peripheral edge and the interior edge of the artificial meniscus.

5. The artificial meniscus of claim 4, wherein the multiple circumferential fiber bundles converge as they approach the anterior and posterior horns of the artificial meniscus.

6. The artificial meniscus of claim 1, wherein a combined ultimate tensile strength of the at least one circumferential fiber bundle is at least 12 MPa.

7. The artificial meniscus of claim 1, wherein the at least one non-circumferential fiber bundle is part of woven sheet of fiber bundles.

8. The artificial meniscus of claim 1, wherein the at least one non-circumferential fiber bundle includes multiple non-circumferential fiber bundles spaced from each other in a Z-direction.

9. The artificial meniscus of claim 1, wherein the at least one non-circumferential fiber bundle is positioned adjacent the superior surface or the inferior surface of the artificial meniscus, and wherein the at least one non-circumferential fiber bundle follows a curvature of the adjacent superior or inferior surface.

10. The artificial meniscus of claim 1, wherein a combined ultimate tensile strength of the at least one non-circumferential fiber bundle is at least 1 MPa.

11. The artificial meniscus of claim 1, wherein the radial segments of the at least one non-circumferential fiber bundle are spaced across the artificial meniscus between the anterior horn and the posterior horn.

12. The artificial meniscus of claim 1, wherein the polymer material is a uniform, continuous structure surrounding the at least one circumferential fiber bundle and the at least one non-circumferential fiber bundle.

13. The artificial meniscus of claim 1, wherein both the at least one circumferential fiber bundle and the at least one non-circumferential fiber bundle are formed from a synthetic material.

14. The artificial meniscus of claim 1, wherein the polymer material penetrates individual fibers of the at least one circumferential fiber bundle and the at least one non-circumferential fiber bundle.

15. The artificial meniscus of claim 1, wherein the polymer material is a hydrogel.

* * * * *